US011938172B2

(12) United States Patent
Li

(10) Patent No.: US 11,938,172 B2
(45) Date of Patent: *Mar. 26, 2024

(54) METHOD FOR REGULATING AND CONTROLLING GLP-1/GLP-1R AND DRUG

(71) Applicant: Talengen International Limited, Hong Kong (CN)

(72) Inventor: Jinan Li, Guangdong (CN)

(73) Assignee: Talengen International Limited, Hong Kong (CN)

( * ) Notice: Subject to any disclaimer, the term of this patent is extended or adjusted under 35 U.S.C. 154(b) by 279 days.

This patent is subject to a terminal disclaimer.

(21) Appl. No.: 16/624,170

(22) PCT Filed: Jun. 19, 2018

(86) PCT No.: PCT/CN2018/091838
§ 371 (c)(1),
(2) Date: Dec. 18, 2019

(87) PCT Pub. No.: WO2018/233604
PCT Pub. Date: Dec. 27, 2018

(65) Prior Publication Data
US 2020/0206324 A1 Jul. 2, 2020

(30) Foreign Application Priority Data

Jun. 19, 2017 (WO) ............... PCT/CN2017/089067

(51) Int. Cl.

| A61K 38/48 | (2006.01) |
| A61K 45/06 | (2006.01) |
| A61P 1/16 | (2006.01) |
| A61P 1/18 | (2006.01) |
| A61P 3/04 | (2006.01) |
| A61P 3/10 | (2006.01) |
| A61P 5/48 | (2006.01) |
| A61P 5/50 | (2006.01) |
| A61P 7/00 | (2006.01) |
| A61P 25/00 | (2006.01) |
| A61P 25/16 | (2006.01) |

(52) U.S. Cl.
CPC ............ *A61K 38/484* (2013.01); *A61K 45/06* (2013.01); *A61P 1/16* (2018.01); *A61P 1/18* (2018.01); *A61P 3/04* (2018.01); *A61P 3/10* (2018.01); *A61P 5/48* (2018.01); *A61P 5/50* (2018.01); *A61P 7/00* (2018.01); *A61P 25/00* (2018.01); *A61P 25/16* (2018.01)

(58) Field of Classification Search
CPC .......... C12Y 304/21007; C12N 9/6435; A61K 38/484
See application file for complete search history.

(56) References Cited

U.S. PATENT DOCUMENTS

| 4,645,668 A | 2/1987 | Pinnell |
| 5,304,383 A * | 4/1994 | Eibl ............... C12Y 304/21007 424/499 |
| 5,776,452 A * | 7/1998 | Eibl ........................ A61P 7/02 424/94.63 |
| 6,057,122 A | 5/2000 | Davidson |
| 7,067,492 B2 | 6/2006 | Ny |
| 10,441,639 B2 | 10/2019 | Blackman et al. |
| 10,864,257 B2 | 12/2020 | Li |
| 11,007,253 B2 | 5/2021 | Li |
| 11,090,372 B2 | 8/2021 | Li |
| 11,311,607 B2 | 4/2022 | Li |
| 2003/0054988 A1 | 3/2003 | Ji et al. |
| 2003/0147879 A1 | 8/2003 | Ny et al. |
| 2004/0043026 A1 | 3/2004 | Tuan et al. |
| 2004/0097455 A1 | 5/2004 | Borunda et al. |
| 2005/0124036 A1 | 6/2005 | Susilo et al. |
| 2005/0124534 A1 | 6/2005 | Noble et al. |
| 2005/0250694 A1 | 11/2005 | Ma |
| 2013/0003436 A1 | 11/2013 | Wilson |
| 2015/0133458 A1 | 5/2015 | Mann |
| 2016/0362498 A1 | 12/2016 | Zhang et al. |
| 2018/0369345 A1 | 12/2018 | Li |
| 2019/0083586 A1 | 3/2019 | Li |
| 2019/0231854 A1 | 8/2019 | Robitaille |
| 2019/0307861 A1 | 10/2019 | Li |
| 2019/0314464 A1 | 10/2019 | Li |
| 2019/0314465 A1 | 10/2019 | Li |
| 2019/0314466 A1 | 10/2019 | Li |
| 2019/0314467 A1 | 10/2019 | Li |
| 2019/0314468 A1 | 10/2019 | Li |
| 2019/0328848 A1 | 10/2019 | Li |
| 2019/0328849 A1 | 10/2019 | Li |
| 2019/0328850 A1 | 10/2019 | Li |

(Continued)

FOREIGN PATENT DOCUMENTS

| CA | 2707266 A1 | 6/2009 |
| CA | 2823491 A1 | 7/2012 |
| CA | 2939897 A1 | 8/2015 |
| CA | 3002915 A1 | 5/2017 |
| CN | 1585649 A | 2/2005 |
| CN | 1668312 A | 9/2005 |
| CN | 1723197 A | 1/2006 |
| CN | 1768138 A | 5/2006 |
| CN | 101044136 A | 9/2007 |
| CN | 101573134 A | 11/2009 |
| CN | 101628113 A | 1/2010 |

(Continued)

OTHER PUBLICATIONS

Jin et al. "Urokinase-Type Plasminogen Activator, an Endogenous Antibiotic" JID 2005:192 (Aug. 1) 9 pages (Year: 2005).*

(Continued)

*Primary Examiner* — Thane Underdahl
(74) *Attorney, Agent, or Firm* — Wolf, Greenfield & Sacks, P.C.

(57) ABSTRACT

The present invention discloses the use of plasminogen to regulate GLP-1/GLP-1R and treat a GLP-1/GLP-1R-related condition.

18 Claims, 19 Drawing Sheets
Specification includes a Sequence Listing.

(56) References Cited

U.S. PATENT DOCUMENTS

| | | |
|---|---|---|
| 2019/0343930 A1 | 11/2019 | Li |
| 2019/0343931 A1 | 11/2019 | Li |
| 2019/0351033 A1 | 11/2019 | Li |
| 2019/0365872 A1 | 12/2019 | Li |
| 2020/0078449 A1 | 3/2020 | Li |
| 2020/0085920 A1 | 3/2020 | Li |

FOREIGN PATENT DOCUMENTS

| | | | |
|---|---|---|---|
| CN | 101918548 A | 12/2010 | |
| CN | 102121023 A | 7/2011 | |
| CN | 102482338 A | 5/2012 | |
| CN | 103384722 A | 11/2013 | |
| CN | 104914247 A | 9/2015 | |
| CN | 105705520 A | 6/2016 | |
| CN | 106029884 A | 10/2016 | |
| CN | 106890318 A | 6/2017 | |
| CN | 106890320 A | 6/2017 | |
| CN | 106890324 A | 6/2017 | |
| DE | 00980071 T1 | 3/2005 | |
| DK | 1411128 T3 | 2/2009 | |
| EP | 0307847 B1 | 12/1992 | |
| EP | 1411128 A1 | 4/2004 | |
| EP | 3556392 A1 | 10/2019 | |
| JP | 2010-155856 A | 7/2010 | |
| JP | 2020-502102 A | 1/2020 | |
| JP | 2020-502140 A | 1/2020 | |
| JP | 2020-502153 A | 1/2020 | |
| JP | 2020-502154 A | 1/2020 | |
| JP | 2020-502156 A | 1/2020 | |
| JP | 2020-510627 A | 4/2020 | |
| KR | 101467109 B1 | 12/2014 | |
| TW | 201625294 A | 7/2016 | |
| TW | I568745 B | 2/2017 | |
| TW | 201722465 A | 7/2017 | |
| TW | I624268 B | 5/2018 | |
| TW | 20182279 A | 7/2018 | |
| TW | 201822807 A | 7/2018 | |
| TW | 201822808 A | 7/2018 | |
| TW | 201201822783 A | 7/2018 | |
| TW | I642442 B | 12/2018 | |
| TW | I669130 B | 8/2019 | |
| WO | WO 99/00420 A1 | 1/1999 | |
| WO | WO 00/10506 A2 | 3/2000 | |
| WO | WO-0158476 A2 * | 8/2001 | A61K 31/00 |
| WO | WO 02/44393 A1 | 6/2002 | |
| WO | WO 2004/041155 A2 | 5/2004 | |
| WO | WO 2004/052853 A2 | 6/2004 | |
| WO | WO 2006/023864 A1 | 3/2006 | |
| WO | WO 2008/026999 A2 | 3/2008 | |
| WO | WO 2010/111271 A1 | 9/2010 | |
| WO | WO 2011/004011 A1 | 1/2011 | |
| WO | WO 2011/057138 A1 | 5/2011 | |
| WO | WO 2011/139973 A2 | 11/2011 | |
| WO | WO 2015/023752 A1 | 2/2015 | |
| WO | WO 2015/026494 A2 | 2/2015 | |
| WO | WO 2017/077380 A1 | 5/2017 | |

OTHER PUBLICATIONS

Schoppmann et al. "Production and Quality Assurance of LYS-Plasminogen Steam Treated" Haemostasis 18: suppl. I, pp. 157 (1988) Abstrat Only (Year: 1988).*

[No Author Listed] Score_Search_Results_16470173_7_pages.

[No Author Listed] Uniprot Protein Database. Accession No. P00747, Human PLMN. Accessed Aug. 10, 2020; 14 pages.

Aisina et al., Structure and functions of plasminogen/plasmin system. Bioorg Khim. Nov.-Dec. 2014;40(6):642-57. Russian. doi: 10.1134/s1068162014060028.

Badylak et al., The beneficial effect of lys-plasminogen upon the thrombolytic efficacy of urokinase in a dog model of peripheral arterial thrombosis. Haemostasis. 1991;21(5):278-85. doi: 10.1159/000216237.

Bergheim et al. Metformin prevents alcohol-induced liver injury in the mouse: Critical role of plasminogen activator inhibitor-1. Gastroenterology. Jun. 2006;130(7):2099-112. doi: 10.1053/j.gastro.2006.03.020.

Gutierrez et al., Tumor development is retarded in mice lacking the gene for urokinase-type. Plasminogen activator or its inhibitor, plasminogen activator inhibitor-1. Cancer Res. Oct. 15, 2000;60(20):5839-47.

Haraguchi et al., t-PA promotes glomerular plasmin generation and matrix degradation in experimental glomerulonephritis. Kidney Int. Jun. 2001;59(6):2146-55. doi: 10.1046/j.1523-1755.2001.00729.x.

Kanduc et al., Homology, similarity, and identity in peptide epitope immunodefinition. J Pept Sci. Aug. 2012;18(8):487-94. doi: 10.1002/psc.2419. Epub Jun. 14, 2012.

Lijnen, Pathophysiology of the plasminogen/plasmin system. Int J Clin Lab Res. 1996;26(1):1-6. doi: 10.1007/BF02644767.

Matsuoka et al., Plasminogen-mediated activation and release of hepatocyte growth factor from extracellular matrix. Am J Respir Cell Mol Biol. Dec. 2006;35(6):705-13. doi: 10.1165/rcmb.2006-0006OC. Epub Jul. 13, 2006.

O'Reilly et al., Angiostatin: a circulating endothelial cell inhibitor that suppresses angiogenesis and tumor growth. Cold Spring Harb Symp Quant Biol. 1994;59:471-82. doi: 10.1101/sqb.1994.059.01.052.

Oh et al., The role of plasminogen in angiogenesis in vivo. J Thromb Haemost. Aug. 2003;1(8):1683-7. doi: 10.1046/j.1538-7836.2003.00182.x.

Stefansson et al., Inhibition of angiogenesis in vivo by plasminogen activator inhibitor-1. J Biol Chem. Mar. 16, 20016;276(11):8135-41. doi: 10.1074/jbc.M007609200. Epub Nov. 16, 2000.

Takeshita et al., Increased expression of plasminogen activator inhibitor-1 in cardiomyocytes contributes to cardiac fibrosis after myocardial infarction. Am J Pathol. Feb. 2004;164(2):449-56. doi: 10.1016/S0002-9440(10)63135-5.

Thacil et al., Ligneous conjunctivitis with plasminogen deficiency. Br J Haematol. May 2009;145(3):269. doi: 10.1111/j.1365-2141.2008.07445.x.

Vogten et al., Angiostatin inhibits experimental liver fibrosis in mice. Int J Colorectal Dis. Jul. 2004;19(4):387-94. doi: 10.1007/s00384-003-0562-4. Epub Jan. 10, 2004.

U.S. Appl. No. 16/470,162, filed Jun. 14, 2019, Li et al.
U.S. Appl. No. 16/470,172, filed Jun. 14, 2019, Li et al.
U.S. Appl. No. 16/470,179, filed Jun. 14, 2019, Li et al.
U.S. Appl. No. 16/470,186, filed Jun. 14, 2019, Li et al.
PCT/CN2017/089053, Sep. 18, 2017, International Search Report and Written Opinion.
PCT/CN2017/089054, Sep. 11, 2017, International Search Report and Written Opinion.
PCT/CN2017/089055, Sep. 14, 2017, International Search Report and Written Opinion.
PCT/CN2017/089056, Aug. 23, 2017, International Search Report and Written Opinion.
PCT/CN2017/089057, Aug. 30, 2017, International Search Report and Written Opinion.
PCT/CN2017/089058, Aug. 24, 2017, International Search Report and Written Opinion.
PCT/CN2018/091838, Sep. 12, 2018, International Search Report and Written Opinion.
International Search Report and Written Opinion dated Sep. 18, 2017, in connection with PCT/CN2014/089053.
International Search Report and Written Opinion dated Sep. 11, 2017, in connection with PCT/CN2014/089054.
International Search Report and Written Opinion dated Sep. 14, 2017, in connection with PCT/CN2014/089055.
International Search Report and Written Opinion dated Aug. 23, 2017, in connection with PCT/CN2014/089056.
International Search Report and Written Opinion dated Aug. 30, 2017, in connection with PCT/CN2014/089057.
International Search Report and Written Opinion dated Aug. 24, 2017, in connection with PCT/CN2014/089058.

(56) References Cited

OTHER PUBLICATIONS

International Search Report and Written Opinion dated Sep. 12, 2018, in connection with PCT/CN2018/091838.
[No Author Listed] Treatment Options. Pulmonary Fibrosis Foundation. 2019. https://www.pulmonaryfibrosis.org/life-with-pf/pulmonary-fibrosis-treatment-options [last accessed Nov. 7, 2019], 14 pages.
Beier et al., Alcoholic liver disease and the potential role of plasminogen activator inhibitor-1 and fibrin metabolism. Exp. Biol. Med. (Maywood). Jan. 31, 2012;237(1):1-9.
Edgtton et al., Plasmin is not protective in experimental renal interstitial fibrosis. Kidney Intl. Jul. 2004;66(1):68-76.
Farkas et al., Pulmonary hypertension and idiopathic pulmonary fibrosis: a tale of angiogenesis, apoptosis, and growth factors. Am J Respir Cell Mol Biol. Jul. 2011;45(1):1-15. doi: 10.1165/rcmb.2010-0365TR. Epub Nov. 5, 2010. Review.
Eitzman et al., Bleomycin-induced pulmonary fibrosis in transgenic mice that either lack or overexpress the murine plasminogen activator inhibitor-1 gene. J. Clin. Invest. Jan. 1996;97(1):232-7.
Fisher et al., Displacement of tissue bound plasminogen by glucose: a possible mechanism in the pathogenesis of diabetic nephropathy. Endocrinol Metab. Nov. 30, 1997;4:371-6.
Genbank Submission; NIH/NCBI, Accession No. NP-000292.1, Plasminogen isoform 1 precursor [*Homo sapiens*]. May 4, 2019, 4 pages.
Ghosh et al., PAI-1 in tissue fibrosis. J Cell Physiol. Feb. 2012;227(2):493-507.
Giorgio-Miller et al., Fibrin-induced skin fibrosis in mice deficient in tissue plasminogen activator. Am J Pathol. Sep. 30, 2005;167(3):721-32.
Hattori et al., Bleomycin-induced pulmonary fibrosis in fibrinogen-null mice. J Clin Invest. 2000;106(11):1341-50.
He et al., Systemic Scleroderma and Tissue Fibrosis. J Clin Dermatol. Aug. 31, 2009;38(8):546-8.
Hu et al., Novel actions of tissue-type plasminogen activator in chronic kidney disease: a paradigm shift. Front Biosci. May 2008;13:5174-86.
Jin et al., Combination of human plasminogen kringle 5 with ionizing radiation significantly enhances the efficacy of antitumor effect. Int J Cancer. Dec. 1, 2007;121(11):2539-46.
Kitching et al., Plasminogen and plasminogen activators protect against renal injury in crescentic glomerulonephritis. J Exp Med. Mar. 3, 1997;185(5):963-8.
Li et al., Efficacy observation of integrated therapy of Urokinase and interferon for fibrosis in aged tumour patients after radiotherapy. Chin J Oncol Prev Treat. Jun. 2016;8(3): 179-80.
Liu et al., Plasminogen: structure, function and evolution. J Ocean Univ China. Oct. 2010;40(10):69-74.
Lugea et al., Pancreas recovery following caerulein-induced pancreatitis is impaired in plasminogen deficient mice. Gastroenterology. Sep. 2006; 131(3):885-899.
Marudamuthu et al., Plasminogen activator inhibitor-1 suppresses profibrotic responses in fibroblasts from fibrotic lungs. J Biol Chem. Apr. 10, 2015;290(15):9428-41.
Pohl et al., Plasminogen deficiency leads to impaired lobular reorganization and matrix accumulation after chronic liver injury. Am J Pathol. Dec. 2001;159(6):2179-86.
Pohl et al., Plasminogen deficiency accelerates the development of hepatic fibrosis in mice. Gastroenterology. Apr. 2000;118(4):A989. Paragraph 1129.
Puccetti et al., Dyslipidemias and fibrinolysis. Ital Heart J. Oct. 2002;3(10):579-86.
Schott et al., Therapy with a purified plasminogen concentrate in an infant with ligneous conjunctivitis and homozygous plasminogen deficiency. N Engl J Med. Dec. 1998;339(23):1679-86.
Swaisgood et al., The development of bleomycin induced pulmonary fibrosis in mice deficient for components of the fibrinolytic system. Am J Pathol. Jul. 2000;dated 157(1): 177-87.
Wilson et al., The safety and efficacy of low-dose tissue plasminogen activator in the treatment of systemic sclerosis. J Dermatol. Sep. 1995;22(9):637-42.
Wu et al., Experience of using Urokinase to treat systemic sclerosis. Foreign Medical Sciences Section of Dermatology and Venereology. Br J Dermatol. May 1982;104:105.
Xiao et al., Plasminogen deficiency accelerates vessel wall disease in mice predisposed to atherosclerosis. Proc Natl Acad Sci. Sep. 1997;94:10335-40.
Yang et al., Disruption of tissue-type plasminogen activator gene in mice reduces renal interstitial fibrosis in obstructive nephropathy. J Clin Invest. Dec. 2002;110(10):1525-38.
Yang et al., Pathological mechanisms of oral submucous fibrosis. Institute Biochem Biotech. Chung Shan Medical University. Jun. 2005. Doctor Thesis. pp. 1-136.
Zhu et al., The role of the plasminogen activator inhibitor-1 in the pathogenesis of hepatic fibrosis, medicine & public health. Chinese Selected Doctoral Dissertations and Master's Theses Full-Text Databases. Apr. 15, 2007;E064-4:64-7.
Zhu et al., Expression and significance of plasminogen activator inhibitor-1 in hepatic fibrosis. Chinese Hepatol. Apr. 2006;11(2):3 pages.
Cerri et al., Management of idiopathic pulmonary fibrosis. Clin Chest Med. Mar. 2012;33(1):85-94. doi: 10.1016/j.ccm.2011.11.005. Epub Dec. 28, 2011. Review.
Faller et al., Inhaled hydrogen sulfide protects against lipopolysaccharide-induced acute lung injury in mice. Med Gas Res. Oct. 1, 2012;2(1):26. doi: 10.1186/2045-9912-2-26.
Gomez-Arroyo et al., The monocrotaline model of pulmonary hypertension in perspective. Am J Physiol Lung Cell Mol Physiol. Feb. 15, 2012;302(4):L363-9. doi: 10.1152/ajplung.00212.2011. Epub Sep. 30, 2011. Review.
Li et al., Glucocorticoid with cyclophosphamide for paraquat-induced lung fibrosis. Cochrane Database Syst Rev. Aug. 7, 2014;(8):CD008084. doi: 10.1002/14651858.CD008084.pub4. Review.
Liu et al., Radix puerariae extracts ameliorate paraquat-induced pulmonary fibrosis by attenuating follistatin-like 1 and nuclear factor erythroid 2p45-related factor-2 signalling Pathways through downregulation of miRNA-21 expression. BMC Complement Altern Med. Jan. 12, 2016;16:11. doi: 10.1186/s12906-016-0991-6.
Scott et al., Extracellular matrix, supramolecular organisation and shape. J Anat. Oct. 1995;187 ( Pt 2):259-69. Review.
Specks et al., Increased expression of type VI collagen in lung fibrosis. Am J Respir Crit Care Med. Jun. 1995;151(6):1956-64.
Extended European Search Report for EP 18820383.0 dated Apr. 8, 2021.
Shen et al., Plasminogen is a key proinflammatory regulator that accelerates the healing of acute and diabetic wounds. Blood. Jun. 14, 2012;119(24):5879-87. doi: 10.1182/blood-2012-01-407825. Epub May 4, 2012. PMID: 22563086.
EP 18820383.0, Apr. 8, 2021, Extended European Search Report.
Ajjan et al., Diabetes is associated with posttranslational modifications in plasminogen resulting in reduced plasmin generation and enzyme-specific activity. Blood. Jul. 4, 2013;122(1):134-42. doi: 10.1182/blood-2013-04-494641. Epub May 22, 2013.
Barale et al., Hypercholesterolemia impairs the Glucagon-like peptide 1 action on platelets: Effects of a lipid-lowering treatment with simvastatin. Thromb Res. Aug. 2019;180:74-85. doi: 10.1016/j.thromres.2019.06.010. Epub Jun. 15, 2019.
Cao et al., Angiostatin. Semin Thromb Hemost. Feb. 2004;30(1):83-93. doi: 10.1055/s-2004-822973.
Chang et al., Human plasminogen kringle 1-5 reduces atherosclerosis and neointima formation in mice by suppressing the inflammatory signaling pathway. J Thromb Haemost. Jan. 2010;8(1):194-201. doi: 10.1111/j.1538-7836.2009.03671.x. Epub Oct. 30, 2009.
Genbank Submission; NIH/NCBI Accession No. NP_000292.1, Butera et al., Apr. 23, 2016. 3 pages.
Genbank Submission; NIH/NCBI Accession No. 1BUI_A, Parry et al., Oct. 31, 2012. 2 pages.
Hunt et al., Simplified recombinant plasmin: production and functional comparison of a novel thrombolytic molecule with plasma-derived plasmin. Thromb Haemost. Sep. 2008; 100(3):413-9.

(56) References Cited

OTHER PUBLICATIONS

Nishizawa et al., Intraportal GLP-1 stimulates insulin secretion predominantly through the hepatoportal-pancreatic vagal reflex pathways. Am J Physiol Endocrinol Metab. Aug. 1, 2013;305(3):E376-87. doi: 10.1152/ajpendo.00565.2012. Epub May 28, 2013.

Zhang et al., Therapeutic potential of angiostatin in diabetic nephropathy. J Am Soc Nephrol. Feb. 2006;17(2):475-86. doi: 10.1681/ASN.2005020217. Epub Jan. 4, 2006.

Ziegler et al., Hemobiological activity of gliclazide in diabetes mellitus. Diabetes Res Clin Pract. 1991;14 Suppl 2:S83-9. doi: 10.1016/0168-8227(91)90013-4.

* cited by examiner

METHOD FOR REGULATING AND CONTROLLING GLP-1/GLP-1R AND DRUG

CROSS REFERENCE TO RELATED APPLICATION(S)

This Application is a National Stage filing under 35 U.S.C. 371 of International Patent Application No. PCT/CN2018/091838, filed Jun. 19, 2018, which claims priority to PCT/CN2017/089067, filed Jun. 19, 2017. The entire contents of these applications are incorporated herein by reference in their entirety.

TECHNICAL FIELD

The present invention relates to the use of plasminogen to treat GLP-1/GLP-1R-related diseases by regulating GLP-1/GLP-1R.

BACKGROUND ART

GLP-1 is an endogenous hormone that promotes insulin secretion and is mainly secreted by intestinal L-cells. The expression of the proglucagon gene in small intestine L cells produces proglucagon (PG) which is processed with pro-hormoneconvertase 1/3 (PC 1/3) to release GLP-1 peptide precursor. Endopeptidase catalyzes the cleavage of GLP-1 (1-37) into two peptide segments, wherein GLP-1 (7-37) is processed with amidase to form GLP-1 (7-36) amide. Although the expression of the glucagon gene in α cells can also produce PG, prohormoneconvertase 2 (PC2) in α cells preferentially converts PG to glucagon, and thus α cells can not normally synthesize GLP-1. However, under stress or pathophysiological (e.g., type 2 diabetes mellitus) conditions, α cells can adaptively produce GLP-1.

GLP-1 can promote the normalization of insulin secretion and blood glucose in pancreatic β cells without hypoglycemia, inhibit the production of glucagon by α cells, delay gastric emptying, suppress appetite, reduce the body weight, promote the proliferation and inhibit apoptosis of β cells, and play an important role in regulating the function of islet cells[1].

Diabetes mellitus and obesity have a concurrent trend, and it is also clinically recognized that the control of patient's body weight is included in the treatment guidelines for type 2 diabetes mellitus. Studies have found that there is negative feedback regulation between GLP-1 and insulin secretion during the progression of diabetes mellitus, while patients with type 2 diabetes mellitus have damage to the entero-insular axis, accompanied by elevated lipids in circulating blood after a meal[2]. In experimental diabetic mouse models, it has been found that the lipotoxic injury of 13 cells affects the function of GLP-1, and the treatment of hyperlipemia can promote GLP-1-induced insulin secretion[3]. Currently, only glucagon-like peptide-1 receptor agonists (GLP-1 RAs) can achieve the simultaneous regulation of patient's body weight and blood glucose level in validated therapeutic regimens. GLP-1, as the basis of research on GLP-1 receptor agonists, has a blood glucose-dependent role in promoting insulin secretion. It can reduce the body weight by suppressing appetite and slowing gastric emptying[4].

GLP-1 not only reduces blood glucose in the periphery to protect islet cells and improve symptoms, but also plays a nutritional role in cell proliferation, neurogenesis and apoptosis as a neurotransmitter in the central nervous system. GLP-1R is widely distributed in rodents and human brains[5], and is expressed in the thalamus, cerebellum, brainstem, fornix, posterior area, lateral septal nucleus, caudal shell, hippocampus and cerebral cortex. GLP-1 passes through the blood-brain barrier and binds to its receptor in the corresponding brain region. GLP-1 can regulate various physiological processes of nerve cells, such as cell survival and neuronal axon growth; resist excitability, oxidative damage and death of cultured nerve cells in vitro; reduce neuron β precursor protein (βAPP); reduce the endogenous Aβ level; protect neurons against various apoptotic stimuli and induce the differentiation function of cultured nerve cells in vitro[6]. Animal experimental studies on Aβ toxic damage have found that Aβ can induce severe long-term potention (LTP) inhibition, and this damage can be reversed by GLP-1 analogues[7]. Intraventricular injection of Aβ in rodents, as assessed by the Morris water maze, showed an insufficient spatial learning and memory ability. However, treatment with GLP-1 analogues can improve animal performance in both aspects[8]. In addition, scientists also have found that GLP-1 and its analogues can improve memory and synaptic plasticity in the brain[9].

The functional regulation of the GLP-1 receptor is quite complex, and the receptor interacts with a variety of endogenous and exogenous polypeptides, leading to the cascade activation of multiple downstream signaling pathways. GLP-1 receptor gene polymorphism has long been found and may be associated with occurrence of obesity and diabetes mellitus[10].

The present invention has discovered the use of plasminogen in regulating GLP-1/GLP-1 receptor pathways and in treating conditions associated with GLP-1/GLP-1 receptor pathways.

SUMMARY OF THE INVENTION

The present invention relates to the following items:
1. A method for treating a disease by regulating GLP-1/GLP-1R, comprising administering an effective amount of plasminogen to a subject.
2. The method of item 1, wherein the disease is a glucose metabolism disorder-related disease, a fat metabolism disorder-related disease, or a GLP-1/GLP-1R-related nervous system disease.
3. The method of item 2, wherein the disease is one or more diseases selected from: diabetes mellitus, diabetic nephropathy, diabetic neuralgia, diabetic retinopathy, hyperlipemia, atherosclerosis, hypertension, coronary heart disease, myocardial infarction, cerebral thrombosis, cerebral hemorrhage, cerebral embolism, obesity, fatty liver, hepatic cirrhosis, osteoporosis, cognitive impairment, Parkinson's syndrome, lateral sclerosis of the spinal cord, Alzheimer's disease, inflammatory bowel disease, dyspepsia, and gastrointestinal ulcer.
4. A method for regulating GLP-1/GLP-1R function, comprising administering an effective amount of plasminogen to a subject.
5. The method of item 4, wherein the plasminogen promotes expression of GLP-1 and/or GLP-1R.
6. A method for treating a GLP-1/GLP-1R-related condition, comprising administering an effective amount of plasminogen to a subject.
7. The method of item 6, wherein the GLP-1/GLP-1R-related condition comprises one or more of: increased blood glucose, decreased glucose tolerance, increased blood lipids, obesity, fatty liver, and cognitive impairment.

8. The method of item 6, wherein the GLP-1/GLP-1R-related condition comprises one or more of: diabetes mellitus, diabetic complications, hyperlipemia, atherosclerosis, hypertension, coronary heart disease, myocardial infarction, cerebral thrombosis, cerebral hemorrhage, cerebral embolism, obesity, fatty liver, hepatic cirrhosis, osteoporosis, cognitive impairment, Parkinson's syndrome, lateral sclerosis, Alzheimer's disease, inflammatory bowel disease, dyspepsia, and gastrointestinal ulcer.

9. The method of any one of items 1 to 8, wherein the plasminogen is a protein having at least 80%, 85%, 90%, 95%, 96%, 97%, 98% or 99% sequence identity with SEQ ID No. 2, 6, 8, 10 or 12.

10. The method of any one of items 1 to 9, wherein the plasminogen is a protein that comprises a plasminogen active fragment and still has the plasminogen activity.

11. The method of item 10, wherein the plasminogen is selected from Glu-plasminogen, Lys-plasminogen, mini-plasminogen, micro-plasminogen, delta-plasminogen or their variants that retain the plasminogen activity.

12. The method of any one of items 1 to 11, wherein the plasminogen can be administered in combination with one or more other drugs or therapies.

13. The method of item 12, wherein the plasminogen can be administered in combination with one or more drugs or therapies selected from a drug or therapy for treating diabetes mellitus, a drug or therapy for treating atherosclerosis, a drug or therapy for treating cardiovascular and cerebrovascular diseases, a drug or therapy for treating thrombosis, a drug or therapy for treating hypertension, a drug or therapy for lowering blood lipids, a drug or therapy for treating fatty liver, a drug or therapy for treating Parkinson's disease, a drug or therapy for treating Alzheimer's disease, and an anti-infective drug or therapy.

14. A drug for treating a GLP-1/GLP-1R-related condition, comprising an effective amount of plasminogen.

15. An article of manufacture or kit for treating a GLP-1/GLP-1R-related condition, comprising a container containing an effective amount of plasminogen, and an instruction for use of the plasminogen to treat the GLP-1/GLP-1R-related condition.

16. The drug, article of manufacture or kit of item 14 or 15, wherein the GLP-1/GLP-1R-related condition comprises one or more of: increased blood glucose, decreased glucose tolerance, increased blood lipids, obesity, fatty liver, and cognitive impairment.

17. The drug, article of manufacture or kit of item 14 or 15, wherein the GLP-1/GLP-1R-related condition comprises one or more of: diabetes mellitus, diabetic complications, hyperlipemia, atherosclerosis, hypertension, coronary heart disease, myocardial infarction, cerebral thrombosis, cerebral hemorrhage, cerebral embolism, obesity, fatty liver, hepatic cirrhosis, osteoporosis, cognitive impairment, Parkinson's syndrome, lateral sclerosis, Alzheimer's disease, inflammatory bowel disease, dyspepsia, and gastrointestinal ulcer.

18. The use of plasminogen in the manufacture of a medicament for treating a disease by regulating GLP-1/GLP-1R.

19. The use of item 18, wherein the disease is a glucose metabolism disorder-related disease, a fat metabolism disorder-related disease, or a GLP-1/GLP-1R-related nervous system disease.

20. The use of item 19, wherein the disease is one or more diseases selected from: diabetes mellitus, diabetic nephropathy, diabetic neuralgia, diabetic retinopathy, hyperlipemia, atherosclerosis, hypertension, coronary heart disease, myocardial infarction, cerebral thrombosis, cerebral hemorrhage, cerebral embolism, obesity, fatty liver, hepatic cirrhosis, osteoporosis, cognitive impairment, Parkinson's syndrome, lateral sclerosis, Alzheimer's disease, inflammatory bowel disease, dyspepsia, and gastrointestinal ulcer.

21. The use of plasminogen in the manufacture of a medicament for regulating GLP-1/GLP-1R function.

22. The use of item 21, wherein the plasminogen promotes expression of GLP-1 and/or GLP-1R.

23. The use of plasminogen in the manufacture of a medicament for treating a GLP-1/GLP-1R-related condition.

24. The use of item 23, wherein the GLP-1/GLP-1R-related condition comprises one or more of: increased blood glucose, decreased glucose tolerance, increased blood lipids, obesity, fatty liver, and cognitive impairment.

25. The use of item 23, wherein the GLP-1/GLP-1R-related condition comprises one or more of: diabetes mellitus, diabetic complications, hyperlipemia, atherosclerosis, hypertension, coronary heart disease, myocardial infarction, cerebral thrombosis, cerebral hemorrhage, cerebral embolism, obesity, fatty liver, hepatic cirrhosis, osteoporosis, cognitive impairment, Parkinson's syndrome, lateral sclerosis, Alzheimer's disease, inflammatory bowel disease, dyspepsia, and gastrointestinal ulcer.

26. The use of any one of items 18 to 25, wherein the plasminogen is a protein having at least 80%, 85%, 90%, 95%, 96%, 97%, 98% or 99% sequence identity with SEQ ID No. 2, 6, 8, 10 or 12.

27. The use of any one of items 18 to 26, wherein the plasminogen is a protein that comprises a plasminogen active fragment and still has the plasminogen activity.

28. The use of item 27, wherein the plasminogen is selected from Glu-plasminogen, Lys-plasminogen, mini-plasminogen, micro-plasminogen, delta-plasminogen or their variants that retain the plasminogen activity.

29. The use of any one of items 18 to 28, wherein the plasminogen can be administered in combination with one or more other drugs or therapies.

30. The use of item 29, wherein the plasminogen can be administered in combination with one or more drugs or therapies selected from a drug or therapy for treating diabetes mellitus, a drug or therapy for treating atherosclerosis, a drug or therapy for treating cardiovascular and cerebrovascular diseases, a drug or therapy for treating thrombosis, a drug or therapy for treating hypertension, a drug or therapy for lowering blood lipids, a drug or therapy for treating fatty liver, a drug or therapy for treating Parkinson's disease, a drug or therapy for treating Alzheimer's disease, and an anti-infective drug or therapy.

Definition

"Diabetes mellitus" is a series of dysmetabolic syndromes of carbohydrates, proteins, fats, water, electrolytes and the like that are caused by islet hypofunction, insulin resistance and the like resulting from the effects of genetic factors, immune dysfunction, microbial infections and toxins thereof, free radical toxins, mental factors and other various pathogenic factors on the body, and is mainly characterized by hyperglycemia clinically.

"Diabetic complications" are damages to or dysfunctions of other organs or tissues of the body caused by poor blood glucose control during diabetes mellitus, including damages to or dysfunctions of the liver, kidneys, heart, retina, nervous system damage and the like. According to statistics of the World Health Organization, there are up to more than 100 diabetic complications, and diabetes mellitus is a disease currently known to have the most complications.

"Plasmin" is a very important enzyme that exists in the blood and is capable of degrading fibrin multimers.

"Plasminogen (plg)" is the zymogen form of plasmin, which is a glycoprotein composed of 810 amino acids calculated based on the amino acid sequence (SEQ ID No. 4) of the natural human plasminogen containing a signal peptide according to the sequence in the swiss prot, having a molecular weight of about 90 kD, being synthesized mainly in the liver and being capable of circulating in the blood, with the cDNA sequence that encodes this amino acid sequence is as shown in SEQ ID No. 3. Full-length PLG contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No. 1; and the amino acid sequence is as shown in SEQ ID No. 2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain[11,12]. The amino acid sequence (SEQ ID No.8) of δ-plasminogen has been reported in the literature[12], and the cDNA sequence encoding this amino acid sequence is as shown in SEQ ID No.7. Mini-plasminogen is composed of Kringle 5 and the serine protease domain, and has been reported in the literature to comprise residues Val443-Asn791 (with the Glu residue of the Glu-plg sequence that does not contain a signal peptide as the starting amino acid)[13]; the amino acid sequence is as shown in SEQ ID No. 10; and the cDNA sequence encoding this amino acid sequence is as shown in SEQ ID No. 9. In addition, micro-plasminogen comprises only the serine protease domain, the amino acid sequence of which has been reported in the literature to comprise residues Ala543-Asn791 (with the Glu residue of the Glu-plg sequence that does not contain a signal peptide as the starting amino acid)[14], and the sequence of which has been also reported in patent CN 102154253 A to comprise residues Lys531-Asn791 (with the Glu residue of the Glu-plg sequence that does not contain a signal peptide as the starting amino acid) (the sequence in this patent application refers to the patent CN 102154253 A); the amino acid sequence is as shown in SEQ ID No. 12; and the cDNA sequence encoding this amino acid sequence is as shown in SEQ ID No. 11.

In the present invention, "plasmin" is used interchangeably with "fibrinolysin" and "fibrinoclase", and the terms have the same meaning; and "plasminogen" is used interchangeably with "profibrinolysin" and "fibrinoclase zymogen", and the terms have the same meaning.

Those skilled in the art can understand that all the technical solutions of the plasminogen of the present invention are suitable for plasmin. Therefore, the technical solutions described in the present invention cover plasminogen and plasmin.

In the course of circulation, plasminogen is in a closed, inactive conformation, but when bound to thrombi or cell surfaces, it is converted into an active PLM in an open conformation under the mediation of a PLG activator (plasminogen activator, PA). The active PLM can further hydrolyze the fibrin clots to fibrin degradation products and D-dimers, thereby dissolving the thrombi. The PAp domain of PLG comprises an important determinant that maintains plasminogen in an inactive, closed conformation, and the KR domain is capable of binding to lysine residues present on receptors and substrates. A variety of enzymes that can serve as PLG activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID No.14, or an amino acid sequence having an amino acid sequence identity of at least 80%, 90%, 95%, 96%, 97%, 98% or 99% with SEQ ID No.14. Therefore, plasminogen of the present invention comprises a protein containing the plasminogen active fragment and still having the plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowry method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining. Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues); and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction $X/Y \times 100$ wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "prevention" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

2. Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the plasminogen protein of the present invention. Other microbial hosts suitable for use include *Bacillus*, for example, *Bacillus subtilis* and other species of enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda.

Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (e.g., mammalian cells cultured in cell culture in vitro) may also be used to express the plasminogen of the present invention. See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the plasminogen protein of the present invention and the like.

3. Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or non-ionic surfactants.

The formulations of the invention may also comprise one or more active compounds required for the particular disorder to be treated, preferably those that are complementary in activity and have no side effects with one another, for instance, drugs for treating one or more of the following diseases: diabetes mellitus, diabetic complications, hyperlipemia, atherosclerosis, hypertension, coronary heart disease, myocardial infarction, cerebral thrombosis, cerebral hemorrhage, cerebral embolism, obesity, fatty liver, hepatic cirrhosis, osteoporosis, cognitive impairment, Parkinson's syndrome, Alzheimer's disease, inflammatory bowel disease, dyspepsia, and gastrointestinal ulcer.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and y ethyl-L-glutamic acid (Sidman et al. Biopolymers 22:547(1983)), non-degradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(–)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms.

For example, if the aggregation mechanism is discovered to be formation of an intermolecular S—S bond through thio-disulfide interchange, stability is achieved by modifying sulfhydryl residues, lyophilizing from acidic solutions, controlling moisture content, using appropriate additives, and developing specific polymer matrix compositions.

4. Administration and Dosage

The pharmaceutical composition of the present invention can be administered in different ways, for example by intravenous, intraperitoneal, subcutaneous, intracranial, intrathecal, intraarterial (e.g., via carotid), intramuscular, intranasal, topical or intradermal administration or spinal cord or brain delivery. An aerosol preparation, such as a nasal spray preparation, comprises purified aqueous or other solutions of the active agent along with a preservative and isotonic agent. Such preparations are adjusted to a pH and isotonic state compatible with the nasal mucosa.

In some cases, the plasminogen pharmaceutical composition of the present invention may be modified or formulated in such a manner to provide its ability to cross the blood-brain barrier.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

In some embodiments, the plasminogen of the invention is formulated with an agent that promotes the plasminogen to cross the blood-brain barrier. In some cases, the plasminogen of the present invention is fused directly or via a linker to a carrier molecule, peptide or protein that promotes the fusion to cross the blood brain barrier. In some embodiments, the plasminogen of the present invention is fused to a polypeptide that binds to an endogenous blood-brain barrier (BBB) receptor. The polypeptide that is linked to plasminogen and binds to an endogenous BBB receptor promotes the fusion to cross the BBB. Suitable polypeptides that bind to endogenous BBB receptors include antibodies (e.g., monoclonal antibodies) or antigen-binding fragments thereof that specifically bind to endogenous BBB receptors. In some cases, the antibodies are encapsulated in liposomes. See, for example, US Patent Publication No. 2009/0156498.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, such as about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely and regularly.

5. Articles of manufacture or kits One embodiment of the present invention relates to an article of manufacture or a kit comprising the plasminogen of the present invention. The article of manufacture preferably comprises a container, label or package insert. Suitable containers include bottles, vials, syringes and the like. The container can be made of various materials, such as glass or plastic. The container contains a composition that is effective to treat the disease or disorder of the present invention and has a sterile access (for example, the container may be an intravenous solution bag or vial containing a plug that can be pierced by a hypodermic injection needle). At least one active agent in the composition is plasminogen. The label on or attached to the container indicates that the composition is used for treating the conditions according to the present invention. The article of manufacture may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article of manufacture comprises a package insert with instructions for use, including, for example, instructions to a user of the composition to administer the plasminogen composition and other drugs to treat an accompanying disease to a patient.

Figure 1:
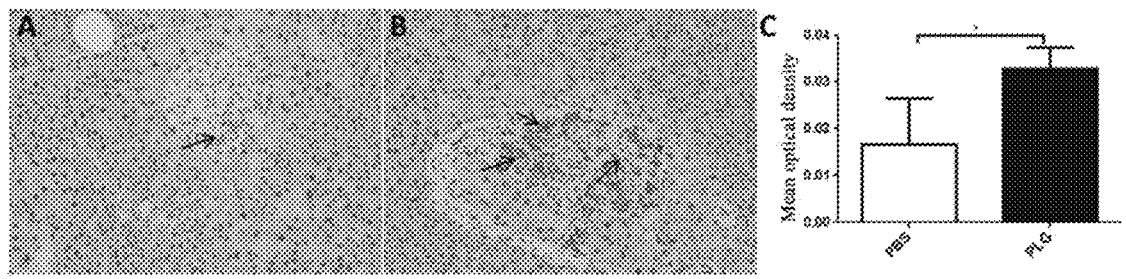
FIGS. 1A-C show the observed results of immunostaining for GLP-1 of the pancreases after administration of plasminogen to 14- to 15-week-old db/db mice for 28 days. A represents the control group administered with vehicle PBS, B represents the group administered with plasminogen, and C represents the quantitative analysis results. The results show that the expression of GLP-1 (indicated by an arrow) in the pancreatic islets of mice in the control group administered with vehicle PBS is remarkably less than that in the group administered with plasminogen, and the statistical difference is significant (* indicates P<0.05). The results indicate that plasminogen can promote expression of GLP-1 in the pancreatic islets of relatively young diabetic mice.

FIGS. 22A-D show the observed results of immunohistochemical staining for NF-κB of the pancreatic tissues after administration of plasminogen to 24- to 25-week-old diabetic mice for 31 days. A represents a normal control group, B represents the control group administered with vehicle PBS, C represents the group administered with plasminogen, and D represents the quantitative analysis results. The results show that the expression of NF-κB (indicated by arrows) in the group administered with plasminogen is similar to that in normal control mice, and is remarkably higher than that in the control group administered with vehicle PBS, and the statistical difference is significant (* indicates P<0.05). This indicates that plasminogen can promote expression of multi-directional nuclear transcription factor NF-κB, thereby promoting repair of an inflammation in the pancreatic islet of 24- to 25-week-old diabetic mice.

FIGS. 23A-D show the observed results of immunohistochemical staining for glucagon of the pancreatic islets after administration of plasminogen to 17- to 18-week-old diabetic mice for 35 days. A represents a normal control group, B represents the control group administered with vehicle PBS, C represents the group administered with plasminogen, and D represents the quantitative analysis results. The results show that glucagon is expressed in the α-cell region at the periphery of the pancreatic islet in normal control mice. Compared with the group administered with plasminogen, glucagon-positive cells (indicated by arrows) in the control group administered with vehicle PBS are remarkably increased, the glucagon-positive cells infiltrate into the central region of the pancreatic islet, and the mean optical density quantitative analysis results show that the statistical difference is extremely significant (** indicates P<0.01); and glucagon-positive cells in the group administered with plasminogen are dispersed at the periphery of the pancreatic islet, and compared with the PBS group, the morphology of the pancreatic islet in the group administered with plasminogen is closer to that of normal mice. This indicates that plasminogen can significantly inhibit proliferation of pancreatic islet α cells and secretion of glucagon, and correct the disordered distribution of pancreatic islet α cells, thus promoting repair of impaired pancreatic islets.

FIGS. 24A-D show the observed results of immunohistochemical staining for IRS-2 of the pancreatic islets after administration of plasminogen to 17- to 18-week-old diabetic mice for 35 days. A represents a normal control group, B represents the control group administered with vehicle PBS, C represents the group administered with plasminogen, and D represents the quantitative analysis results. The results show that the positive expression of IRS-2 (indicated by an arrow) in the pancreatic islets of mice in the control group administered with vehicle PBS is remarkably less than that in the group administered with plasminogen, and the statistical difference is extremely significant (** indicates P<0.01); and compared with the group administered with vehicle PBS, the expression level of IRS-2 in the group administered with plasminogen is closer to that of mice in the normal control group. This indicates that plasminogen can effectively increase expression of IRS-2 in pancreatic islet cells, improve insulin signal transduction, and reduce the pancreatic islet 13 cell injury in 17- to 18-week-old diabetic mice.

FIGS. 25A-D show the observed immunohistochemical results for IRS-2 of the pancreatic islets after administration of plasminogen to 24- to 25-week-old diabetic mice for 31 days. A represents a normal control group, B represents the control group administered with vehicle PBS, C represents the group administered with plasminogen, and D represents the quantitative analysis results. The results show that the positive expression of IRS-2 (indicated by an arrow) in the pancreatic islets of mice in the control group administered with vehicle PBS is remarkably less than that in the group administered with plasminogen, and the statistical difference is significant (* indicates P<0.05); and compared with the group administered with vehicle PBS, the expression level of IRS-2 in the group administered with plasminogen is closer to that of mice in the normal control group. This indicates that plasminogen can effectively increase expression of IRS-2 in pancreatic islet cells, improve insulin signal transduction, and reduce the pancreatic islet 13 cell injury in diabetic mice.

Figure 26:
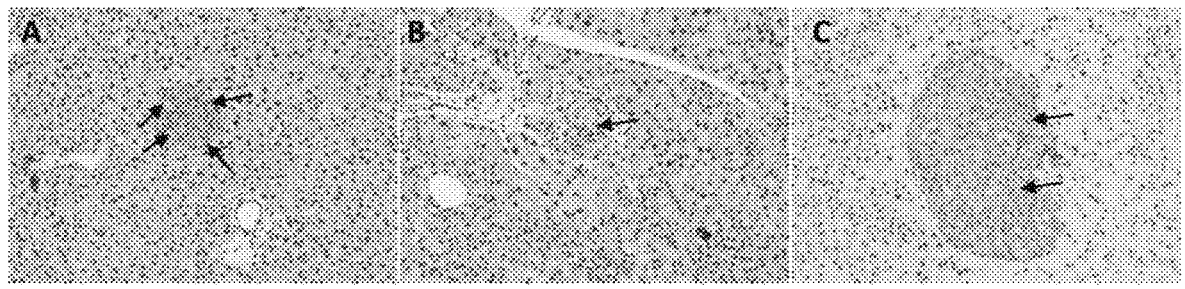

FIGS. 26A-C show the observed immunohistochemical results for IRS-2 of the pancreatic islets after administration of plasminogen to 27-week-old diabetic mice for 35 days. A represents a normal control group, B represents a control group administered with vehicle PBS, and C represents a group administered with plasminogen. The results show that the positive expression of IRS-2 (indicated by an arrow) in the pancreatic islets of mice in the control group administered with vehicle PBS is remarkably lower than that in the group administered with plasminogen, and compared with the group administered with vehicle PBS, the expression level of IRS-2 in the group administered with plasminogen is closer to that of mice in the normal control group. This indicates that plasminogen can effectively increase expression of IRS-2 in pancreatic islet cells, improve insulin signal transduction, and reduce the pancreatic islet β cell injury in diabetic mice.

Figure 27:
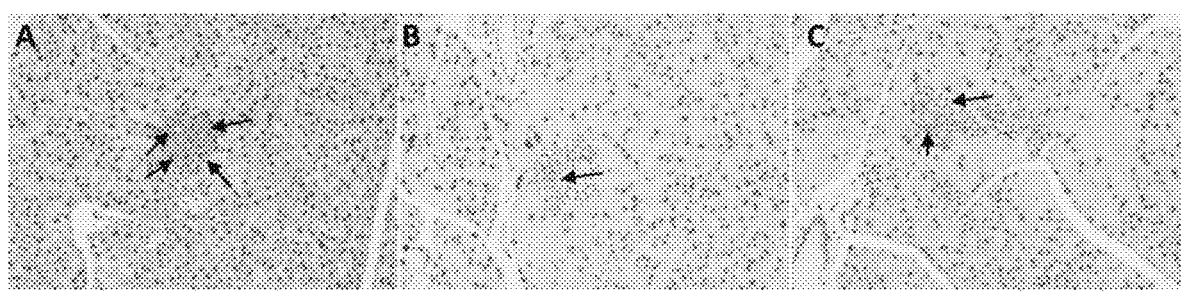

FIGS. 27A-C show the observed immunohistochemical results for IRS-2 of the pancreatic islets after administration of plasminogen to PLG$^{+/+}$ T1DM mice for 28 days. A represents a normal control group, B represents a control group administered with vehicle PBS, and C represents a group administered with plasminogen. The results show that the positive expression of IRS-2 (indicated by an arrow) in the pancreatic islets of mice in the control group administered with vehicle PBS is remarkably lower than that in the group administered with plasminogen, and compared with the group administered with vehicle PBS, the expression level of IRS-2 in the group administered with plasminogen is closer to that of mice in the normal control group. This indicates that plasminogen can effectively increase expression of IRS-2 in pancreatic islet cells, improve insulin signal transduction, and reduce the pancreatic islet β cell injury in PLG$^{+/+}$ T1DM mice.

Figure 28:
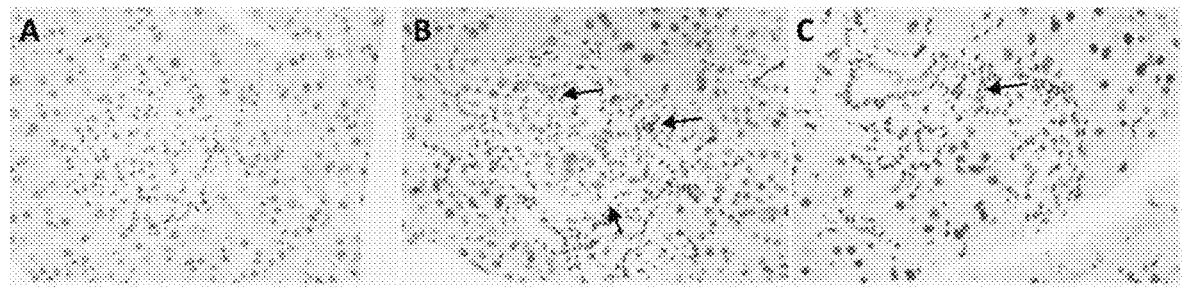

FIGS. 28A-C show the observed results of immunohistochemical staining for neutrophils in the pancreatic islets after administration of plasminogen to 27-week-old diabetic mice for 35 days. A represents a normal control group, B represents a control group administered with vehicle PBS, and C represents a group administered with plasminogen. The results show that the cells having positive expression (indicated by an arrow) in the group administered with plasminogen are less than those in the control group administered with vehicle PBS, and compared with the group administered with vehicle PBS, the result of the group administered with plasminogen is closer to that of the normal control group. This indicates that plasminogen can reduce infiltration of neutrophils.

Figure 29:
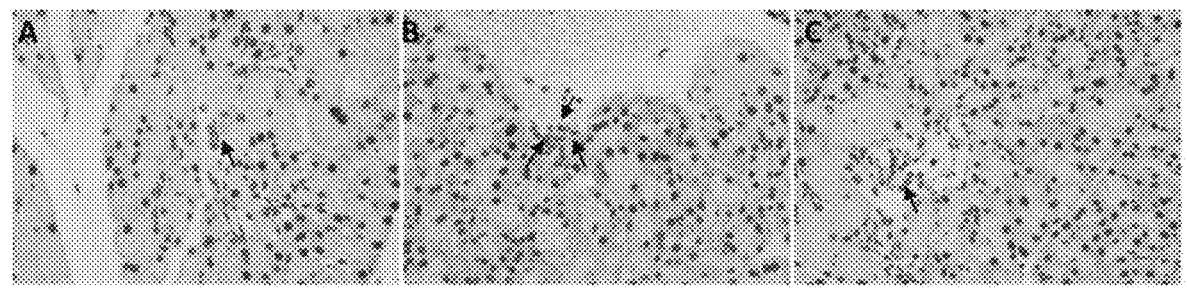

FIGS. 29A-C show the observed results of immunohistochemical staining for neutrophils in the pancreatic islets after administration of plasminogen to PLG$^{-/-}$ mice in a T1DM model for 28 days. A represents a blank control group, B represents a control group administered with vehicle PBS, and C represents a group administered with plasminogen. The results show that the cells having positive expression (indicated by an arrow) in the group administered with plasminogen are less than those in the control group administered with vehicle PBS, and compared with the group administered with vehicle PBS, the result of the group administered with plasminogen is closer to that of the blank control group. This indicates that plasminogen can reduce infiltration of neutrophils in the pancreatic islets of PLG$^{-/-}$ mice in a T1DM model.

Figure 30:
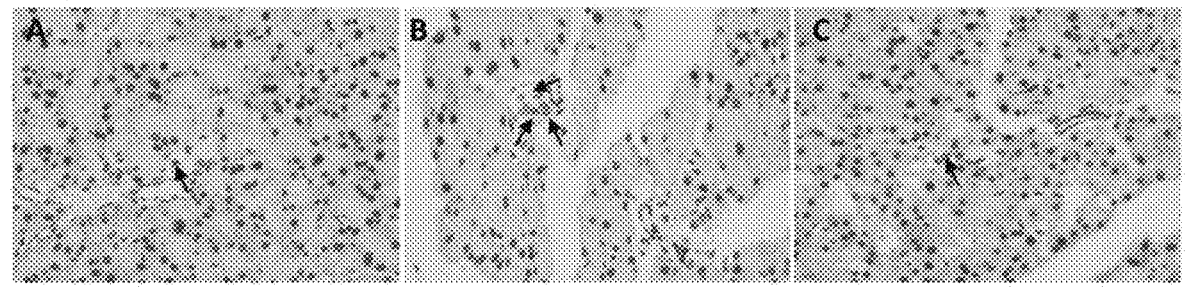

FIGS. 30A-C show the observed results of immunohistochemical staining for neutrophils in the pancreatic islets after administration of plasminogen to PLG$^{+/+}$ mice in a T1DM model for 28 days. A represents a blank control group, B represents a control group administered with vehicle PBS, and C represents a group administered with plasminogen. The results show that the cells having positive expression (indicated by an arrow) in the group administered with plasminogen are less than those in the control group administered with vehicle PBS, and compared with the group administered with vehicle PBS, the result of the group administered with plasminogen is closer to that of the blank control group. This indicates that plasminogen can reduce infiltration of neutrophils in the pancreatic islets of PLG$^{+/+}$ mice in a T1DM model.

Figure 31:
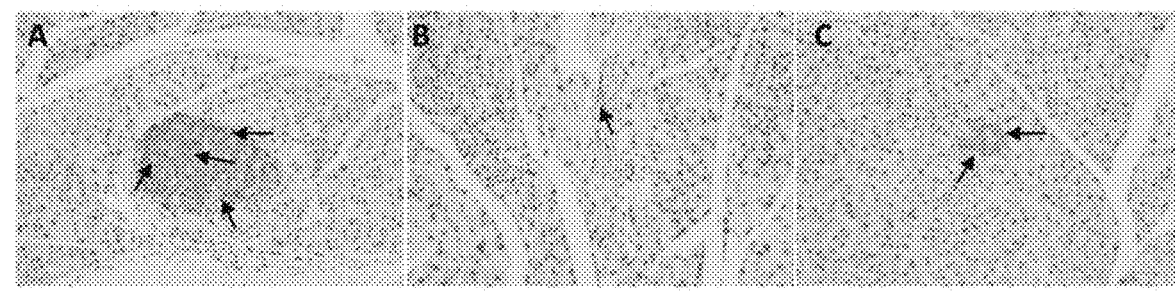

FIGS. 31A-C show the observed results of immunohistochemical staining for insulin of the pancreatic islets after administration of plasminogen to PLG$^{-/-}$ mice in a T1DM model for 28 days. A represents a blank control group, B represents a control group administered with vehicle PBS, and C represents a group administered with plasminogen. The immunohistochemical results show that the positive expression of insulin (indicated by arrows) in the group administered with plasminogen is remarkably higher than that in the control group administered with vehicle PBS, and compared with the group administered with vehicle PBS, the result of the group administered with plasminogen is closer to that of the blank control group. This indicates that plasminogen can promote synthesis and secretion of insulin in PLG$^{-/-}$ mice in a T1DM model.

Figure 32:
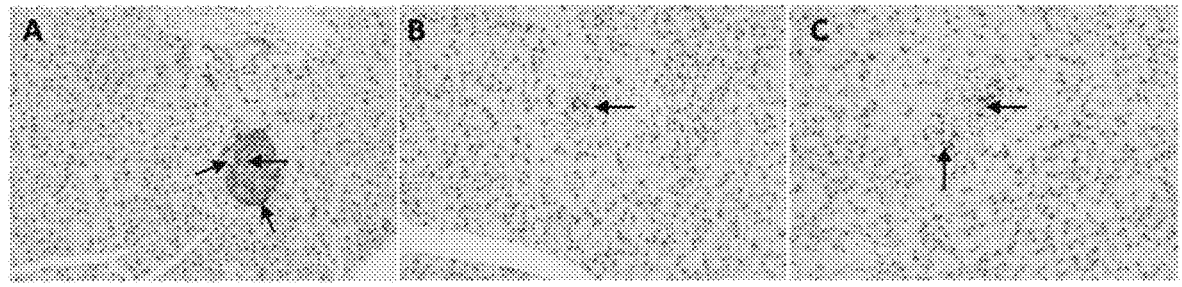

FIGS. 32A-C show the observed results of immunohistochemical staining for insulin of the pancreatic islets after administration of plasminogen to PLG$^{-/-}$ mice in a T1DM model for 28 days. A represents a blank control group, B represents a control group administered with vehicle PBS, and C represents a group administered with plasminogen. The immunohistochemical results show that the positive expression of insulin (indicated by arrows) in the group administered with plasminogen is remarkably higher than that in the control group administered with vehicle PBS, and compared with the group administered with vehicle PBS, the result of the group administered with plasminogen is closer to that of the blank control group. This indicates that plasminogen can promote synthesis and expression of insulin in PLG$^{+/+}$ mice in a T1DM model.

Figure 33:
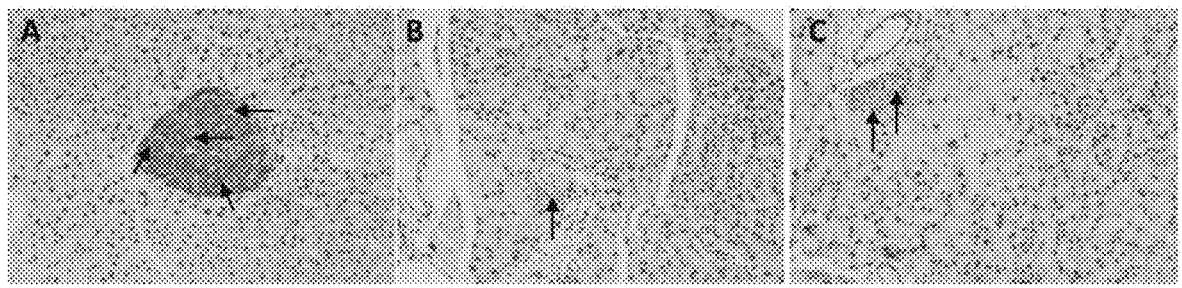

FIGS. 33A-C show the observed results of immunohistochemical staining for NF-κB of the pancreatic islets after administration of plasminogen to PLG$^{-/-}$ mice in a T1DM model for 28 days. A represents a blank control group, B represents a control group administered with vehicle PBS, and C represents a group administered with plasminogen. The results show that the expression of NF-κB (indicated by arrows) in the group administered with plasminogen is remarkably higher than that in the control group administered with vehicle PBS. This indicates that plasminogen can promote expression of inflammation repair factor NF-κB, thereby promoting repair of an inflammation in the pancreatic islet.

Figure 34:
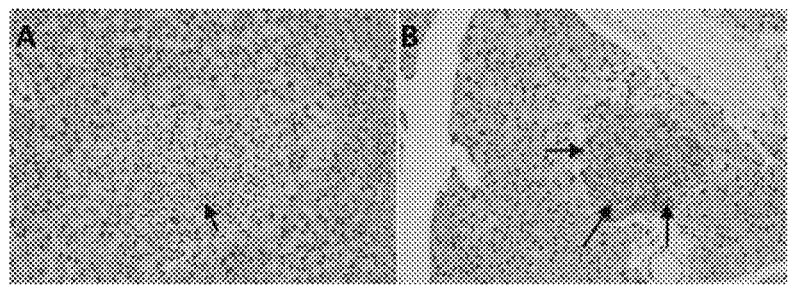

FIGS. 34A-B show the observed results of immunohistochemical staining for NF-κB of the pancreatic islets after administration of plasminogen to 17- to 18-week-old diabetic mice for 35 days. A represents the control group administered with vehicle PBS, and B represents the group administered with plasminogen. The experimental results show that the expression of NF-κB (indicated by arrows) in the group administered with plasminogen is remarkably higher than that in the control group administered with vehicle PBS. This indicates that plasminogen can promote expression of multi-directional nuclear transcription factor NF-κB, thereby promoting repair of an inflammation in the pancreatic islet of relatively young (17- to 18-week-old) diabetic mice.

Figure 35:
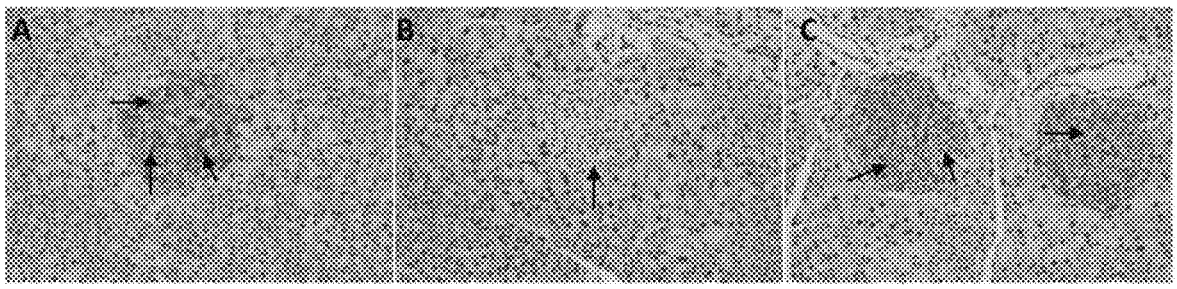

FIGS. 35A-C show the observed immunohistochemical results for NF-κB of the pancreatic islets after administration of plasminogen to 27-week-old diabetic mice for 35 days. A represents a normal control group, B represents a control group administered with vehicle PBS, and C represents a group administered with plasminogen. The results of the experiment of the present invention show that the expression of NF-κB (indicated by arrows) in the group administered with plasminogen is remarkably higher than that in the control group administered with vehicle PBS. This indicates that plasminogen can promote expression of multi-directional nuclear transcription factor NF-κB, thereby promoting repair of an inflammation in the pancreatic islet of relatively old (27-week-old) diabetic mice.

Figure 36:
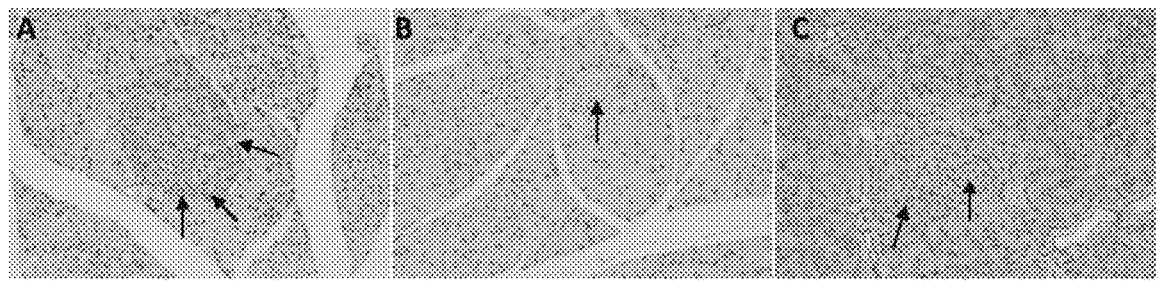

FIGS. 36A-C show the observed immunohistochemical results for TNF-α of the pancreatic islets after administration of plasminogen to 24- to 25-week-old diabetic mice for 31 days. A represents a normal control group, B represents a control group administered with vehicle PBS, and C represents a group administered with plasminogen. The research results show that the positive expression of TNF-α (indicated by arrows) in the group administered with plasminogen are remarkably higher than that in the control group administered with vehicle PBS, and compared with the group administered with vehicle PBS, the result of the group administered with plasminogen is closer to that of the normal control group. This indicates that plasminogen can promote expression of TNF-α, thereby promoting repair of impaired pancreatic islets in 24- to 25-week-old diabetic mice.

Figure 37:
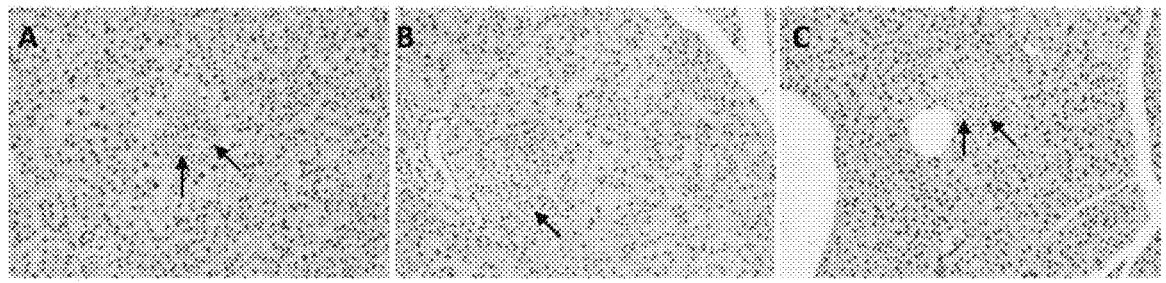

FIGS. 37A-C show the observed results of immunohistochemical staining for TNF-α of the pancreatic islets after administration of plasminogen to 27-week-old diabetic mice for 35 days. A represents a normal control group, B represents a control group administered with vehicle PBS, and C represents a group administered with plasminogen. The research results show that the positive expression of TNF-α (indicated by arrows) in the group administered with plasminogen are remarkably higher than that in the control group administered with vehicle PBS, and compared with the group administered with vehicle PBS, the result of the group administered with plasminogen is closer to that of the normal control group. This indicates that plasminogen can promote expression of TNF-α, thereby promoting repair of impaired pancreatic islets in 27-week-old diabetic mice.

Figure 38:
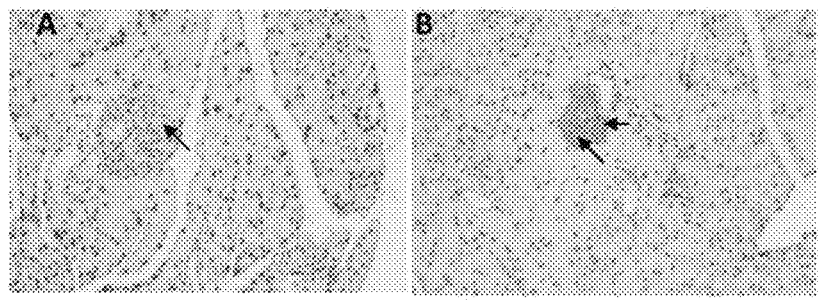

FIGS. 38A-B show the observed results of immunohistochemical staining for TNF-α of the pancreatic islets after administration of plasminogen to PLG$^{-/-}$ mice in a T1DM model for 28 days. A represents the control group administered with vehicle PBS, and B represents the group administered with plasminogen. The research results show that the positive expression of TNF-α (indicated by arrows) in the group administered with plasminogen is remarkably higher than that in the control group administered with vehicle PBS. This indicates that plasminogen can promote expression of TNF-α, thereby promoting repair of impaired pancreatic islets in PLG$^{-/-}$ mice in a T1DM model.

Figure 39:
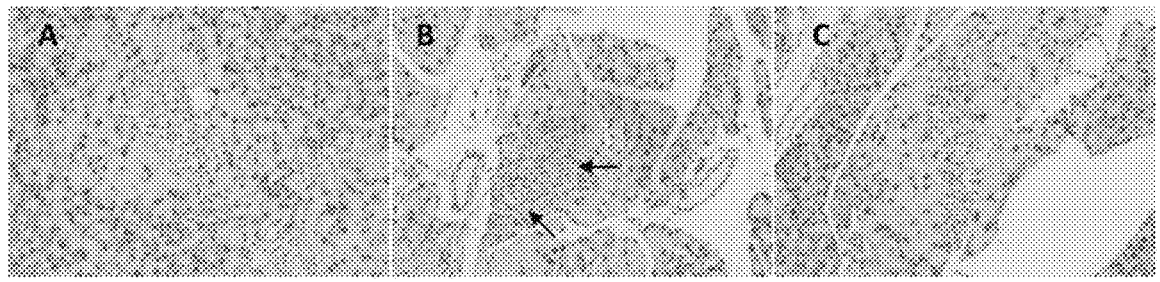

FIGS. 39A-C show the observed immunohistochemical results for IgM of the pancreatic islets after administration of plasminogen to PLG$^{-/-}$ mice in a T1DM model for 28 days. A represents a blank control group, B represents a control group administered with vehicle PBS, and C represents a group administered with plasminogen. The research results of this experiment show that the positive expression of IgM (indicated by arrows) in the group administered with plasminogen is remarkably lower than that in the control group administered with vehicle PBS, and compared with the group administered with vehicle PBS, the result of the group administered with plasminogen is closer to that of the normal control group. This indicates that plasminogen can reduce expression of IgM, thereby reducing impaired pancreatic islets in PLG$^{-/-}$ mice in a T1DM model.

Figure 40:
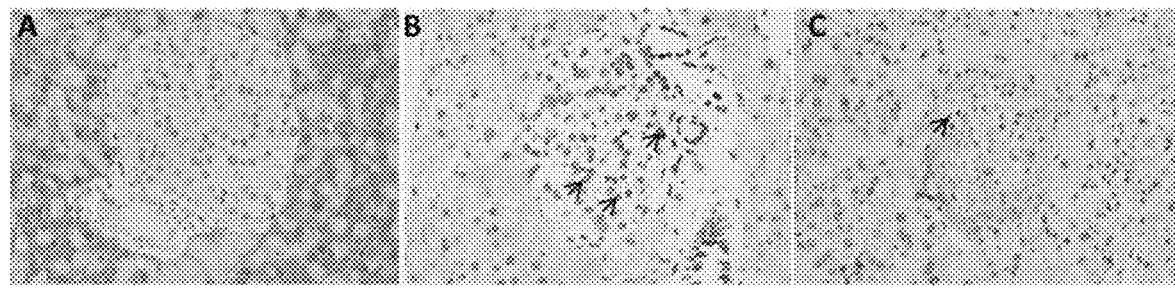

FIGS. 40A-C show the results of TUNEL staining of the pancreatic islets after administration of plasminogen to 24- to 25-week-old diabetic mice for 31 days. A represents a normal control group, B represents a control group administered with vehicle PBS, and C represents a group administered with plasminogen. The results of this experiment show that positive TUNEL staining is extremely low in the normal control group. The number of positive cells (indicated by an arrow) in the group administered with plasminogen is remarkably smaller than that in the control group administered with vehicle PBS. The apoptosis rate in the normal control group is about 8%, the apoptosis rate in the group administered with vehicle PBS is about 93%, and the apoptosis rate in the group administered with plasminogen is about 16%. This indicates that the plasminogen group can significantly reduce the apoptosis of pancreatic islet cells in diabetic mice.

Figure 41:
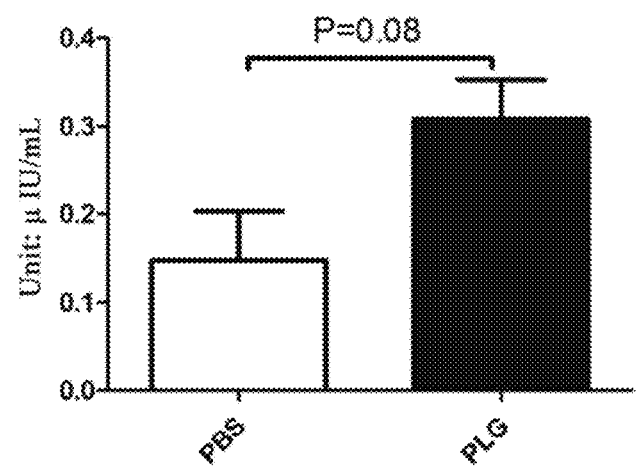

FIG. 41 shows detection results of serum insulin after administration of plasminogen to mice in a T1DM model for 20 days. The results show that the concentration of serum insulin in the mice in the control group administered with vehicle PBS is remarkably lower than that of the mice in the group administered with plasminogen, and the statistical difference is nearly significant (P=0.08). This indicates that plasminogen can promote secretion of insulin in T1DM mice.

FIGS. 42A-D show the observed results of staining for GLP-1R of the pancreatic islets after administration of plasminogen to 24- to 25-week-old diabetic mice for 31 days. A represents a normal control group, B represents the control group administered with vehicle PBS, C represents the group administered with plasminogen, and D represents the quantitative analysis results. The results show that the expression of GLP-1R (indicated by an arrow) in the pancreatic islets of mice in the control group administered with vehicle PBS is remarkably less than that in normal control mice, and although the expression of GLP-1R in the pancreatic islets of mice in the group administered with plasminogen is also less than that in the normal control group, it is remarkably more than that in the control group administered with vehicle PBS, and the statistical difference is extremely significant (* indicates P<0.05, and ** indicates P<0.01). The experimental results indicate that plasminogen can promote expression of GLP-1R in the pancreatic islets of diabetic mice.

FIGS. 43A-D show the observed results of immunostaining for GLP-1R of the pancreases after administration of plasminogen to hyperlipemia model mice for 30 days. A represents the blank control group, B represents the control group administered with vehicle PBS, C represents the group administered with plasminogen, and D represents the quantitative analysis results. The results show that the expression of GLP-1R (indicated by an arrow) in the pancreatic islets of mice in the control group administered with vehicle PBS is remarkably less than that in normal control mice, and although the expression of GLP-1R in the pancreatic islets of mice in the group administered with plasminogen is also less than that in the blank control group, it is remarkably more than that in the control group administered with vehicle PBS with an extremely significant statistical difference (** indicates P<0.01). The experimental results indicate that plasminogen can promote expression of GLP-1R in the pancreatic islets of hyperlipemia model mice.

Figure 44:
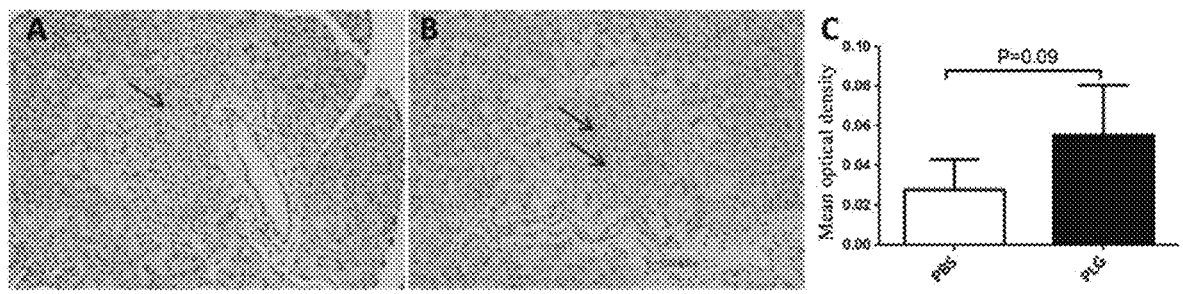

FIGS. 44A-C show the observed results of immunostaining for GLP-1R of the pancreases after administration of plasminogen to 14- to 15-week-old db/db mice for 28 days. A represents the control group administered with vehicle PBS, B represents the group administered with plasminogen, and C represents the quantitative analysis results. The results show that the expression of GLP-1R in the pancreatic islets of mice in the control group administered with vehicle PBS is remarkably less than that in the group administered with plasminogen, and the statistical difference is nearly significant (P=0.09). The results indicate that plasminogen can promote expression of GLP-1R in the pancreatic islets of relatively young (14- to 15-week-old) diabetic mice.

Figure 45:
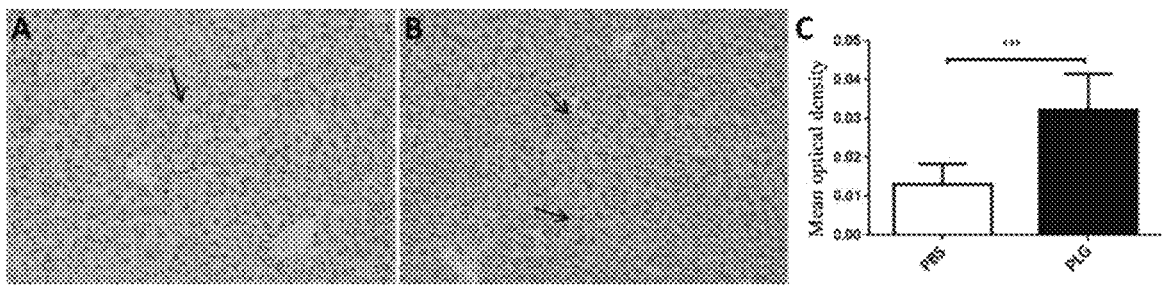

FIGS. 45A-C show the observed results of immunohistochemical staining for GLP-1R of the livers after administration of plasminogen to atherosclerosis model mice for 30 days. A represents the control group administered with vehicle PBS, B represents the group administered with plasminogen, and C represents the quantitative analysis results. The results show that the expression of GLP-1R (indicated by arrows) in the livers of mice in the group administered with plasminogen is remarkably more than that in the control group administered with vehicle PBS, and the statistical difference is extremely significant (*** indicates P<0.001). The results show that plasminogen can promote expression of GLP-1R in atherosclerosis model mice, possibly promote the synthesis, secretion, absorption or oxidation of liver fat, reduce the level of lipids in blood, and improve hyperlipemia.

Figure 46:
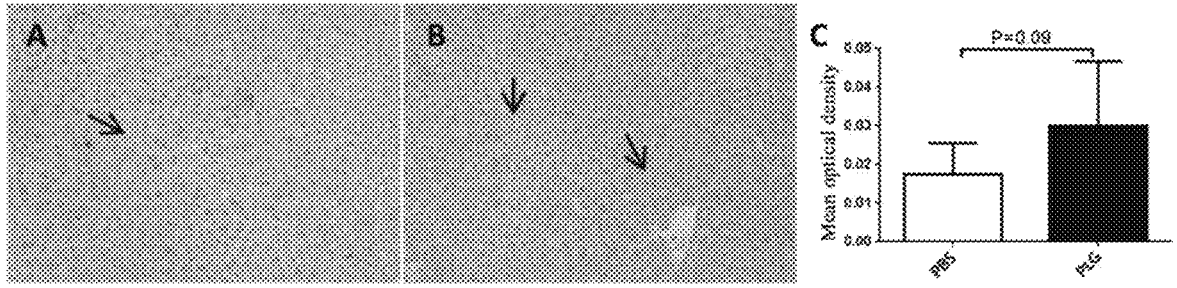

FIGS. 46A-C show representative images of immunostaining for GLP-1R of the livers after administration of plasminogen to hyperlipemia model mice for 30 days. A represents the control group administered with vehicle PBS, B represents the group administered with plasminogen, and C represents the quantitative analysis results. The results show that the expression of GLP-1R (indicated by arrows) in the livers of mice in the group administered with plasminogen is remarkably more than that in the control group administered with vehicle PBS, and the statistical difference is nearly significant (P=0.09). The results show that plasminogen can promote expression of GLP-1R in the livers of hyperlipemia model mice, possibly promote the synthesis, secretion, absorption or oxidation of liver fat, reduce the level of lipids in blood, and improve hyperlipemia.

Figure 47:
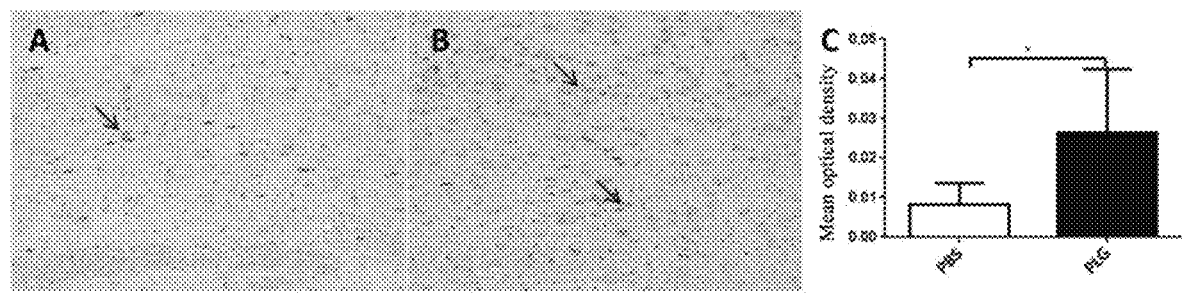

FIGS. 47A-C show the observed results of immunostaining for GLP-1R of the substantia nigra after administration of plasminogen to MPTP-induced Parkinsonian model mice for 14 days. A represents the control group administered with vehicle PBS, B represents the group administered with plasminogen, and C represents the quantitative analysis results. The results show that the expression of GLP-1R (indicated by arrows) in the substantia nigra of mice in the group administered with plasminogen is remarkably more than that in the control group administered with vehicle PBS, and the statistical difference is significant (* indicates $P<0.05$). The results indicate that plasminogen can promote expression of GLP-1R in the substantia nigra of Parkinsonian model mice.

Figure 48:
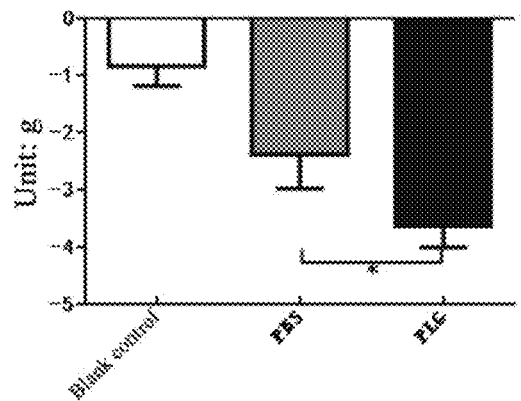

FIG. 48 shows calculation results of body weight changes after administration of plasminogen to high-calorie diet-induced obesity model mice for 28 days. The results are shown as the value of the weight on Day 29 minus the weight on Day 1. The results show that there is no significant body weight change in the blank control group, and the body weight in the group administered with plasminogen is significantly reduced than that in the control group administered with vehicle PBS with a significant statistical difference (* indicates $P<0.05$). It indicates that plasminogen can promote weight loss in obesity model mice.

Figure 49:
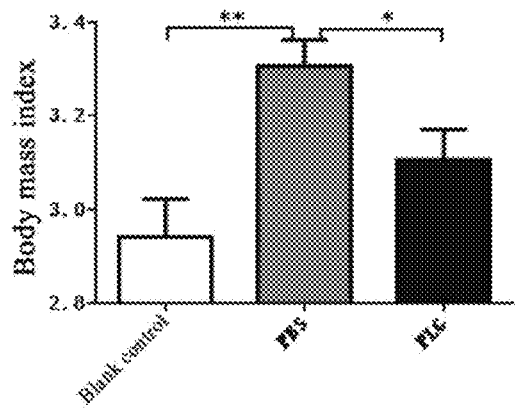

FIG. 49 shows statistical results of the body mass index after administration of plasminogen to high-calorie diet-induced obesity model mice for 28 days. The results show that the body mass index of mice in the group administered with plasminogen is remarkably lower than that in the control group administered with vehicle PBS, and the statistical difference is significant (* indicates $P<0.05$, and ** indicates $P<0.01$); and compared with the control group administered with vehicle PBS, the body mass index of mice in the group administered with plasminogen is closer to that in the blank control group. It indicates that plasminogen can significantly lower the body mass index of obesity model mice, and alleviate obesity.

Figure 50:
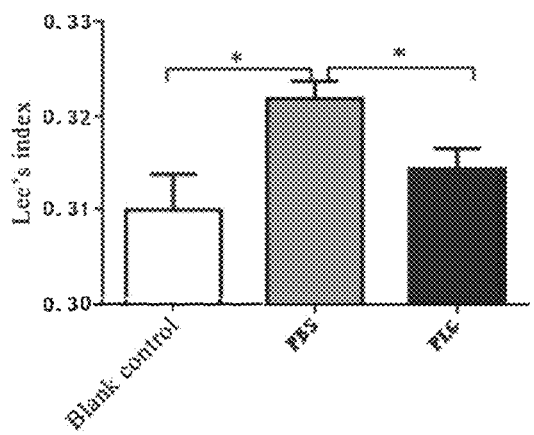

FIG. 50 shows statistical results of the Lee's index after administration of plasminogen to high-calorie diet-induced obesity model mice for 28 days. The results show that the Lee's index of mice in the group administered with plasminogen is remarkably lower than that in the control group administered with vehicle PBS, and the statistical difference is significant (* indicates $P<0.05$); and compared with the control group administered with vehicle PBS, the Lee's index of mice in the group administered with plasminogen is closer to that in the blank control group. It indicates that plasminogen can significantly lower the Lee's index of obesity model mice, and alleviate obesity.

Figure 51:
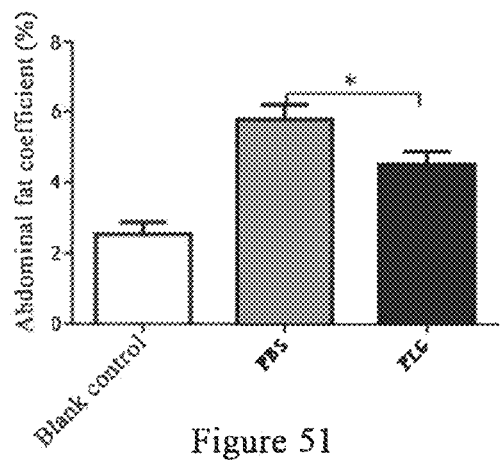

FIG. 51 shows statistical results of the abdominal fat coefficient after administration of plasminogen to high-calorie diet-induced obesity model mice for 28 days. The results show that the abdominal fat coefficient of mice in the group administered with plasminogen is remarkably lower than that in the control group administered with vehicle PBS, and the statistical difference is significant (* indicates $P<0.05$); and compared with the control group administered with vehicle PBS, the abdominal fat content of mice in the group administered with plasminogen is closer to that in the blank control group. It indicates that plasminogen can significantly reduce abdominal fat deposition in obesity model mice.

FIGS. 52A-D show statistical results of fat vacuolar area in abdominal fat by H&E staining after administration of plasminogen to high-calorie diet-induced obesity model mice for 28 days. A represents the blank control group, B represents the control group administered with vehicle PBS, C represents the group administered with plasminogen, and D represents the quantitative analysis results. The results show that the average fat vacuolar area in the group administered with plasminogen is remarkably less than that in the control group administered with vehicle PBS, and the statistical difference is extremely significant (** indicates $P<0.01$); and compared with the control group administered with vehicle PBS, the fat vacuolar area of mice in the group administered with plasminogen is closer to that in the blank control group. It indicates that plasminogen can significantly reduce the size of adipose cells and abdominal fat deposition of obesity model mice.

Figure 53:
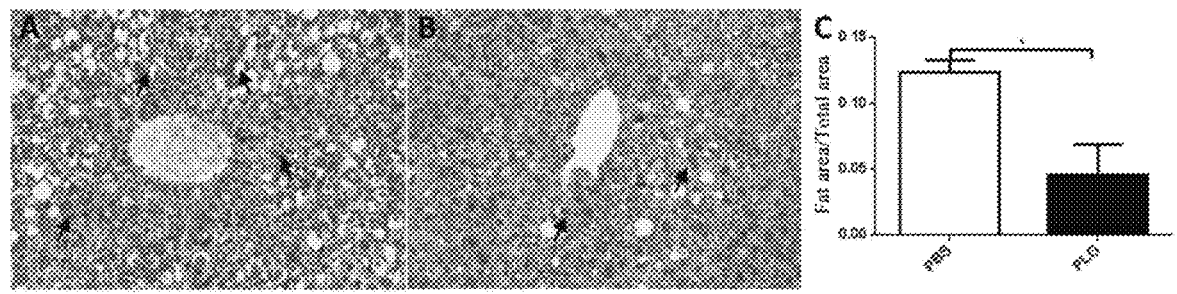

FIGS. 53A-C show images of oil red 0 staining of liver after administration of plasminogen to 24- to 25-week diabetic mice for 35 days. A represents the control group administered with vehicle PBS, B represents the group administered with plasminogen, and C represents the quantitative analysis results. The results show that the lipid deposition area in liver of mice in the group administered with plasminogen is significantly less than that in the control group administered with vehicle PBS, and the statistical difference is significant (* indicates $P<0.05$). It indicates that plasminogen can reduce fat deposition in liver of diabetic mice.

Figure 54:
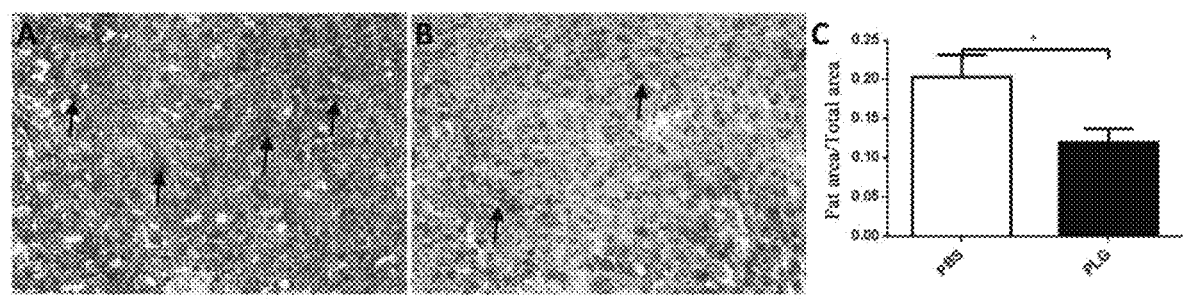

FIG. 54A-C show representative images of oil red 0 staining of liver after administration of plasminogen to ApoE atherosclerosis model mice for 30 days. A represents the control group administered with vehicle PBS, B represents the group administered with plasminogen, and C represents the quantitative analysis results. The results show that the fat deposition in liver of mice in the group administered with plasminogen is remarkably lower than that in the control group administered with vehicle PBS, and the quantitative analysis shows a significant statistical difference (* indicates $P<0.05$). It indicates that plasminogen can reduce fat deposition in liver of atherosclerosis model mice.

Figure 55:
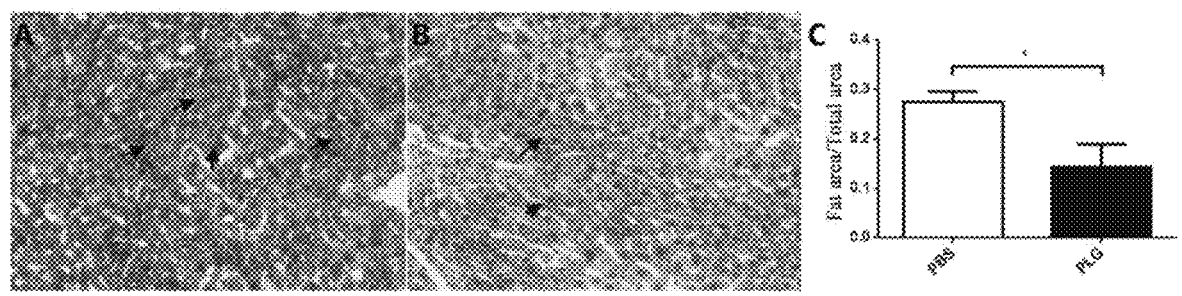
Figure 56:
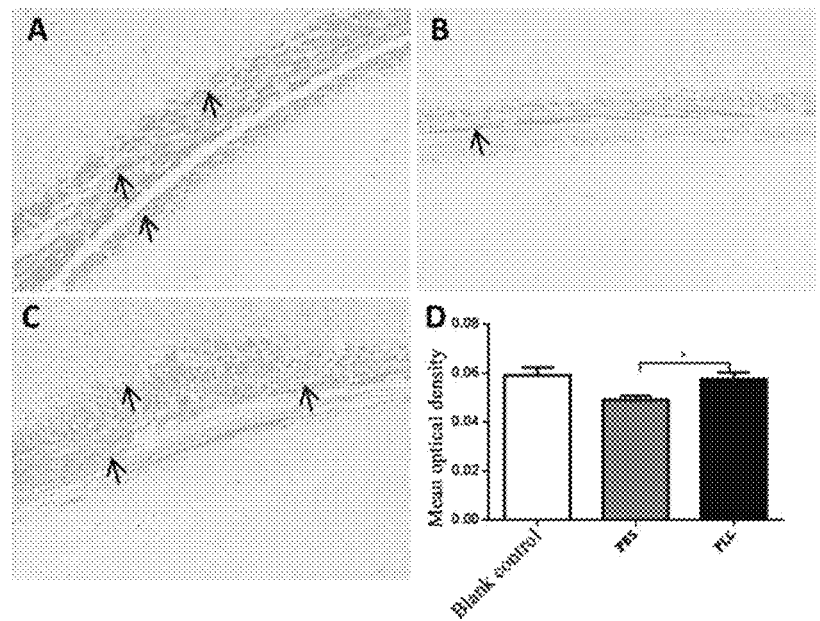

FIG. 55A-C show observed results of oil red 0 staining of liver after administration of plasminogen to 16-week hyperlipemia model mice for 30 days. A represents the control group administered with vehicle PBS, B represents the group administered with plasminogen, and C represents the quantitative analysis results. The results show that the fat deposition in liver of mice in the group administered with plasminogen is remarkably lower than that in the control group administered with vehicle PBS, and the quantitative analysis shows a significant statistical difference (* indicates $P<0.05$). It indicates that plasminogen can ameliorate fat deposition in liver of hyperlipemia model mice.

FIGS. 56A-D show the results of LFB staining for the corpus callosum after administration of plasminogen to Cuprizone-induced demyelination model mice for 14 days. A represents the blank control group, B represents the control group administered with vehicle PBS, C represents the group administered with plasminogen, and D represents the quantitative analysis results. The results show that the morphology of the medullary sheath of the corpus callosum in the blank control group is basically normal, the positive staining (indicated by arrows) of the medullary sheath of the corpus callosum in the group administered with plasminogen is remarkably more than that in the control group administered with vehicle PBS, and the statistical difference is significant (* indicates P<0.05). This indicates that plasminogen can promote regeneration of the medullary sheath of the corpus callosum in cuprizone-induced demyelination model mice.

FIGS. 57A-D show the observed results of immunostaining for brain neurofilament protein (NFP) after administration of plasminogen to Cuprizone-induced demyelination model mice for 14 days. A represents the blank control group, B represents the control group administered with vehicle PBS, C represents the group administered with plasminogen, and D represents the quantitative analysis results. The results show that the expression of NFP (indicated by arrows) in the corpus callosum of mice in the group administered with plasminogen is remarkably more than that in the control group administered with vehicle PBS, and the statistical difference is significant (* indicates P<0.05); and compared with the control group administered with vehicle PBS, the expression of NFP in the corpus callosum in the group administered with plasminogen is closer to that in the blank control group. This indicates that plasminogen can promote expression of NFP, thereby promoting the regeneration of nerve fibers.

FIGS. 58A-C show the results of immunostaining for protein gene product 9.5 (PGP 9.5) in the burned skin after administration of plasminogen to diabetic burn model mice. A is a representative image of staining for PGP 9.5. In the figures, a-c in A are representative images of the control group administered with vehicle PBS on days 4, 8 and 15, respectively, d-f are representative images of the group administered with plasminogen on days 4, 8 and 15; B is the quantitative analysis result of immunostaining on days 4 and 8 of administration; and C is the quantitative analysis result on day 15 of administration. The results show that the positive expression of PGP 9.5 in the burned skin of mice in the group administered with plasminogen is higher than that in the control group administered with vehicle PBS, and the expression of PGP 9.5 in both groups of mice is nearly significantly different on day 8 and significantly different on day 15 (* indicates P<0.05). This indicates that plasminogen can promote nerve regeneration in diabetic burned skin.

EXAMPLES

The human plasminogen used in the following examples is derived from donor plasma, and purified from plasma based on the methods described in literature[15-17] of which the processes have been optimized. The purity of plasminogen monomers is >95%.

Example 1. Plasminogen Promotes Expression of GLP-1 in Pancreatic Islet of 14- to 15-Week-Old Diabetic Mice Twelve 14- to 15-week-old male db/db mice were weighed and randomly divided into two groups based on the body weight, a group of 6 mice administered with plasminogen and a control group of 6 mice administered with vehicle PBS, on the day the experiment started that was recorded as day 0.

Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1 antibody (Wuhan Boster Biological Technology, PB0742) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Glucagon-like peptide-1 (GLP-1) is a hormone of incretin that is normally low in expression, and its expression can promote the secretion of insulin and inhibit the secretion of glucagon[18].

The results show that the expression of GLP-1 (indicated by an arrow) in the pancreatic islets of mice in the control group administered with vehicle PBS (FIG. 1A) is remarkably less than that in the group administered with plasminogen (FIG. 1B), and the statistical difference is significant (FIG. 1C) (* indicates P<0.05). The results indicate that plasminogen can promote expression of GLP-1 in the pancreatic islets of relatively young (14- to 15-week-old) diabetic mice.

Example 2. Plasminogen Promotes Expression of GLP-1 in Pancreatic Islet of 23- to 25-Week-Old Diabetic Mice Thirteen 23- to 25-week-old male db/db mice were weighed and the db/db mice were randomly divided into two groups based on the body weight, a group administered with plasminogen (7 mice) and a control group administered with vehicle PBS (6 mice), on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1 antibody (Wuhan Boster Biological Technology, PB0742) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Figure 2:
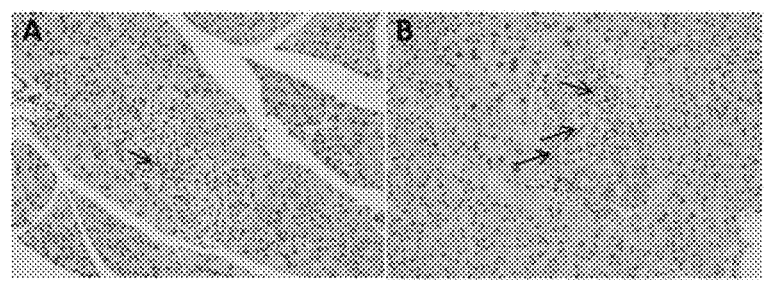
FIGS. 2A-B show representative images of immunostaining for GLP-1 of the pancreases after administration of plasminogen to 23- to 25-week-old db/db mice for 28 days. A represents the control group administered with vehicle PBS, and B represents the group administered with plasminogen. The results show that the expression of GLP-1 (indicated by an arrow) in the pancreatic islets of mice in the control group administered with vehicle PBS is remarkably less than that in the group administered with plasminogen. The results indicate that plasminogen can promote expression of GLP-1 in the pancreatic islets of relatively old diabetic mice.

The results show that the expression of GLP-1 (indicated by an arrow) in the pancreatic islets of mice in the control group administered with vehicle PBS (FIG. 2A) is remarkably less than that in the group administered with plasminogen (FIG. 2B). The results indicate that plasminogen can promote expression of GLP-1 in the pancreatic islets of relatively old (23- to 25-week-old) diabetic mice.

Example 3. Plasminogen Promotes Expression of GLP-1 in the Pancreatic Islets of PLG$^{+/+}$ Mice in a T1DM Model Eight 9- to 10-week-old male PLG$^{+/+}$ mice were randomly divided into two groups, a control group administered with vehicle PBS and a group administered with plasminogen, with 4 mice in each group. The two groups of mice were fasted for 4 hours and intraperitoneally injected with 200 mg/kg STZ (sigma S0130), in a single dose, to induce type I diabetes mellitus[19]. 12 days after the injection, administration was carried out and this day was set as administration day 1. The group administered with plasminogen was injected with human plasminogen at a dose of 1 mg/0.1 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1 (Wuhan Boster Biological Technology, PB0742) was added to the sections dropwise, incubated at 4° C. overnight, and washed with 0.01 M PBS twice for 5 minutes each time. The sections were incubated with a secondary antibody, goat anti-rabbit IgG (HRP) antibody (Abeam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Figure 3:
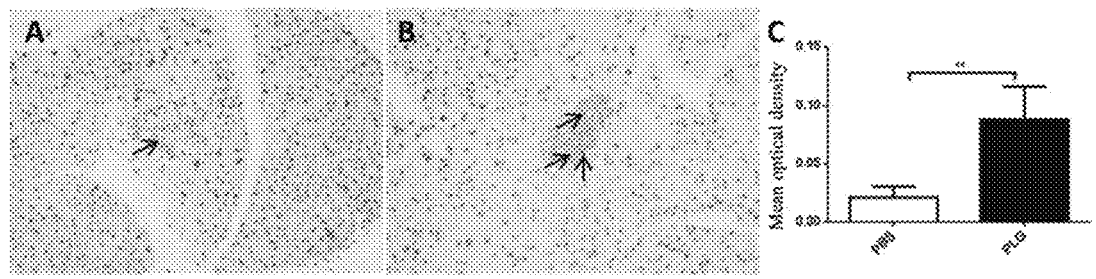
FIGS. 3A-C show the observed results of staining for GLP-1 of the pancreatic islets after administration of plasminogen to PLG$^{+/+}$ mice in a T1DM model for 28 days. A represents the control group administered with vehicle PBS, B represents the group administered with plasminogen, and C represents the quantitative analysis results. The results show that the expression of GLP-1 (indicated by arrows) in the pancreatic islets of mice in the control group administered with vehicle PBS is remarkably less than that in the group administered with plasminogen, and the statistical difference is significant (** indicates P<0.01). The results indicate that plasminogen can promote expression of GLP-1 in the pancreatic islets of mice with type I diabetes mellitus.

The results show that the expression of GLP-1 in the pancreatic islets of mice in the control group administered with vehicle PBS (FIG. 3A) is remarkably less than that in the group administered with plasminogen (FIG. 3B), and the statistical difference is significant (FIG. 3C) (** indicates P<0.01). The results indicate that plasminogen can promote expression of GLP-1 in the pancreatic islets of T1DM mice.

Example 4. Plasminogen Reduces Proliferation of Pancreatic Islet α Cells, Restores Normal Distribution of Pancreatic Islet α Cells, and Lowers Secretion of Glucagon in 24- to 25-Week-Old Diabetic Mice Eleven male db/db mice and five male db/m mice, 24-25 weeks old, were included, wherein the db/db mice were weighed and then randomly divided into two groups, a group of 5 mice administered with plasminogen and a control group of 6 mice administered with vehicle PBS, and the db/m mice were used as a normal control group. The first day of administration was set as day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein or without any liquid, both lasting for 31 consecutive days; and the mice in the normal control group were not administered. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm.

The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse glucagon antibody (Abcam, ab92517) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Pancreatic islet α cells synthesize and secrete glucagon, and are mainly distributed in the peripheral region of the pancreatic islet.

Figure 4:
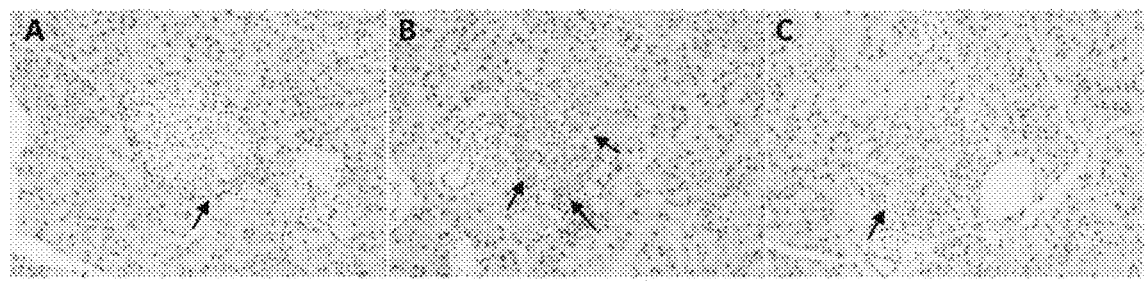
FIGS. 4A-C show the observed results of immunohistochemical staining for glucagon of the pancreatic islets after administration of plasminogen to 24- to 25-week-old diabetic mice for 35 days. A represents a normal control group, B represents a control group administered with vehicle PBS, and C represents a group administered with plasminogen. The results show that glucagon is expressed in the α-cell region at the periphery of the pancreatic islet in normal control mice. Compared with the group administered with plasminogen, glucagon-positive cells (indicated by arrows) in the control group administered with vehicle PBS are remarkably increased, and the positive cells infiltrate into the central region of the pancreatic islet; and glucagon-positive cells in the group administered with plasminogen are dispersed at the periphery of the pancreatic islet, and compared with the PBS group, the morphology of the pancreatic islet in the group administered with plasminogen is closer to that of normal mice. This indicates that plasminogen can significantly inhibit proliferation of pancreatic islet α cells and secretion of glucagon, and correct the disordered distribution of pancreatic islet α cells, thus promoting repair of impaired pancreatic islets.

The results show that compared with the group administered with plasminogen (FIG. 4C), glucagon-positive cells (indicated by arrows) in the control group administered with vehicle PBS (FIG. 4B) are remarkably increased, and the positive cells infiltrate into the central region of the pancreatic islet; and glucagon-positive cells in the group administered with plasminogen are dispersed at the periphery of the pancreatic islet, and compared with the group administered with vehicle PBS, the morphology of the pancreatic islet in the group administered with plasminogen is closer to that in the normal control group (FIG. 4A). This indicates that plasminogen can significantly inhibit proliferation of pancreatic islet α cells and secretion of glucagon, and correct the disordered distribution of pancreatic islet α cells in 24- to 25-week-old diabetic mice, suggesting that plasminogen can promote repair of impaired pancreatic islets.

Example 5. Plasminogen Inhibits Proliferation of Pancreatic Islet α Cells, Restores Normal Distribution of Pancreatic Islet α Cells, and Lowers Secretion of Glucagon in 27-Week-Old Diabetic Mice Nine male db/db mice and three male db/m mice, 27 weeks old, were included, wherein the db/db mice were weighed and then randomly divided into two groups, a group of 4 mice administered with plasminogen and a control group of 5 mice administered with vehicle PBS, and the db/m mice were used as a normal control group. The first day of administration was set as day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days; and the mice in the normal control group were not administered. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse glucagon antibody (Abcam, ab92517) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Pancreatic islet α cells synthesize and secrete glucagon, and are mainly distributed in the peripheral region of the pancreatic islet.

Figure 5:
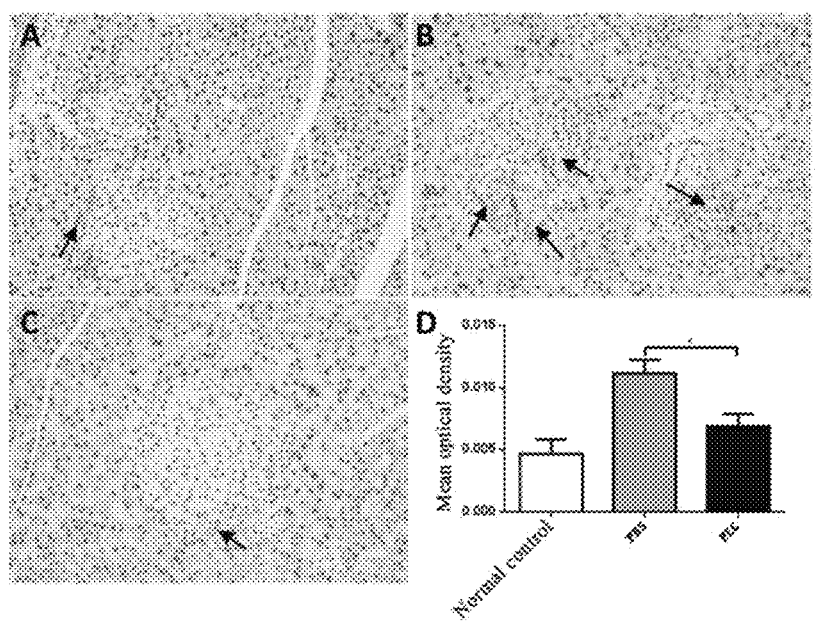
FIGS. 5A-D show the observed results of immunohistochemical staining for glucagon of the pancreatic islets after administration of plasminogen to 27-week-old diabetic mice for 35 days. A represents a normal control group, B represents the control group administered with vehicle PBS, C represents the group administered with plasminogen, and D represents the quantitative analysis results. The results show that glucagon is expressed in the α-cell region at the periphery of the pancreatic islet in normal control mice. Compared with the group administered with plasminogen, positive cells (indicated by arrows) in the control group administered with vehicle PBS are remarkably increased, the glucagon-positive cells infiltrate into the central region of the pancreatic islet, and the mean optical density quantitative analysis results show a statistical difference (* indicates P<0.05); and glucagon-positive cells in the group administered with plasminogen are dispersed at the periphery of the pancreatic islet, and compared with the PBS group, the morphology of the pancreatic islet in the group administered with plasminogen is closer to that of normal mice. This indicates that plasminogen can significantly inhibit proliferation of pancreatic islet α cells and secretion of glucagon, and correct the disordered distribution of pancreatic islet α cells, thus promoting repair of impaired pancreatic islets.

The results show that compared with the group administered with plasminogen (FIG. 5C), glucagon-positive cells (indicated by arrows) in the control group administered with vehicle PBS (FIG. 5B) are remarkably increased, the positive cells infiltrate into the central region of the pancreatic islet, and the mean optical density quantitative analysis results show a statistical difference (* indicates P<0.05) (FIG. 5D); and glucagon-positive cells in the group administered with plasminogen are dispersed at the periphery of the pancreatic islet, and compared with the group administered with vehicle PBS, the morphology of the pancreatic islet in the group administered with plasminogen is closer to that in the normal control group (FIG. 5A). This indicates that plasminogen can significantly inhibit proliferation of pancreatic islet α cells and secretion of glucagon, and correct the disordered distribution of pancreatic islet α cells in 27-week-old diabetic mice, suggesting that plasminogen can promote repair of impaired pancreatic islets.

Example 6. Plasminogen Reduces Secretion of Glucagon in PLG$^{+/+}$ Mice in a T1DM Model Fifteen 9- to 10-week-old male PLG$^{+/+}$ mice were randomly divided into two groups based on the body weight, a blank control group (5 mice) and a model group (10 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS and a group administered with plasminogen, with 5 mice in each group.

After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse glucagon antibody (Abcam, ab92517) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA).

After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×. Pancreatic islet α cells synthesize and secrete glucagon, which is mainly distributed in the peripheral region of the pancreatic islet.

Figure 6:
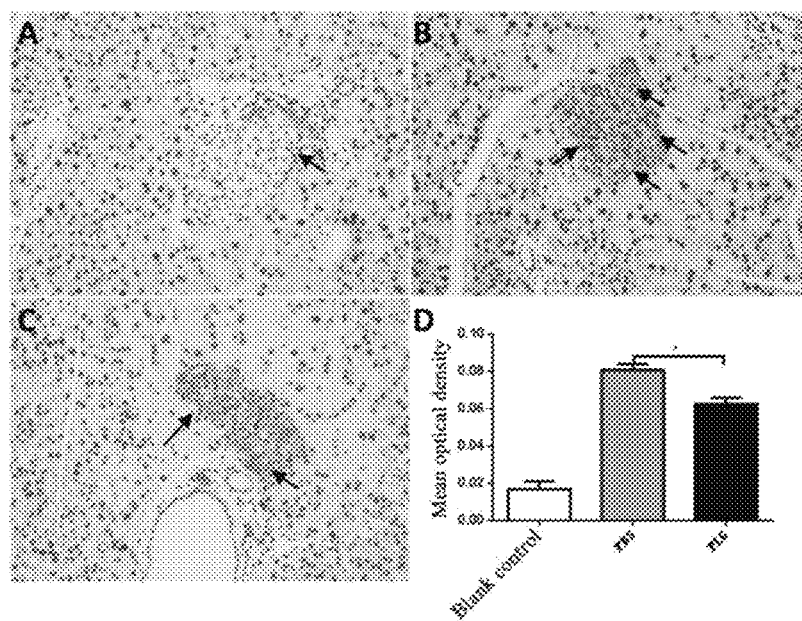
FIGS. 6A-D show the observed results of immunohistochemical staining for glucagon of the pancreatic islets after administration of plasminogen to PLG$^{+/+}$ mice in a T1DM model for 28 days. A represents the blank control group, B represents the control group administered with vehicle PBS, C represents the group administered with plasminogen, and D represents the quantitative analysis results. The results show that the positive expression of glucagon in the control group administered with vehicle PBS is remarkably higher than that in the group administered with plasminogen, and the mean optical density quantitative analysis results show that the statistical difference is significant (* indicates P<0.05). This indicates that plasminogen can significantly reduce the secretion of glucagon from pancreatic islet α cells in diabetic mice and promote repair of impaired pancreatic islets.

The results show that the positive expression of glucagon (indicated by arrows) in the control group administered with vehicle PBS (FIG. 6B) is remarkably higher than that in the group administered with plasminogen (FIG. 6C), and the mean optical density quantitative analysis results show that the statistical difference is significant (* indicates P<0.05) (FIG. 6D); in addition, compared with the group administered with vehicle PBS, the result of the group administered with plasminogen is closer to that of the blank control group (FIG. 6A). This indicates that plasminogen can significantly reduce secretion of glucagon from pancreatic islet α cells in STZ-induced T1DM mice.

Example 7. Plasminogen Lowers Blood Glucose in Diabetic Mice

Eight 24- to 25-week-old male db/db mice were randomly divided into two groups, a group of 5 mice administered with plasminogen, and a control group of 3 mice administered with vehicle PBS. The mice were weighed and grouped on the day when the experiment began, i.e. day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. After fasting for 16 hours on days 10 and 31, blood glucose testing was carried out using a blood glucose test paper (Roche, Mannheim, Germany) on days 11 and 32.

Figure 7:
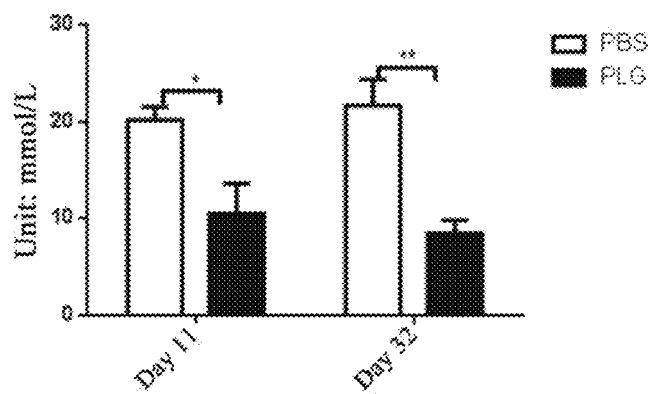
FIG. 7 shows the detection results of blood glucose on days 11 and 32 of administration of plasminogen to 24- to 25-week-old diabetic mice. The results show that the blood glucose level in mice in the group administered with plasminogen was remarkably lower than that in the control group administered with vehicle PBS, and the statistical difference was significant (* indicates P<0.05, and ** indicates P<0.01). In addition, with the prolongation of the administration time, the blood glucose level of the mice in the control group administered with vehicle PBS has a tendency to rise, while the blood glucose level of the group administered with plasminogen gradually decreases. This indicates that plasminogen has a hypoglycemic effect.

The results show that the blood glucose level in mice in the group administered with plasminogen was remarkably lower than that in the control group administered with vehicle PBS, and the statistical difference was significant (* indicates $P<0.05$, and ** indicates $P<0.01$). In addition, with the prolongation of the administration time, the blood glucose level of the mice in the control group administered with vehicle PBS has a tendency to rise, whereas the blood glucose level of the group administered with plasminogen gradually decreases (FIG. 7). This indicates that plasminogen has an effect of reducing blood glucose in diabetic animals.

Example 8. Plasminogen Lowers Fructosamine Level in Diabetic Mice

For five 24- to 25-week-old male db/db mice, 50 μl of blood was collected from venous plexus in the eyeballs of each mouse one day before administration, recorded as day 0, for detecting a concentration of serum fructosamine; starting from the 1st day, plasminogen was administered, and human plasminogen was injected at a dose of 2 mg/0.2 mL/mouse/day via the tail vein for 31 consecutive days. On day 32, blood was taken from the removed eyeballs to detect the concentration of serum fructosamine. The concentration of fructosamine was measured using a fructosamine detection kit (A037-2, Nanjing Jiancheng).

Figure 8:
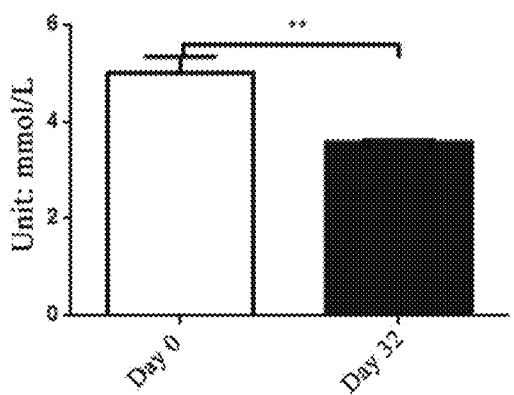
FIG. 8 shows the effect of administration of plasminogen on the concentration of serum fructosamine in diabetic mice. The detection results show that the concentration of serum fructosamine is remarkably decreased after administration of plasminogen, and as compared with that before administration, the statistical difference is extremely significant (** indicates P<0.01). This indicates that plasminogen can significantly reduce the serum fructosamine level in diabetic mice.

The concentration of fructosamine reflects the average level of blood glucose within 1 to 3 weeks. The results show that the concentration of serum fructosamine is remarkably decreased after administration of plasminogen, and as compared with that before administration, the statistical difference is extremely significant (** indicates $P<0.01$) (FIG. 8). This indicates that plasminogen can effectively reduce the serum fructosamine level in diabetic animals.

Example 9. Plasminogen Lowers Serum Fructosamine Level in 27-Week-Old Diabetic Mice Nine 27-week-old male db/db mice were weighed and randomly divided into two groups based on the body weight, a group of 4 mice administered with plasminogen and a control group of 5 mice administered with vehicle PBS, on the day the experiment started that was recorded as day 0. The group administered with plasminogen was injected with human plasminogen at a dose of 2 mg/0.2 mL/mouse/day via the tail vein, and the control group administered with vehicle PBS was injected with an equal volume of PBS via the tail vein. Plasminogen or PBS was administered to the mice from Day 1 for 35 consecutive days. On day 36, the mice were sacrificed to detect the concentration of serum fructosamine. The concentration of fructosamine was measured using a fructosamine detection kit (A037-2, Nanjing Jiancheng).

Figure 9:
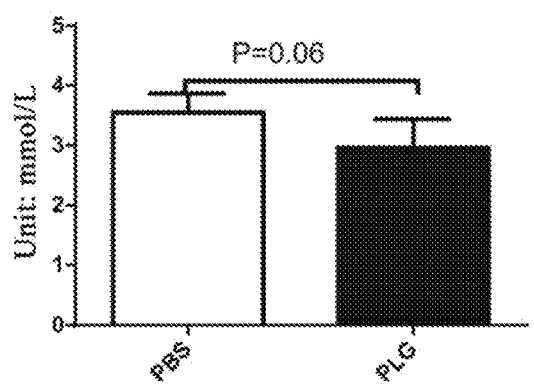
FIG. 9 shows detection results of serum fructosamine after administration of plasminogen to 27-week-old diabetic mice for 35 days. The detection results show that the concentration of serum fructosamine in the group administered with plasminogen is remarkably lower than that in the control group administered with vehicle PBS, and the statistical difference is nearly significant (P=0.06). This indicates that plasminogen can significantly reduce the serum fructosamine level in diabetic mice.

The detection results show that the concentration of serum fructosamine in the group administered with plasminogen is remarkably lower than that in the control group administered with vehicle PBS, and the statistical difference is nearly significant ($P=0.06$) (FIG. 9). This indicates that plasminogen can reduce concentration of serum fructosamine in 27-week-old diabetic mice.

Example 10. Plasminogen Lowers Glycated Hemoglobin Level in Diabetic Mice

Nine 27-week-old male db/db mice were weighed and then randomly divided into two groups based on the body weight, a group of 4 mice administered with plasminogen, and a control group of 5 mice administered with vehicle PBS. After grouping, the first day of administration was set as day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 35, the mice were fasted for 16 hours, and on day 36, the blood was taken from removed eyeballs for detecting the concentration of plasma glycated hemoglobin.

The content of glycated hemoglobin can generally reflect the control of blood glucose in a patient within recent 8 to 12 weeks.

Figure 10:
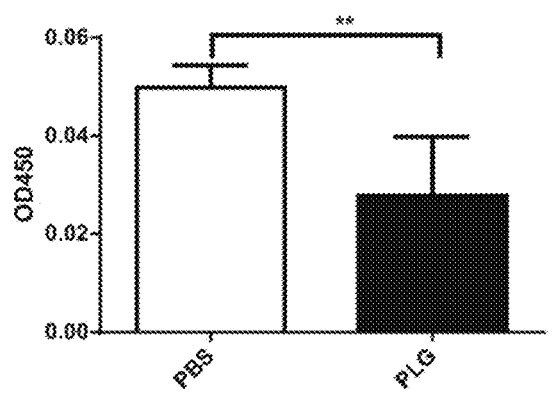
FIG. 10 shows detection results of plasma glycated hemoglobin after administration of plasminogen to 27-week-old diabetic mice for 35 days. The results show that the OD value of glycated hemoglobin in the mice in the group administered with plasminogen is remarkably lower than that in the control group administered with vehicle PBS, and the statistical difference is extremely significant (** indicates P<0.01). This indicates that plasminogen has an effect of reducing plasma glycated hemoglobin in diabetic mice.

The results show that the OD value of glycated hemoglobin in the mice in the group administered with plasminogen is remarkably lower than that in the control group administered with vehicle PBS, and the statistical difference is extremely significant (** indicates $P<0.01$) (FIG. 10). This indicates that plasminogen has an effect of reducing plasma glycated hemoglobin in diabetic mice.

Example 11. Plasminogen Improves Glucose Tolerance of Diabetic Mice

Nine 27-week-old male db/db mice and three db/m mice were included. The db/db mice were weighed and then randomly divided into two groups based on the body weight, a group of 4 mice administered with plasminogen and a control group of 5 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 10 consecutive days; and the normal control mice were not administered. On day 11, after the mice were fasted for 16 hours, each mouse was intraperitoneally injected with 5% glucose solution at 5 g/kg body weight, and the concentration of blood glucose was detected 0, 30, 60, 90, 120, and 180 minutes using a blood glucose test paper (Roche, Mannheim, Germany).

An intraperitoneal glucose tolerance test (IPGTT) can detect the tolerance of a body to glucose. It is known in the prior art that the glucose tolerance of a diabetic patient is decreased.

Figure 11:
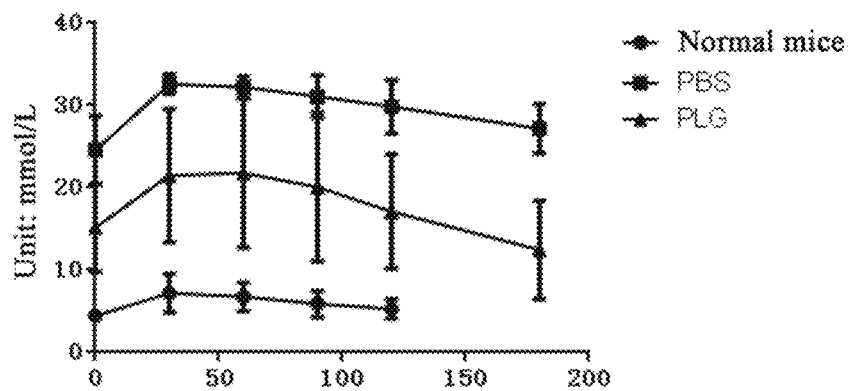
FIG. 11 shows detection results of IPGTT after administration of plasminogen to 27-week-old diabetic mice for 10 days. The results show that after intraperitoneal injection of glucose, the blood glucose level of the mice in the group administered with plasminogen is lower than that in the control group administered with vehicle PBS, and compared with the control group administered with vehicle PBS, the glucose tolerance curve of the group administered with plasminogen is closer to that of the normal mice group. This indicates that plasminogen can remarkably improve the glucose tolerance of diabetic mice.

The experimental results show that after intraperitoneal injection of glucose, the blood glucose level of the mice in the group administered with plasminogen is lower than that in the control group administered with vehicle PBS, and compared with the control group administered with vehicle PBS, the glucose tolerance curve of the group administered with plasminogen is closer to that of the normal mice group (FIG. 11). This indicates that plasminogen can remarkably improve the glucose tolerance of diabetic mice.

Example 12. Plasminogen Reduces Blood Glucose Level in $PLG^{+/+}$ Mice in a T1DM Model Ten 9- to 10-week-old male $PLG^{+/+}$ mice were randomly divided into two groups, a control group administered with vehicle PBS and a group administered with plasminogen, with 5 mice in each group. The two groups of mice were fasted for 4 hours and intraperitoneally injected with 200 mg/kg streptozotocin (STZ) (Sigma S0130), in a single dose, to induce T1DM[19]. 12 days after the injection of STZ, administration was carried out and this day was recorded as administration day 1. The group administered with plasminogen was injected with human plasminogen at a dose of 1 mg/0.1 mL/mouse/day via the tail vein, and the control group administered with vehicle PBS was injected with an equal volume of PBS via the tail vein, both lasting for 10 consecutive days. On day 11, after the mice were fasted for 6 hours, blood glucose testing was carried out using a blood glucose test paper (Roche, Mannheim, Germany).

Figure 12:
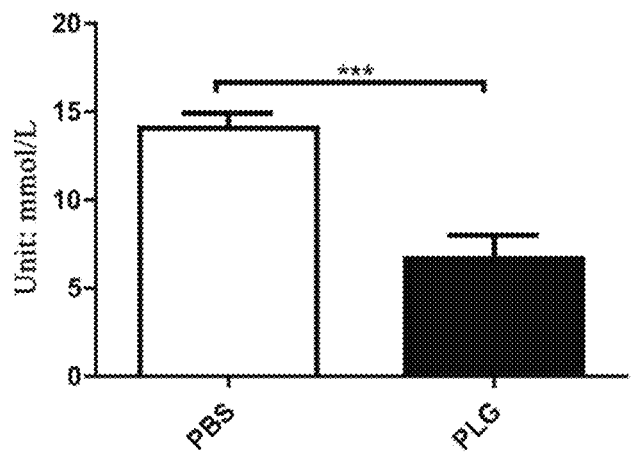
FIG. 12 shows the detection results of post-fasting blood glucose after administration of plasminogen to PLG$^{+/+}$ mice in a T1DM model for 10 days. The results show that the blood glucose level of the mice in the control group administered with vehicle PBS is remarkably higher than that in the group administered with plasminogen, and the statistical difference is extremely significant (*** indicates P<0.001). This indicates that plasminogen can significantly reduce the blood glucose level in PLG$^{+/+}$ mice in a T1DM model.

The results show that the blood glucose level of the mice in the control group administered with vehicle PBS is remarkably higher than that of the mice in the group administered with plasminogen, and the statistical difference is extremely significant (*** indicates P<0.001) (FIG. 12). This indicates that plasminogen can significantly reduce the blood glucose level in $PLG^{+/+}$ mice in a T1DM model.

Example 13. Plasminogen Improves Glucose Tolerance of T1DM Model Mice

Fifteen 9- to 10-week-old male $PLG^{+/+}$ mice were randomly divided into two groups based on the body weight, a blank control group (5 mice) and a model group (10 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS and a group administered with plasminogen, with 5 mice in each group. After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 28, after the mice were fasted for 6 hours, 5% glucose solution was intraperitoneally injected at 5 g/kg body weight, and the concentration of blood glucose was detected 0, 15, 30, 60, and 90 minutes after the injection using a blood glucose test paper (Roche, Mannheim, Germany).

An intraperitoneal glucose tolerance test (IPGTT) can detect the tolerance of a body to glucose. It is known in the prior art that the glucose tolerance of a diabetic patient is decreased.

Figure 13:
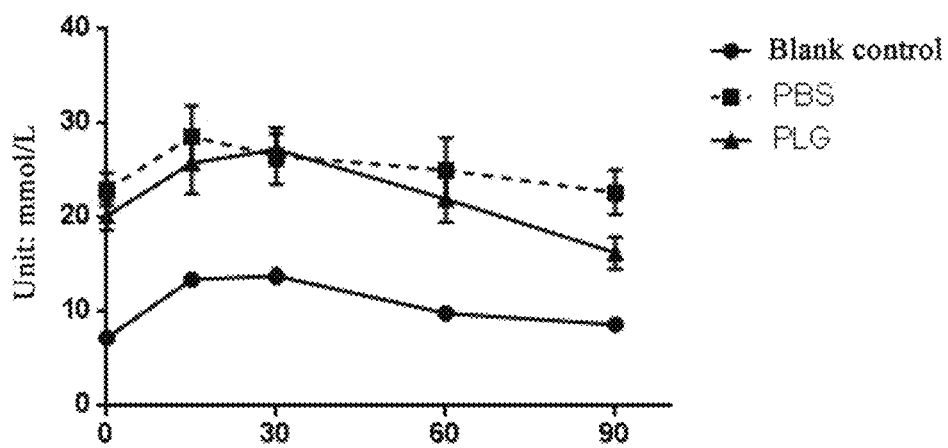
FIG. 13 shows the detection results of IPGTT after administration of plasminogen to PLG$^{+/+}$ mice in a T1DM model for 28 days. The results show that after injection of glucose, the blood glucose concentration of the mice in the control group administered with vehicle PBS is remarkably higher than that in the group administered with plasminogen, and compared with the control group administered with vehicle PBS, the glucose tolerance curve of the group administered with plasminogen is closer to that of normal mice. This indicates that plasminogen can increase the glucose tolerance of PLG$^{+/+}$ mice in a T1DM model.

The results show that after injection of glucose, the blood glucose concentration of the mice in the control group administered with vehicle PBS is remarkably higher than that in the group administered with plasminogen, and compared with the control group administered with vehicle PBS, the glucose tolerance curve of the group administered with plasminogen is closer to that of normal mice (FIG. 13). This indicates that plasminogen can increase the glucose tolerance of $PLG^{+/+}$ mice in a T1DM model.

Example 14. Plasminogen Enhances Glucose Decomposing Ability of T1DM Model Mice

Eight 9- to 10-week-old male C57 mice were randomly divided into two groups, a control group administered with vehicle PBS and a group administered with plasminogen, with 4 mice in each group. The mice in the group administered with vehicle PBS and the group administered with plasminogen were fasted for 4 hours and then intraperitoneally injected with streptozotocin (STZ) (Sigma S0130) at 200 mg/kg body weight, in a single dose, to induce T1DM[19]. 12 days after the injection of STZ, administration was carried out and this day was set as administration day 1. The group administered with plasminogen was injected with human plasminogen at a dose of 1 mg/0.1 mL/mouse/day via the tail vein, and the control group administered with vehicle PBS was injected with an equal volume of PBS via the tail vein. Administration was carried out for 19 consecutive days. On day 20, after the mice were fasted for 6 hours, 20% glucose was intragastrically administered at 2 g/kg body weight, and after 60 minutes, blood was collected from the orbital venous plexus and centrifuged to obtain a supernatant, which was detected for blood glucose by means of a glucose detection kit (Rongsheng, Shanghai, 361500).

Figure 14:
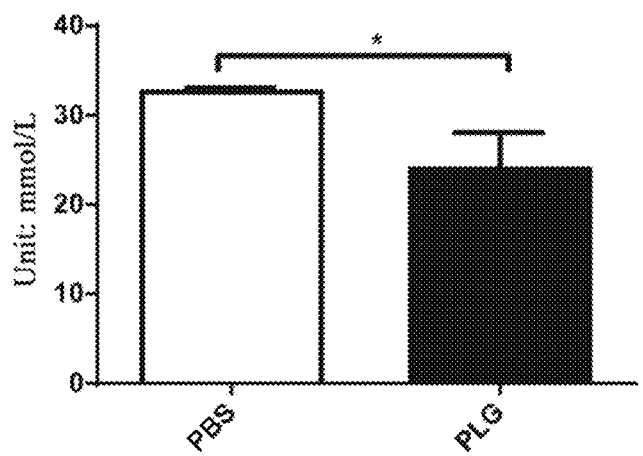
FIG. 14 shows detection results of blood glucose after administration of plasminogen to mice in a T1DM model for 20 days. The results show that the blood glucose level of the mice in the control group administered with vehicle PBS is remarkably higher than that of the mice in the group administered with plasminogen, and the statistical difference is significant (P=0.04). This indicates that plasminogen can promote the glucose decomposing ability of T1DM mice, thereby lowering blood glucose.

The results show that the blood glucose level of the mice in the control group administered with vehicle PBS is remarkably higher than that of the mice in the group administered with plasminogen, and the statistical difference is significant (P=0.04) (FIG. 14). This indicates that plasminogen can enhance the glucose decomposing ability of T1DM mice, thereby lowering blood glucose.

Example 15. Plasminogen Promotes Insulin Secretion of Diabetic Mice

Nine 27-week-old male db/db mice were weighed and randomly divided into two groups based on the body weight, a group of 4 mice administered with plasminogen and a control group of 5 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 35, the mice were fasted for 16 hours, and on day 36, the blood was taken from removed eyeballs, the blood was centrifuged to obtain a supernatant, and the serum insulin level was detected using an insulin detection kit (Mercodia AB) according to operating instructions.

Figure 15:
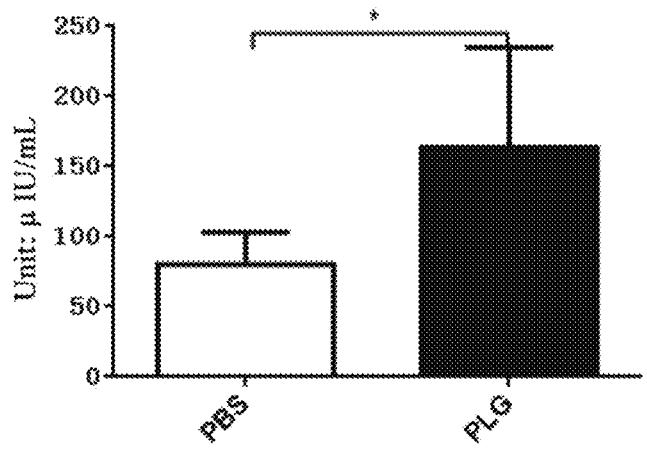
FIG. 15 shows detection results of serum insulin after administration of plasminogen to 27-week-old diabetic mice for 35 days. The results show that the serum insulin level in the group administered with plasminogen is remarkably higher than that in the control group administered with vehicle PBS, and the statistical difference is significant (* indicates P<0.05). This indicates that plasminogen can effectively promote secretion of insulin.

The detection results show that the serum insulin level in the group administered with plasminogen is remarkably higher than that in the control group administered with vehicle PBS, and the statistical difference is significant (* indicates P<0.05) (FIG. 15). This indicates that plasminogen can significantly promote secretion of insulin in diabetic mice.

Example 16. Protective Effect of Plasminogen on Pancreas of Diabetic Mice

Seven 24- to 25-week-old male db/db mice were randomly divided into two groups based on the body weight, a group of 10 mice administered with plasminogen, and a control group of 6 mice administered with vehicle PBS. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The tissue sections were 3 μm thick. The sections were dewaxed and rehydrated, stained with hematoxylin and eosin (H&E staining), differentiated with 1% hydrochloric acid in alcohol, and returned to blue with ammonia water. The sections were sealed after dehydration with alcohol gradient, and observed under an optical microscope at 200× and 400×.

Figure 16:
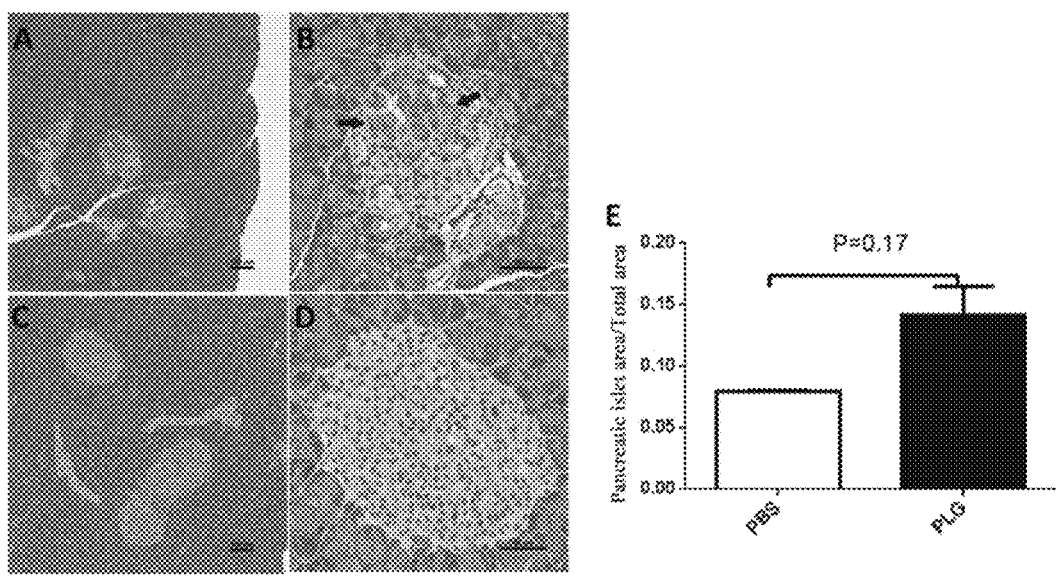
FIGS. 16A-E show the HE-stained images of the pancreas and the statistical analysis result of pancreatic islet area ratios after administration of plasminogen to 24- to 25-week-old diabetic mice for 31 days. A and B represent a control group administered with vehicle PBS, C and D represent a group administered with plasminogen, and E represents the quantitative analysis result of pancreatic islet area. The results show that most of the pancreatic islets in the control group administered with vehicle PBS are atrophied, the atrophied pancreatic islet cells are replaced by acini (indicated by arrows), and there is acinar hyperplasia at the edge of the pancreatic islets, causing the boundary between pancreatic islet and acini to be unclear; in the group administered with plasminogen, most of the pancreatic islets are larger than those in the control group, there is no acinar hyperplasia in the pancreatic islets, only a small number of acini remain in a few pancreatic islets, and the boundary between pancreatic islet and acini is clear. Comparing the group administered with plasminogen with the control group in terms of the area ratio of pancreatic islet to pancreas, it is found that the area ratio in the administration group are almost twice as large as that in the control group. This indicates that plasminogen can promote repair of impaired pancreatic islets in 24- to 25-week-old diabetic mice, by which diabetes mellitus is treated by repairing impaired pancreatic islets.

The results show that most of the pancreatic islets in the control group administered with vehicle PBS (FIGS. 16A and 16B) are atrophied, the atrophied pancreatic islet cells are replaced by acini (indicated by arrows), and there is acinar hyperplasia at the edge of the pancreatic islets, causing the boundary between pancreatic islet and acini to be unclear; in the group administered with plasminogen (FIGS. 16C and 16D), most of the pancreatic islets are larger than those in the control group, there is no acinar hyperplasia in the pancreatic islets, only a small number of acini remain in a few pancreatic islets, and the boundary between pancreatic islet and acini is clear. Comparing the administration group with the control group in terms of the area ratio of pancreatic islet to pancreas, it is found that the area ratio in the group administered with plasminogen are almost twice as large as that in the control group (FIG. 16E). It indicates that plasminogen can promote the repair of impaired pancreatic islets in diabetic mice.

Example 17. Plasminogen Reduces Collagen Deposition in Pancreatic Islet of Diabetic Mice Sixteen 24- to 25-week-old male db/db mice were randomly divided into two groups based on the body weight, 10 mice in the group administered with plasminogen, and 6 mice in the control group administered with vehicle PBS. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The tissue sections were 3 μm thick. The sections were dewaxed and rehydrated and washed with water once. After stained with 0.1% Sirius red for 60 min, the sections were flushed with running water. After stained with hematoxylin for 1 min, the sections were flushed with running water, differentiated with 1% hydrochloric acid in alcohol and returned to blue with ammonia water, flushed with running water, dried and sealed. The sections were observed under an optical microscope at 200×.

Sirius red staining allows for long-lasting staining of collagen. As a special staining method for pathological sections, Sirius red staining can show the collagen tissue specifically.

Figure 17:
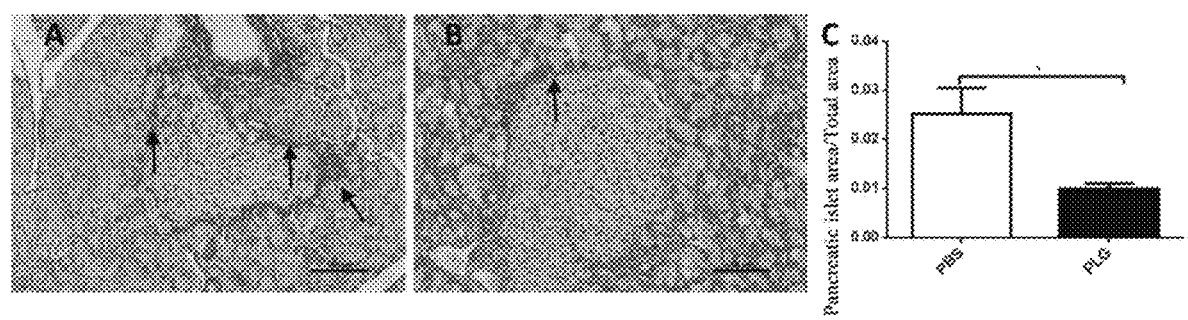
FIGS. 17A-C show the observed results of Sirius red-staining for pancreatic islets after administration of plasminogen to 24- to 25-week-old diabetic mice for 31 days. A represents the control group administered with vehicle PBS, B represents the group administered with plasminogen, and C represents the quantitative analysis results. The results show that the collagen deposition (indicated by an arrow) in the pancreatic islet of mice in the group administered with plasminogen is remarkably less than that in the control group administered with vehicle PBS, and the statistical difference is significant (* indicates P<0.05). This indicates that plasminogen can ameliorate pancreatic islet fibrosis in diabetic animals.

The staining results show that the collagen deposition (indicated by an arrow) in the pancreatic islet of the mice in the group administered with plasminogen (FIG. 17B) is remarkably lower than that in the control group administered with vehicle PBS (FIG. 17A), and the statistical difference is significant (* indicates P<0.05) (FIG. 17C). This indicates that plasminogen can reduce pancreatic islet fibrosis in diabetic animals.

Example 18. Plasminogen Reduces Pancreatic Islet Cell Apoptosis in Diabetic Mice Six 24- to 25-week-old male db/db mice were randomly divided into two groups based on the body weight, a group of 4 mice administered with plasminogen, and a control group of 2 mice administered with vehicle PBS. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum solution (Vector laboratories, Inc., USA) for 1 hour, and thereafter, the goat serum solution was discarded, and the tissues were circled with a PAP pen. The sections were incubated with rabbit anti-mouse Caspase-3 antibody (Wuhan Boster Biological Technology, BA2142) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with a gradient, permeabilization and sealing, the sections were observed under an optical microscope at 400×.

Caspase-3 is the most important terminal cleaving enzyme in the process of apoptosis, and the more it is expressed, the more cells are in the state of apoptosis[20].

Figure 18:
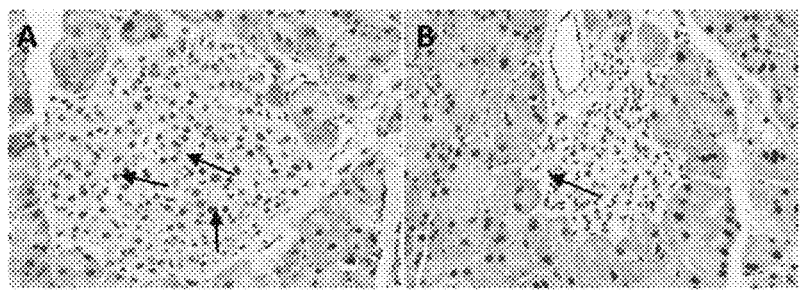
FIGS. 18A-B show the observed results of immunohistochemical staining for Caspase-3 of the pancreatic islets after administration of plasminogen to 24-to 25-week-old diabetic mice for 31 days. A represents the control group administered with vehicle PBS, and B represents the group administered with plasminogen. The results show that the expression of Caspase-3 (indicated by an arrow) in the group administered with plasminogen is remarkably lower than that in the control group administered with vehicle PBS. This indicates that plasminogen can reduce the apoptosis of pancreatic islet cells and protect the pancreatic tissue of diabetic mice.

The experimental results of the present invention show that the expression of Caspase-3 (indicated by an arrow) in the group administered with plasminogen (FIG. 18B) is remarkably lower than that in the control group administered with vehicle PBS (FIG. 18A). This indicates that plasminogen can reduce the apoptosis of pancreatic islet cells.

Example 19. Plasminogen Promotes Expression and Secretion of Insulin in 17- to 18-Week-Old Diabetic Mice Eight 17- to 18-week-old male db/db mice were randomly divided into two groups based on the body weight, a group administered with plasminogen and a control group administered with vehicle PBS, with 4 mice in each group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 µm. The sections were dewaxed and rehydrated and washed with water once. The sections were incubated with 3% hydrogen peroxide for 15 minutes and washed with water twice for 5 minutes each time. The sections were blocked with 5% normal goat serum solution (Vector laboratories, Inc., USA) for 1 hour, and thereafter, the goat serum solution was discarded, and the tissues were circled with a PAP pen. The sections were incubated with rabbit anti-mouse insulin antibody (Abcam, ab63820) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with a gradient, permeabilization and sealing, the sections were observed under an optical microscope at 200×.

Figure 19:
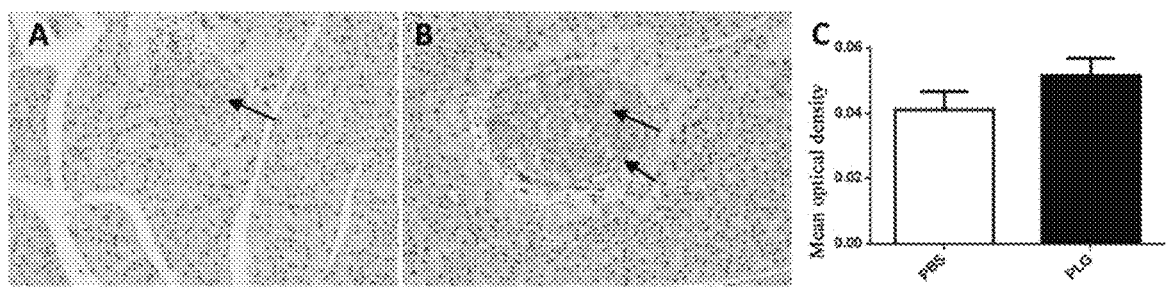
FIGS. 19A-C show the results of immunohistochemical staining for insulin of the pancreatic islets after administration of plasminogen to 17- to 18-week-old diabetic mice for 35 days. A represents the control group administered with vehicle PBS, B represents the group administered with plasminogen, and C represents the quantitative analysis results. The results show that the expression of insulin (indicated by arrows) in the group administered with plasminogen is remarkably higher than that in the control group administered with vehicle PBS, and the statistical difference is nearly significant (P=0.15). This indicates that plasminogen can promote repair of pancreatic islet function and promote production and secretion of insulin.

The results show that the expression of insulin (indicated by arrows) in the group administered with plasminogen (FIG. 19B) is remarkably higher than that in the control group administered with vehicle PBS (FIG. 19A), and the statistical difference is nearly significant (P=0.15) (FIG. 19C). This indicates that plasminogen can promote repair of pancreatic islet function and promote expression and secretion of insulin.

Example 20. Plasminogen Promotes Expression and Secretion of Insulin in 24- to 25-Week-Old Diabetic Mice Eight 24- to 25-week-old male db/db mice were randomly divided into two groups based on the body weight, a group of 5 mice administered with plasminogen, and a control group of 3 mice administered with vehicle PBS. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 µm. The sections were dewaxed and rehydrated and washed with water once. The sections were incubated with 3% hydrogen peroxide for 15 minutes and washed with water twice for 5 minutes each time. The sections were blocked with 5% normal goat serum solution (Vector laboratories, Inc., USA) for 1 hour, and thereafter, the goat serum solution was discarded, and the tissues were circled with a PAP pen. The sections were incubated with rabbit anti-mouse insulin antibody (Abcam, ab63820) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with a gradient, permeabilization and sealing, the sections were observed under an optical microscope at 200×.

Figure 20:
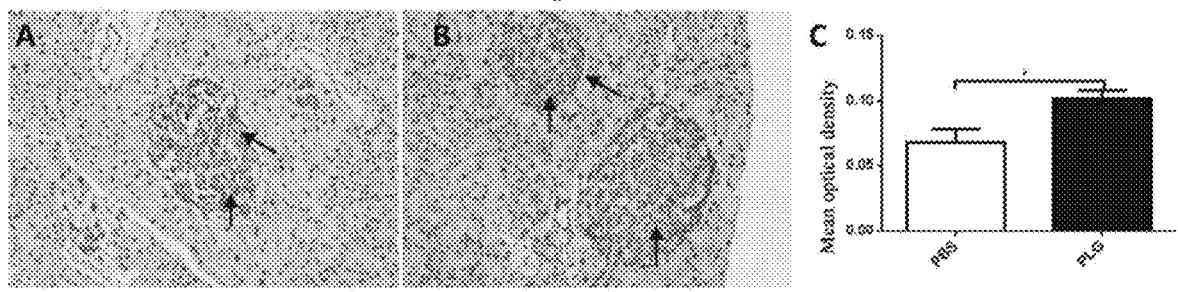
FIGS. 20A-C show the observed results of immunohistochemical staining for insulin of the pancreatic islets after administration of plasminogen to 24- to 25-week-old diabetic mice for 31 days. A represents the control group administered with vehicle PBS, B represents the group administered with plasminogen, and C represents the quantitative analysis results. The results show that the expression of insulin (indicated by arrows) in the group administered with plasminogen is remarkably higher than that in the control group administered with vehicle PBS, and the statistical difference is significant (* indicates P<0.05). This indicates that plasminogen can promote repair of pancreatic islet function and promote production and secretion of insulin.

The results show that the expression of insulin (indicated by arrows) in the group administered with plasminogen (FIG. 20B) is remarkably higher than that in the control group administered with vehicle PBS (FIG. 20A), and the statistical difference is significant (P=0.02) (FIG. 20C). This indicates that plasminogen can effectively repair the pancreatic islet function and promote expression and secretion of insulin.

Example 21. Plasminogen Promotes Repair of Insulin Synthesis and Secretion Function of Diabetic Mice Nine 27-week-old male db/db mice were randomly divided into two groups based on the body weight, a group of 4 mice administered with plasminogen, and a control group of 5 mice administered with vehicle PBS. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 35, the mice were fasted for 16 hours; and on day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 µm. The sections were dewaxed and rehydrated and washed with water once. The sections were incubated with 3% hydrogen peroxide for 15 minutes and washed with water twice for 5 minutes each time. The sections were blocked with 5% normal goat serum solution (Vector laboratories, Inc., USA) for 1 hour, and thereafter, the goat serum solution was discarded, and the tissues were circled with a PAP pen. The sections were incubated with rabbit anti-mouse insulin antibody (Abcam, ab63820) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with a gradient, permeabilization and sealing, the sections were observed under an optical microscope at 200×.

Figure 21:
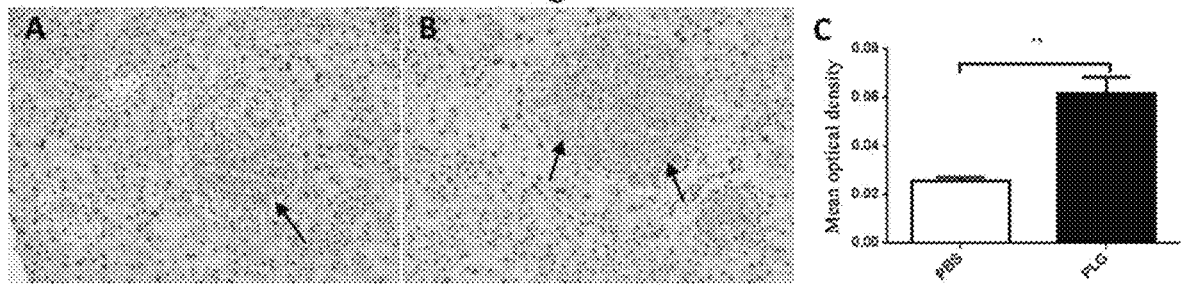
FIGS. 21A-C show the results of immunohistochemical staining for insulin of the pancreatic islets after administration of plasminogen to 27-week-old diabetic mice for 35 days. A represents the control group administered with vehicle PBS, B represents the group administered with plasminogen, and C represents the quantitative analysis results. The results show that the expression of insulin (indicated by arrows) in the group administered with plasminogen is remarkably higher than that in the control group administered with vehicle PBS, and the statistical difference is extremely significant (** indicates P<0.01). This indicates that plasminogen can effectively promote repair of pancreatic islet function and promote production and secretion of insulin.

The results show that the expression of insulin (indicated by arrows) in the group administered with plasminogen (FIG. 21B) is remarkably higher than that in the control group administered with vehicle PBS (FIG. 21A), and the statistical difference is extremely significant (P=0.005) (FIG. 21C). This indicates that plasminogen can effectively repair the pancreatic islet function of diabetic mice and improve expression and secretion of insulin.

Example 22. Plasminogen Promotes Expression of Multi-Directional Nuclear Transcription Factor NF-κB in Pancreatic Islet of 24- to 25-Week-Old Diabetic Mice Ten 24- to 25-week-old male db/db mice were randomly divided into two groups based on the body weight, a group of 4 mice administered with plasminogen and a control group of 6 mice administered with vehicle PBS; in addition, four additional db/m mice were used as a normal control group and this normal control group was not treated. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum solution (Vector laboratories, Inc., USA) for 1 hour, and thereafter, the goat serum solution was discarded, and the tissues were circled with a PAP pen. The sections were incubated with rabbit anti-mouse NF-κB (Cell Signaling, 8242) at 4° C. overnight and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with a gradient, permeabilization and sealing, the sections were observed under an optical microscope at 200×.

NF-κB is a member of the transcription factor protein family and plays an important role in repair of an inflammation[21].

Figure 22:
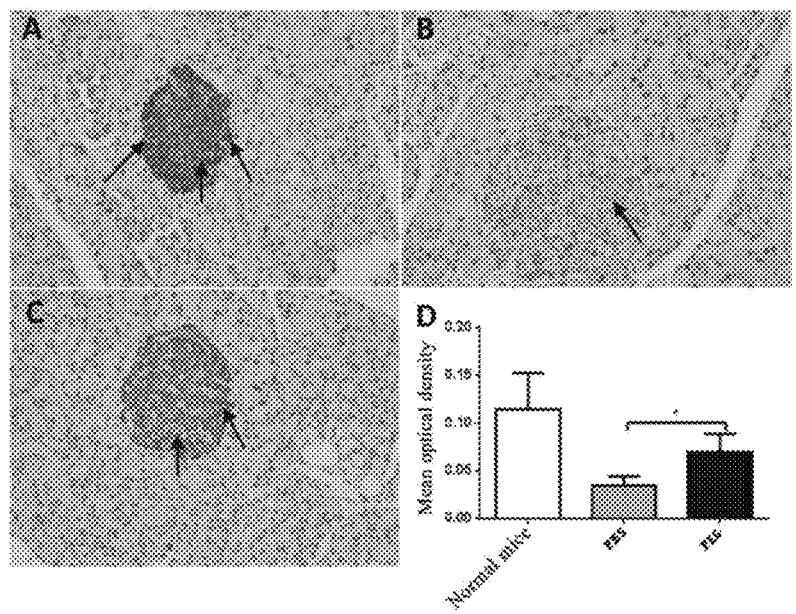

The experimental results of the present invention show that the expression of NF-κB (indicated by arrows) in the group administered with plasminogen (FIG. 22C) is similar to that in normal control mice (FIG. 22A), and is remarkably higher than that in the control group administered with vehicle PBS (FIG. 22B), and the statistical difference is significant (* indicates P<0.05) (FIG. 22D). This indicates that plasminogen can promote expression of multi-directional nuclear transcription factor NF-κB, thereby promoting repair of an inflammation in the pancreatic islet of 24- to 25-week-old diabetic mice.

Example 23. Plasminogen Reduces Proliferation of Pancreatic Islet α Cells, Restores Normal Distribution of Pancreatic Islet α Cells, and Lowers Secretion of Glucagon in 17- to 18-Week-Old Diabetic Mice Eight 17- to 18-week-old male db/db mice and three male db/m mice were taken. The db/db mice were randomly divided into two groups based on the body weight, a group administered with plasminogen and a control group administered with vehicle PBS, with 4 mice in each group, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days; and the normal control mice were not administered. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum solution was discarded. Rabbit anti-mouse glucagon antibody (Abcam, ab92517) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Pancreatic islet α cells synthesize and secrete glucagon, and are mainly distributed in the peripheral region of the pancreatic islet.

Figure 23:
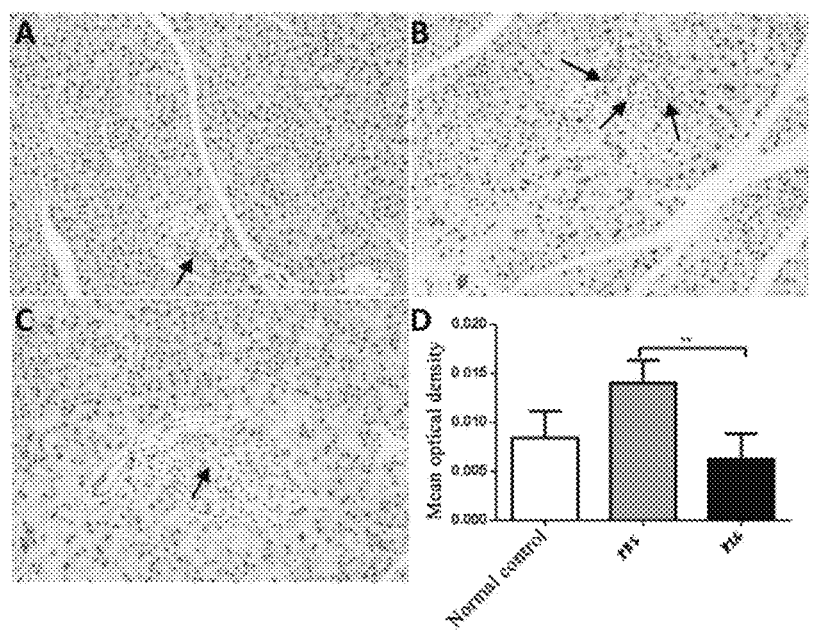

The results show that compared with the group administered with plasminogen (FIG. 23C), glucagon-positive cells (indicated by arrows) in the control group administered with vehicle PBS (FIG. 23B) are remarkably increased, the positive cells infiltrate into the central region of the pancreatic islet, and the mean optical density quantitative analysis results show a statistical difference (** indicates P<0.01) (FIG. 23D); and glucagon-positive cells in the group administered with plasminogen are dispersed at the periphery of the pancreatic islet, and compared with the group administered with vehicle PBS, the morphology of the pancreatic islet in the group administered with plasminogen is closer to that in the normal control group (FIG. 23A). This indicates that plasminogen can significantly inhibit proliferation of pancreatic islet α cells and secretion of glucagon, and correct the disordered distribution of pancreatic islet α cells in 17- to 18-week-old diabetic mice, suggesting that plasminogen promotes repair of impaired pancreatic islets.

Example 24. Plasminogen Promotes Expression of Insulin Receptor Substrate-2 (IRS-2) in the Pancreatic Islets of 17- to 18-Week-Old Diabetic Mice Seven male db/db mice and three male db/m mice, 17-18 weeks old, were included, wherein the db/db mice were randomly divided into two groups based on the body weight, a group of 3 mice administered with plasminogen and a control group of 4 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days; and the normal control mice were not administered. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse IRS-2 antibody (Abcam, ab134101) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Figure 24:
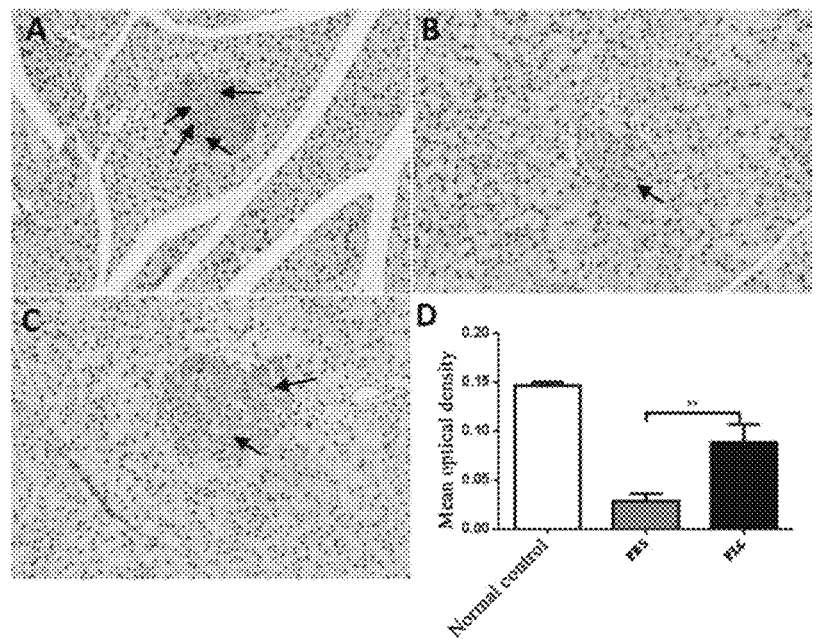

Insulin receptor substrate-2 (IRS-2) is a substrate that can be phosphorylated by an activated insulin receptor tyrosine kinase, is an important molecule in an insulin signaling pathway and is very important for the survival of pancreatic islet 13 cells. Increased expression of IRS-2 has a protective effect on pancreatic islet β cells, and is crucial for the maintenance of functional pancreatic islet 13 cells[22-23]. The immunohistochemical results of IRS-2 show that the positive expression of IRS-2 (indicated by an arrow) in the pancreatic islets of mice in the control group administered with vehicle PBS (FIG. 24B) is remarkably lower than that in the group administered with plasminogen (FIG. 24C), and the statistical difference is extremely significant (** indicates P<0.01) (FIG. 24D); in addition, compared with the group administered with vehicle PBS, the result of the group administered with plasminogen is closer to that of the blank control group (FIG. 24A). This indicates that plasminogen can effectively increase expression of IRS-2 in pancreatic islet cells in 17- to 18-week-old diabetic mice.

Example 25. Plasminogen Promotes Expression of IRS-2 in Pancreatic Islet of 24- to 25-Week-Old Diabetic Mice Eleven male db/db mice and five male db/m mice, 24-25 weeks old, were included, wherein the db/db mice were randomly divided into two groups based on the body weight, a group of 5 mice administered with plasminogen and a control group of 6 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 31 consecutive days; and the normal control mice were not administered. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse IRS-2 antibody (Abcam, ab134101) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Figure 25:
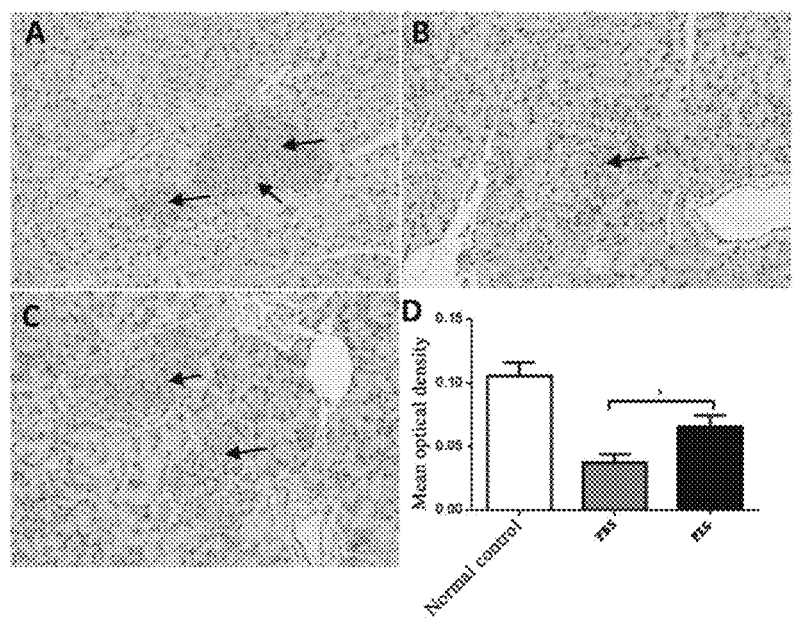

The immunohistochemical results of IRS-2 show that the positive expression of IRS-2 (indicated by an arrow) in the pancreatic islets of mice in the control group administered with vehicle PBS (FIG. 25B) is remarkably lower than that in the group administered with plasminogen (FIG. 25C), and the statistical difference is significant (* indicates P<0.05) (FIG. 25D); in addition, compared with the group administered with vehicle PBS, the result of the group administered with plasminogen is closer to that of the normal control group (FIG. 25A). This indicates that plasminogen can effectively increase expression of IRS-2 in pancreatic islet cells in 24- to 25-week-old diabetic mice.

Example 26. Plasminogen Promotes Expression of IRS-2 in Pancreatic Islet of 27-Week-Old Diabetic Mice Nine male db/db mice and three male db/m mice, 27 weeks old, were included, wherein the db/db mice randomly divided into two groups based on the body weight, a group of 4 mice administered with plasminogen and a control group of 5 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days; and the normal control mice were not administered. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse IRS-2 antibody (Abcam, ab134101) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The immunohistochemical results of IRS-2 show that the positive expression of IRS-2 (indicated by an arrow) in the pancreatic islets of mice in the control group administered with vehicle PBS (FIG. 26B) is remarkably lower than that in the group administered with plasminogen (FIG. 26C); and the expression level of IRS-2 in the group administered with plasminogen is closer to that of the mice in the normal control group (FIG. 26A). This indicates that plasminogen can effectively increase expression of IRS-2 in pancreatic islet cells in 27-week-old diabetic mice.

Example 27. Plasminogen Promotes Expression of IRS-2 in the Pancreatic Islets of PLG$^{+/+}$ T1DM Mice Fifteen 9- to 10-week-old male PLG$^{+/+}$ mice were randomly divided into two groups based on the body weight, a blank control group (5 mice) and a model group (10 mice). The mice in the model group were fasted for 4 hours and intraperitoneally injected with 200 mg/kg STZ (sigma S0130), in a single dose, to induce type I diabetes mellitus [19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS and a group administered with plasminogen, with 5 mice in each group. After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse IRS-2 antibody (Abcam, ab134101) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The immunohistochemical results of IRS-2 show that the positive expression of IRS-2 (indicated by an arrow) in the pancreatic islets of mice in the control group administered with vehicle PBS (FIG. 27B) is remarkably lower than that in the group administered with plasminogen (FIG. 27C), and compared with the group administered with vehicle PBS, the result of the group administered with plasminogen is closer to that of the blank control group (FIG. 27A). This indicates that plasminogen can effectively increase expression of IRS-2 in pancreatic islet cells, improve insulin signal transduction, and reduce the pancreatic islet 13 cell injury in PLG$^{+/+}$ T1DM mice.

Example 28. Plasminogen Reduces Infiltration of Neutrophils in the Pancreatic Islets of 24- to 26-Week-Old Diabetic Mice Nine male db/db mice and three male db/m mice, 24-26 weeks old, were included, wherein the db/db mice were randomly divided into two groups, a group of 4 mice administered with plasminogen and a control group of 5 mice administered with vehicle PBS, and the db/m mice were used as a normal control group. The day when the experiment began was recorded on Day 0, and the mice were weighed and grouped. From the second day of the experiment, plasminogen or PBS was administered to the mice, and the day was recorded as Day 1. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were repaired with EDTA for 30 minutes, and gently rinsed with water after cooling at room temperature for 10 minutes. The tissues were incubated with 3% hydrogen peroxide for 15 minutes. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rat anti-mouse neutrophil antibody (cedarlane, CL8993AP) was added to the sections dropwise, incubated at 4° C. overnight, and washed with 0.01 M PBS twice for 5 minutes each time. The sections were incubated with a secondary antibody, goat anti-rat IgG (HRP) antibody (Abcam, ab97057), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 400×.

Neutrophils are important members of the nonspecific cellular immune system, and are attracted to an inflammatory site by chemotactic substances when inflammation occurs.

The immunohistochemical results of neutrophils show that the cells having positive expression in the group administered with plasminogen (FIG. 28C) are less than those in the control group administered with vehicle PBS (FIG. 28B), and compared with the group administered with vehicle PBS, the result of the group administered with plasminogen is closer to that of the normal control group (FIG. 28A). This indicates that plasminogen can reduce infiltration of neutrophils in the pancreatic islets of diabetic mice.

Example 29. Plasminogen Reduces Infiltration of Neutrophils in the Pancreatic Islets of PLG$^{-/-}$ Mice in a T1DM Model Ten 9- to 10-week-old male PLG$^{-/-}$ mice were randomly divided into two groups based on the body weight, a blank control group (3 mice) and a model group (7 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS (3 mice) and a group administered with plasminogen (4 mice). After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were repaired with EDTA for 30 minutes, and gently rinsed with water after cooling at room temperature for 10 minutes. The tissues were incubated with 3% hydrogen peroxide for 15 minutes. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rat anti-mouse neutrophil antibody (cedarlane, CL8993AP) was added to the sections dropwise, incubated at 4° C. overnight, and washed with 0.01 M PBS twice for 5 minutes each time. The sections were incubated with a secondary antibody, goat anti-rat IgG (HRP) antibody (Abcam, ab97057), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 400×.

The immunohistochemical results of neutrophils show that the cells having positive expression (indicated by an arrow) in the group administered with plasminogen (FIG. 29C) are less than those in the control group administered with vehicle PBS (FIG. 29B), and compared with the group administered with vehicle PBS, the result of the group administered with plasminogen is closer to that of the blank control group (FIG. 29A). This indicates that plasminogen can reduce infiltration of neutrophils in the pancreatic islets of PLO' mice in a T1DM model.

Example 30. Plasminogen Reduces Infiltration of Neutrophils in the Pancreatic Islets of PLG$^{+/+}$ Mice in a T1DM Model Fifteen 9- to 10-week-old male PLG$^{+/+}$ mice were randomly divided into two groups based on the body weight, a blank control group (5 mice) and a model group (10 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS and a group administered with plasminogen, with 5 mice in each group.

After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The sections were repaired with EDTA for 30 minutes, and gently rinsed with water after cooling at room temperature for 10 minutes. The tissues were incubated with 3% hydrogen peroxide for 15 minutes. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rat anti-mouse neutrophil antibody (cedarlane, CL8993AP) was added to the sections dropwise, incubated at 4° C. overnight, and washed with 0.01 M PBS twice for 5 minutes each time. The sections were incubated with a secondary antibody, goat anti-rat IgG (HRP) antibody (Abcam, ab97057), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 400×.

The immunohistochemical results of neutrophils show that the cells having positive expression (indicated by an arrow) in the group administered with plasminogen (FIG. 30C) are less than those in the control group administered with vehicle PBS (FIG. 30B), and compared with the group administered with vehicle PBS, the result of the group administered with plasminogen is closer to that of the blank control group (FIG. 30A). This indicates that plasminogen can reduce infiltration of neutrophils in the pancreatic islets of PLG$^{+/+}$ mice in a T1DM model.

Example 31. Plasminogen Promotes Synthesis and Secretion of Insulin in PLG$^{+/+}$ Mice in a T1DM Model Ten 9- to 10-week-old male PLG$^{-/-}$ mice were randomly divided into two groups based on the body weight, a blank control group (3 mice) and a model group (7 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS (3 mice) and a group administered with plasminogen (4 mice). After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse insulin antibody (Abcam, ab63820) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The immunohistochemical results show that the positive expression of insulin (indicated by arrows) in the group administered with plasminogen (FIG. 31C) is remarkably higher than that in the control group administered with vehicle PBS (FIG. 31B), and compared with the group administered with vehicle PBS, the result of the group administered with plasminogen is closer to that of the blank control group (FIG. 31A). This indicates that plasminogen can promote synthesis and secretion of insulin in PLO' mice in a T1DM model.

Example 32. Plasminogen Promotes Synthesis and Expression of Insulin in PLG$^{+/+}$ Mice in a T1DM Model Fifteen 9- to 10-week-old male PLG$^{+/+}$ mice were randomly divided into two groups based on the body weight, a blank control group (5 mice) and a model group (10 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS and a group administered with plasminogen, with 5 mice in each group.

After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse insulin antibody (Abcam, ab63820) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA).

After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×. The immunohistochemical results show that the positive expression of insulin (indicated by arrows) in the group administered with plasminogen (FIG. 32C) is remarkably higher than that in the control group administered with vehicle PBS (FIG. 32B), and compared with the group administered with vehicle PBS, the result of the group administered with plasminogen is closer to that of the blank control group (FIG. 32A). This indicates that plasminogen can promote synthesis and expression of insulin in PLG$^{+/+}$ mice in a T1DM model.

Example 33. Plasminogen Promotes Expression of Multi-Directional Nuclear Transcription Factor NF-κB in the Pancreatic Islets of PLG$^{+/+}$ Mice in a T1DM Model Ten 9- to 10-week-old male PLG$^{-/-}$ mice were randomly divided into two groups based on the body weight, a blank control group (3 mice) and a model group (7 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS (3 mice) and a group administered with plasminogen (4 mice). After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse NF-κB antibody (Cell Signaling, 8242) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The experimental results show that the expression of NF-κB (indicated by arrows) in the group administered with plasminogen (FIG. 33C) is remarkably higher than that in the control group administered with vehicle PBS (FIG. 33B). This indicates that plasminogen can promote expression of multi-directional nuclear transcription factor NF-κB, thereby promoting repair of an inflammation in the pancreatic islet.

Example 34. Plasminogen Promotes Expression of Multi-Directional Nuclear Transcription Factor NF-κBin Pancreatic Islet of 17- to 18-Week-Old Diabetic Mice Seven 17- to 18-week-old male db/db mice were randomly divided into two groups based on the body weight, a group of 3 mice administered with plasminogen, and a control group of 4 mice administered with vehicle PBS. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse NF-κB antibody (Cell Signaling, 8242) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The experimental results of the present invention show that the expression of NF-κB (indicated by arrows) in the group administered with plasminogen (FIG. 34B) is remarkably higher than that in the control group administered with vehicle PBS (FIG. 34A). This indicates that plasminogen can promote expression of multi-directional nuclear transcription factor NF-κB, thereby promoting repair of an inflammation in the pancreatic islet of relatively young (17- to 18-week-old) diabetic mice.

Example 35. Plasminogen Promotes Expression of Multi-Directional Nuclear Transcription Factor NF-κBin 27-Week-Old Diabetic Mice Nine male db/db mice and three male db/m mice, 27 weeks old, were included, wherein the db/db mice randomly divided into two groups based on the body weight, a group of 4 mice administered with plasminogen and a control group of 5 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days; and the normal control mice were not administered. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse NF-κB antibody (Cell Signaling, 8242) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The experimental results show that the expression of NF-κB (indicated by arrows) in the group administered with plasminogen (FIG. 35C) is remarkably higher than that in the control group administered with vehicle PBS (FIG. 35B), and compared with the group administered with vehicle PBS, the result of the group administered with plasminogen is closer to that of the normal control group (FIG. 35A). This indicates that plasminogen can promote expression of multi-directional nuclear transcription factor NF-κB in relatively old (27-week-old) diabetic mice, thereby promoting repair of an inflammation in the pancreatic islet.

Example 36. Plasminogen Promotes Expression of TNF-α in Pancreatic Islet of 24- to 25-Week-Old Diabetic Mice Eleven male db/db mice and five male db/m mice, 24-25 weeks old, were included, wherein the db/db mice were randomly divided into two groups based on the body weight, a group of 5 mice administered with plasminogen and a control group of 6 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein or without any liquid, both lasting for 31 consecutive days; and the normal control mice were not administered. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse TNF-α antibody (Abcam, ab34674) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Tumor necrosis factor-α (TNF-α) is mainly produced by activated monocytes/macrophages and is an important pro-inflammatory factor[24].

The research results of this experiment show that the positive expression of TNF-α in the group administered with plasminogen (FIG. 36C) are remarkably higher than that in the control group administered with vehicle PBS (FIG. 36B), and compared with the group administered with vehicle PBS, the result of the group administered with plasminogen is closer to that of the normal control group (FIG. 36A). This indicates that plasminogen can promote expression of TNF-α in 24- to 25-week-old diabetic mice, and promote repair of impaired pancreatic islets.

Example 37. Plasminogen Promotes Expression of TNF-α in Pancreatic Islet of 27-Week-Old Diabetic Mice Nine male db/db mice and three male db/m mice, 27 weeks old, were included, wherein the db/db mice randomly divided into two groups based on the body weight, a group of 4 mice administered with plasminogen and a control group of 5 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 35 consecutive days; and the normal control mice were not administered. On day 36, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse TNF-α antibody (Abcam, ab34674) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The research results show that the positive expression of TNF-α in the group administered with plasminogen (FIG. 37C) are remarkably higher than that in the control group administered with vehicle PBS (FIG. 37B), and compared with the group administered with vehicle PBS, the result of the group administered with plasminogen is closer to that of the normal control group (FIG. 37A). This indicates that plasminogen can promote expression of TNF-α in 27-week-old diabetic mice, and promote repair of impaired pancreatic islets.

Example 38. Plasminogen Promotes Expression of TNF-α in the Pancreatic Islets of PLG$^{+/+}$ Mice in a T1DM Model Ten 9- to 10-week-old male PLO' mice were randomly divided into two groups based on the body weight, a blank control group (3 mice) and a model group (7 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group administered with vehicle PBS (3 mice) and a group administered with plasminogen (4 mice). After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse TNF-α antibody (Abcam, ab34674) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The research results of this experiment show that the positive expression of TNF-α in the group administered with plasminogen (FIG. 38B) is remarkably higher than that in the control group administered with vehicle PBS (FIG. 38A). This indicates that plasminogen can promote expression of TNF-α in the pancreatic islets of PLG−/− mice in a T1DM model, and promote repair of impaired pancreatic islets.

Example 39. Plasminogen Alleviates the Pancreatic Islet Injury in PLG$^{-/-}$ Mice in a T1DM Model Ten 9- to 10-week-old male PLG$^{-/-}$ mice were randomly divided into two groups based on the body weight, a blank control group (3 mice) and a model group (7 mice). The mice in the model group were fasted for 4 hours and intraperitoneally injected with 200 mg/kg STZ (sigma S0130), in a single dose, to induce type I diabetes mellitus[19]; and the blank control group was intraperitoneally injected with 0.25 ml of sodium citrate solution (pH 4.5) in a single dose. 12 days after the injection of STZ, the blood glucose was measured with a glucose meter. The mice in the model group were randomly divided into two groups based on the blood glucose, a control group of 3 mice administered with vehicle PBS and a group of 4 mice administered with plasminogen. After grouping, administration was carried out and this day was set as administration day 1. The group administered with plasminogen were injected with human plasminogen at a dose of 1 mg/0.1 mL/mouse/day via the tail vein, and the control group administered with vehicle PBS was injected with an equal volume of PBS via the tail vein, both lasting for 28 consecutive days; and the mice in the blank control group were not administered. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm.

The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Goat anti-mouse IgM (HRP) antibody (Abcam, ab97230) was added to the sections dropwise, incubated for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

IgM antibodies play an important role during the clearance of apoptotic and necrotic cells, and the local level of IgM antibodies at the injury site in tissues and organs are positively correlated with the degree of injury[25-26]. Therefore, detection of local level of IgM antibodies in tissues and organs can reflect the injury of the tissues and organs.

The research results show that the positive expression of IgM in the group administered with plasminogen (FIG. 39C) is remarkably lower than that in the control group administered with vehicle PBS (FIG. 39B), and compared with the group administered with vehicle PBS, the result of the group administered with plasminogen is closer to that of the blank control group (FIG. 39A). This indicates that plasminogen can reduce expression of IgM, suggesting that plasminogen can alleviate the pancreatic islet injury in PLO' mice in a T1DM model.

Example 40. Plasminogen Reduces Pancreatic Islet Cell Apoptosis in 24- to 25-Week-Old Diabetic Mice Eleven male db/db mice and five male db/m mice, 24-25 weeks old, were included, wherein the db/db mice were randomly divided into two groups based on the body weight, a group of 5 mice administered with plasminogen and a control group of 6 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein or without any liquid, both lasting for 31 consecutive days; and the normal control mice were not administered. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm.

The sections were dewaxed and rehydrated and washed with water once. A tissue was circled with a PAP pen, and a proteinase K solution was added dropwise to cover the tissue, incubated at room temperature for 7 min, and washed three times with 0.01 M PBS for 3 minutes each time. A mixed liquid of reagent 1 and reagent 2 (5:45) of TUNEL kit (Roche) was added to the sections dropwise, incubated at a constant temperature of 37° C. for 40 min, and washed with 0.01 M PBS three times for 3 minutes each time. A 3% hydrogen peroxide aqueous solution (hydrogen peroxide:methanol=1:9) prepared by using methanol was added to the sections dropwise, incubated at room temperature for 20 minutes in the dark, and washed with 0.01 M PBS three times for 3 minutes each time. Reagent 3 in a tunel kit was added to the sections dropwise, incubated at a constant temperature of 37° C. for 30 min, and washed with 0.01 M PBS three times. A DAB kit (Vector laboratories, Inc., USA) was applied for development. After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 400×.

TUNEL staining can be used to detect the breakage of nuclear DNAs in tissue cells during late apoptosis.

The results of this experiment show that positive TUNEL staining is extremely low in the normal control group (FIG. 40A). The number of positive cells (indicated by an arrow) in the group administered with plasminogen (FIG. 40C) is remarkably smaller than that in the control group administered with vehicle PBS (FIG. 40B). The apoptosis rate of the normal control group is about 8%, the apoptosis rate in the group administered with vehicle PBS is about 93%, and the apoptosis rate in the group administered with plasminogen is about 16%. This indicates that the plasminogen group can significantly reduce the apoptosis of pancreatic islet cells in diabetic mice.

Example 41. Plasminogen Improves Insulin Secretion of T1DM Model Mice

Thirteen 9- to 10-week-old male C57 mice were taken. The mice were fasted for 4 hours and then intraperitoneally injected with streptozotocin (STZ) (sigma, S0130) at 200 mg/kg body weight, in a single dose, to induce T1DM[19]. 12 days after the injection of STZ, the blood glucose was measured. The mice were randomly divided into two groups based on the blood glucose, a control group administered with vehicle PBS (6 mice) and a group administered with plasminogen (7 mice). After grouping, administration was carried out and this day was set as administration day 1. The group administered with plasminogen was injected with human plasminogen at a dose of 1 mg/0.1 mL/mouse/day via the tail vein, and the control group administered with vehicle PBS was injected with an equal volume of PBS via the tail vein. Administration was carried out for 20 consecutive days. On day 21, the mice were fasted for 6 hours, and then, blood was taken from venous plexus in the eyeballs, the blood was centrifuged to obtain a supernatant, and the concentration of serum insulin was detected using an insulin detection kit (Mercodia AB) according to operating instructions.

The results show that the concentration of insulin in the mice in the control group administered with vehicle PBS is remarkably lower than that of the mice in the group administered with plasminogen, and the statistical difference is nearly significant (P=0.08) (FIG. 41). This indicates that plasminogen can promote secretion of insulin in T1DM mice.

Example 42. Plasminogen Promotes Expression of GLP-1R in the Pancreases of 24- to 25-Week-Old Diabetic Mice Eleven male db/db mice and five male db/m mice, 24-25 weeks old, were included, wherein the db/db mice were randomly divided into two groups based on the body weight, a group of 5 mice administered with plasminogen and a control group of 6 mice administered with vehicle PBS, and the db/m mice were used as a normal control group. The first day of administration was recorded as the Day 1, and starting from this day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein or without any liquid, both lasting for 31 consecutive days; and the normal control mice were not administered. On day 32, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1R antibody (NOVUS, NBP1-97308) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The glucagon-like peptide 1 receptor (GLP-1R), a member of the glucagon receptor family, is a G-protein-coupled receptor that can regulate the blood glucose level by promoting secretion of insulin[27-28].

Figure 42:
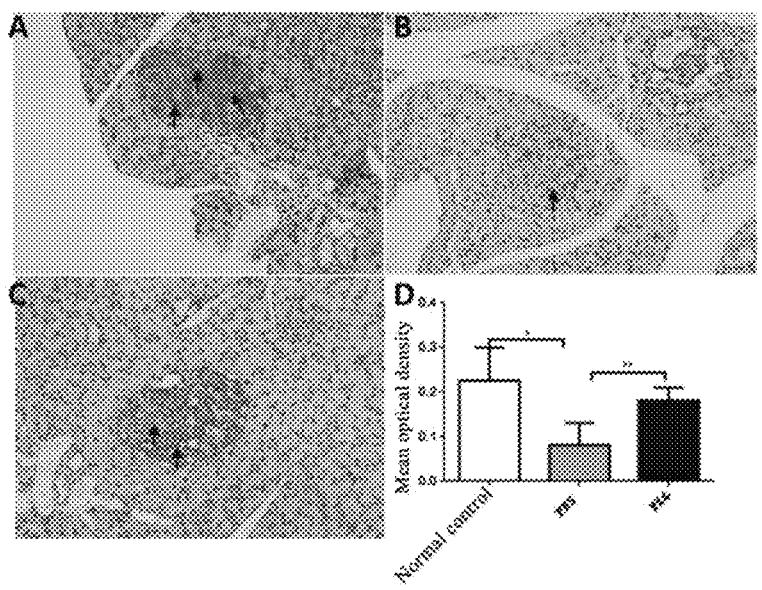

The results show that the expression of GLP-1R (indicated by an arrow) in the pancreatic islets of mice in the control group administered with vehicle PBS (FIG. 42B) is remarkably less than that in normal control mice (FIG. 42A), and although the expression of GLP-1R in the pancreatic islets of mice in the group administered with plasminogen (FIG. 42C) is also less than that in the normal control group, it is remarkably more than that in the control group administered with vehicle PBS, and the statistical difference is extremely significant (* indicates P<0.05, and ** indicates P<0.01) (FIG. 42D). The experimental results indicate that plasminogen can promote expression of GLP-1R in the pancreatic islets of diabetic mice.

Example 43. Plasminogen Promotes Expression of GLP-1R in the Pancreases of Hyperlipemia Model Mice Seventeen 9-week-old male C57 mice were fed with a 3% cholesterol high-fat diet (Nantong Trophic Animal Feed High-Tech Co., Ltd.) for 4 weeks to induce hyperlipemia[29-30]. This model was designated as the 3% cholesterol hyperlipemia model. The model mice continued to be fed with the 3% cholesterol high-fat diet. Another five male wild-type mice of the same week age were taken as the blank control group, and were fed with a normal maintenance diet during the experiment. 50 µL of blood was taken from each mouse three days before administration, and the total cholesterol was detected. The mice were randomly divided into two groups based on the total cholesterol concentration and body weight, a group administered with plasminogen (9 mice) and a control group administered with vehicle PBS (8 mice). The first day of administration was recorded as day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 consecutive days; and the mice in the blank control group were not administered. The mice were sacrificed on day 31. The pancreases were fixed in 4% paraformaldehyde for 24 to 48 hours. The fixed tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1R antibody (NOVUS, NBP1-97308) was added to the sections dropwise, incubated at 4° C. overnight, and washed with 0.01 M PBS twice for 5 minutes each time.

The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Figure 43:
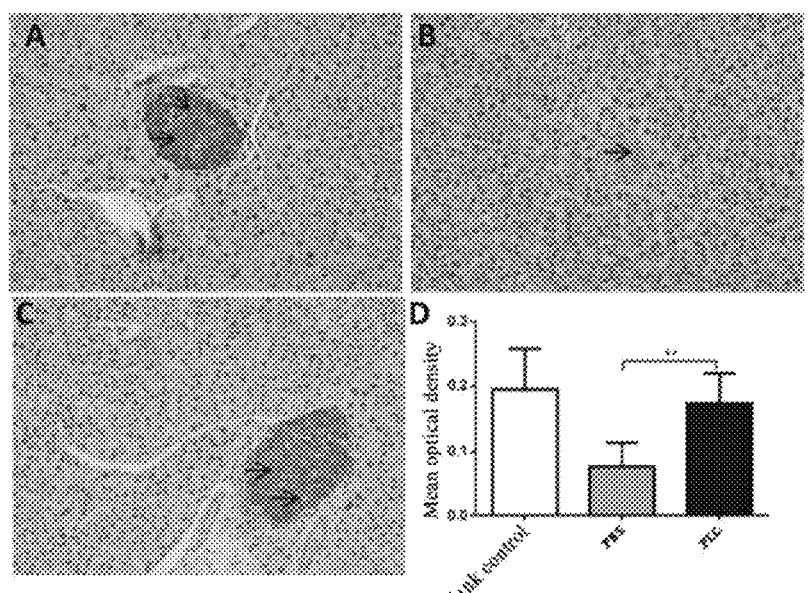

The results show that the expression of GLP-1R (indicated by an arrow) in the pancreatic islets of mice in the control group administered with vehicle PBS (FIG. 43B) is remarkably less than that in normal control mice (FIG. 43A), and although the expression of GLP-1R in the pancreatic islets of mice in the group administered with plasminogen (FIG. 43C) is also less than that in the blank control group, it is remarkably more than that in the control group administered with vehicle PBS with an extremely significant statistical difference (** indicates P<0.01) (FIG. 43D). The experimental results indicate that plasminogen can promote expression of GLP-1R in the pancreatic islets of hyperlipemia model mice.

Example 44. Plasminogen Promotes Expression of GLP-1R in the Pancreases of 14- to 15-Week-Old Diabetic Mice Twelve 14- to 15-week-old male db/db mice were weighed and randomly divided into two groups based on the body weight, a group of 6 mice administered with plasminogen and a control group of 6 mice administered with vehicle PBS, on the day the experiment started that was recorded as day 0. Starting from the 1st day, plasminogen or PBS was administered. The group administered with plasminogen was injected with human plasminogen at a dose of 2 mg/0.2 mL/mouse/day via the tail vein, and the control group administered with vehicle PBS was injected with an equal volume of PBS via the tail vein, both lasting for 28 consecutive days. On day 29, the mice were sacrificed, and the pancreas was taken and fixed in 4% paraformaldehyde. The fixed pancreas tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1R antibody (NOVUS, NBP1-97308) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×. The results show that the expression of GLP-1R in the pancreatic islets of mice in the control group administered with vehicle PBS (FIG. 44A) is remarkably less than that in the group administered with plasminogen (FIG. 44B), and the statistical difference is nearly significant (FIG. 44C) (P=0.09). The results indicate that plasminogen can promote expression of GLP-1R in the pancreatic islets of relatively young (14- to 15-week-old) diabetic mice.

Example 45. Plasminogen Promotes Expression of GLP-1R in the Livers of Atherosclerosis Model Mice Nineteen 6-week-old male APOE mice weighing 18 to 22 g were fed with a high-fat model diet (TP2031, Nantong Trophic Animal Feed High-Tech Co., Ltd.) for 16 weeks to set up an atherosclerosis model[31-32]. Three days before the administration, all mice were weighed and 50 μL of blood was collected from venous plexus in the eyeballs, for determining plasma TC and HDL for calculation of the atherosclerosis index. A mouse was randomly taken, and the remaining mice were randomly divided into two groups based on the atherosclerosis index, a group administered with plasminogen and a control group administered with vehicle PBS, with 9 mice in each group. After grouping, administration was carried out and this day was recorded as day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 consecutive days. The mice were sacrificed on Day 31. The livers were fixed in 4% paraformaldehyde for 24 to 48 hours. The fixed tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1R antibody (NOVUS, NBP1-97308) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

The results show that the expression of GLP-1R (indicated by arrows) in the livers of mice in the group administered with plasminogen (FIG. 45B) is remarkably more than that in the control group administered with vehicle PBS (FIG. 45A), and the statistical difference is extremely significant (FIG. 45C) (*** indicates P<0.001). The results show that plasminogen can promote expression of GLP-1R in the livers of atherosclerosis model mice, possibly promote the synthesis, secretion, absorption or oxidation of liver fat, reduce the level of lipids in blood, and improve hyperlipemia.

Example 46. Plasminogen Promotes Expression of GLP-1R in the Livers of Hyperlipemia Model Mice Seventeen 9-week-old male C57 mice were fed with a 3% cholesterol high-fat diet (Nantong Trophic Animal Feed High-Tech Co., Ltd.) for 4 weeks to induce hyperlipemia[29-30]. This model was designated as the 3% cholesterol hyperlipemia model. The model mice continued to be fed with the 3% cholesterol high-fat diet. 50 μL of blood was taken from each mouse three days before administration, and the total cholesterol was detected. The mice were randomly divided into two groups based on the total cholesterol concentration and body weight, a group administered with plasminogen (9 mice) and a control group administered with vehicle PBS (8 mice). After grouping, administration was carried out and this day was recorded as day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 consecutive days. The mice were sacrificed on Day 31. The livers were fixed in 4% paraformaldehyde for 24 to 48 hours. The fixed tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1R antibody (NOVUS, NBP1-97308) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×. The results show that the expression of GLP-1R (indicated by arrows) in the livers of mice in the group administered with plasminogen (FIG. 46B) is remarkably more than that in the control group administered with vehicle PBS (FIG. 46A), and the statistical difference is nearly significant (P=0.09) (FIG. 46C). The results show that plasminogen can promote expression of GLP-1R in the livers of hyperlipemia model mice, possibly promote the synthesis, secretion, absorption or oxidation of liver fat, reduce the level of lipids in blood, and improve hyperlipemia.

Example 47. Plasminogen Promotes Expression of GLP-1R in the Substantia Nigra of Parkinsonian Model Mice Twelve 9-week-old male C57 mice were taken, and weighed one day before modeling. The mice were intraperitoneally injected with 5 mg/ml MPTP solution at 30 mg/kg body weight daily for 5 consecutive days to set up a Parkinsonian model[33-34]. Formulation of the MPTP solution: 10 ml of deionized water was sucked with a syringe, and added to 100 mg of MPTP powder (sigma, M0896) to formulate a 10 mg/ml stock solution. Then, 1 ml of the stock solution was sucked into an ampoule, and 1 ml of deionized water was added to a final concentration of 5 mg/ml. After modeling, the mice were randomly divided into two groups, a control group administered with vehicle PBS and a group administered with plasminogen, with 6 mice in each group, and administration was carried out and this day was recorded as day 1. Mice in the group administered with plasminogen were administered with a plasminogen solution at a dose of 1 mg/0.1 mL/mouse/day via the tail vein, and an equal volume of PBS was administered to mice in the control group administered with vehicle PBS via the tail vein, both lasting for 14 days. The mice were sacrificed on day 15. The brains were quickly removed and fixed in 4% paraformaldehyde for 24 to 48 hours. The fixed brain tissues were paraffin-embedded after dehydration with alcohol gradient and permeabilization with xylene. The substantia nigra sections were located. The thickness of the sections was 4 µm. The sections were dewaxed and rehydrated, and washed with water once. The tissues were circled with a PAP pen, incubated with 3% hydrogen peroxide for 15 minutes, and washed with 0.01 M PBS twice for 5 minutes each time. The sections were blocked with 5% normal goat serum solution (Vector laboratories, Inc., USA) for 30 minutes, and after the time was up, the goat serum solution was discarded. Rabbit anti-mouse GLP-1R antibody (NOVUS, NBP1-97308) was added to the sections dropwise, incubated at 4° C. overnight, and washed with 0.01 M PBS twice for 5 minutes each time. The sections were incubated with a secondary antibody, goat anti-rabbit IgG (HRP) antibody (Abcam), for 1 hour at room temperature and washed with 0.01 M PBS twice for 5 minutes each time. The sections were developed with a DAB kit (Vector laboratories, Inc., USA). After washing with water three times, the sections were counterstained with hematoxylin for 30 seconds and flushed with running water for 5 minutes. After dehydration with alcohol gradient, permeabilization with xylene, and sealing with a neutral gum, the sections were observed under an optical microscope at 200×.

Parkinson's disease is characterized by a loss of dopaminergic signals in neurons in the substantia nigra striatum, which also expresses GLP-1R[35].

The results show that the expression of GLP-1R (indicated by arrows) in the substantia nigra of mice in the group administered with plasminogen (FIG. 47B) is remarkably more than that in the control group administered with vehicle PBS (FIG. 47A), and the statistical difference is significant (FIG. 47C) (* indicates P<0.05). The results indicate that plasminogen can promote expression of GLP-1R in the substantia nigra of Parkinsonian model mice.

Example 48. Effects of Plasminogen on Body Weight and Fat Content in Obese Mice

Mice Model and Grouping

Fourteen 8-week-old male C57 mice were randomly divided into two groups based on the body weight, a blank control group of 4 mice and a model group of 10 mice. Mice in the blank control group were fed with a normal maintenance diet; mice in the model group were fed with a high-fat diet containing 45% fat calories (TP23000, Nantong Trophic Animal Feed High-Tech Co., Ltd.) for 12 weeks for model establishment, thereby establishing the obesity model[36]. The high-fat diet containing 45% fat calories herein is referred to as a high-calorie diet. After 12 weeks, mice in the model group were weighed and randomly divided into two groups again based on the body weight, 5 mice in each of a group administered with plasminogen and a control group administered with vehicle PBS. Human plasminogen was dissolved in PBS. The group administered with plasminogen was injected with human plasminogen at a dose of 1 mg/0.1 mL/mouse/day via the tail vein, and the control group administered with vehicle PBS was injected with an equal volume of PBS via the tail vein. The blank control group received no treatment. The above-mentioned experimental animals were administered for 28 consecutive days (the first day of administration was recorded as Day 1), and treated and detected as follows on Day 29.

Detections and Results

Detection of Body Weights

The above-mentioned experimental animals were weighed on Day 1 and Day 29 to calculate the changes in body weight. The results are shown as the value of the weight on Day 29 minus the weight on Day 1.

The results show that there is no significant body weight change in the blank control group, and the body weight in the group administered with plasminogen is significantly reduced than that in the control group administered with vehicle PBS with a significant statistical difference (* indicates P<0.05) (FIG. 48). It indicates that plasminogen can promote weight loss in obesity model mice.

Determination of Body Mass Index

On Day 29, the above-mentioned mice were weighed and measured for body length to calculate the body mass index. Body mass index=Weight (kg)/Body length (m).

Body mass index is a commonly used international standard to measure body fatness degree and health of human beings. Body mass index can also be used as an index of fatness degree in obesity model animals[37-38]. The results show that the body mass index of mice in the group administered with plasminogen is remarkably lower than that in the control group administered with vehicle PBS, and the statistical difference is significant (* indicates P<0.05, and ** indicates P<0.01); and compared with the control group administered with vehicle PBS, the body mass index of mice in the group administered with plasminogen is closer to that in the blank control group (FIG. 49). It indicates that plasminogen can significantly lower the body mass index of obesity model mice, and alleviate obesity.

Determination of Lee's Index

On Day 29, the above-mentioned mice were weighed and measured for body length to calculate the Lee's index.

$$\text{Lee's index} = \sqrt[3]{\text{body weight}(g)} / \text{Body length (cm)}.$$

Lee's index is an effective index for reflecting the degree of obesity[39-40]. The results show that the Lee's index of mice in the group administered with plasminogen is remarkably lower than that in the control group administered with vehicle PBS, and the statistical difference is significant (* indicates P<0.05); and compared with the control group administered with vehicle PBS, the Lee's index of mice in the group administered with plasminogen is closer to that in the blank control group (FIG. 50). It indicates that plasminogen can significantly lower the Lee's index of obesity model mice, and alleviate obesity.

Detection of Abdominal Fat Contents

On Day 29, the above-mentioned mice were weighed and sacrificed to weigh the abdominal fat. Abdominal fat coefficient (%)=(Abdominal fat mass/Body weight)*100.

The results show that the abdominal fat coefficient of mice in the group administered with plasminogen is remarkably lower than that in the control group administered with vehicle PBS with a significant statistical difference (* indicates P<0.05), and is close to the fat coefficient of mice in the blank control group (FIG. 51). It indicates that plasminogen can significantly reduce abdominal fat deposition in obesity model mice.

Detection of a Subcutaneous Fat Vacuolar Area in the Abdominal Cavity

The mice were sacrificed on day 29. The fat in abdominal cavities was fixed in 4% paraformaldehyde for 24 to 48 hours. The fixed tissue samples were paraffin-embedded after dehydration with alcohol gradient and permeabilization with xylene. The tissue sections were 4 µm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 200×. Image-pro plus image processing software was used to analyze the fat vacuolar area.

When the energy intake of an obese body exceeds the energy consumption, a large amount of lipid accumulates in adipose cells, leading to the expansion of adipose tissues, i.e., the enlargement of adipose cells and the increase of the fat vacuolar area[41].

Figure 52:
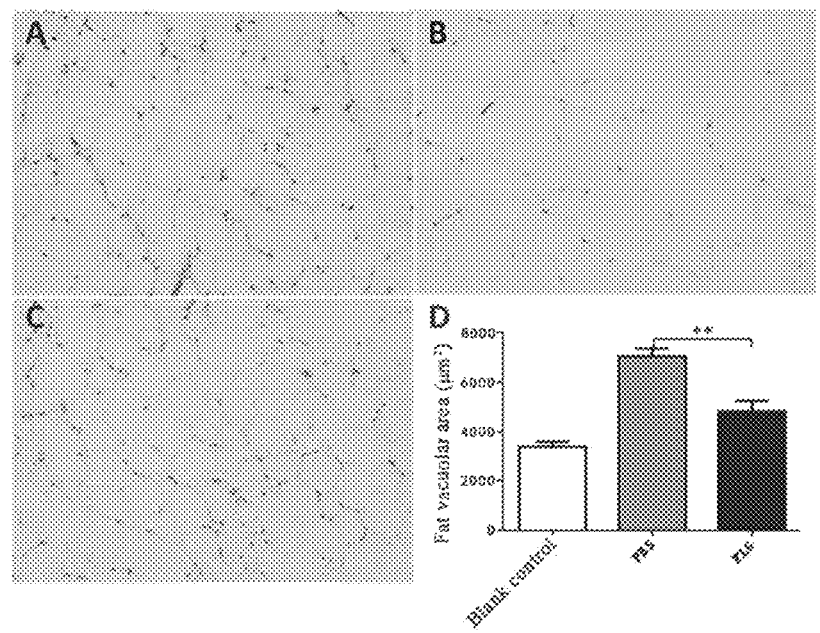

The results show that the fat vacuolar area of mice in the group administered with plasminogen (FIG. 52C) is remarkably less than that in the control group administered with vehicle PBS (FIG. 52B), and the statistical difference is extremely significant (** indicates P<0.01) (FIG. 52D); and compared with the control group administered with vehicle PBS, the fat vacuolar area of mice in the group administered with plasminogen is closer to that in the blank control group (FIG. 52A). It indicates that plasminogen can significantly reduce the size of adipose cells and abdominal fat deposition of obesity model mice.

Example 49. Study I on Plasminogen Reducing Lipid Deposition in the Livers

Ten 24- to 25-week-old male db/db mice were randomly divided into two groups, five in the control group administered with vehicle PBS and five in the group administered with plasminogen, respectively. The mice were weighed and grouped on the day when the experiment began, i.e. day 0. Plasminogen or PBS was administered from day 1. Mice in the group administered with plasminogen were injected with plasminogen at a dose of 2 mg/0.2 mL/mouse/day via the tail vein, and an equal volume of PBS was administered to mice in the control group administered with vehicle PBS via the tail vein, both lasting for 35 consecutive days. The mice were sacrificed on Day 36. The liver tissues were fixed in 4% paraformaldehyde for 24 to 48 hours, then sedimented in 15% and 30% sucrose at 4° C. overnight, respectively, and embedded in OCT. The frozen sections were 8 µm thick, stained with oil red 0 for 15 min, differentiated with 75% ethanol for 5 s followed by nuclear staining with hematoxylin for 30 s, and sealing with glycerine and gelatin. The sections were observed under an optical microscope at 200×.

Oil red O staining can show lipid deposition and reflect the extent of lipid deposition[42].

The staining results show that the lipid deposition area in liver of mice in the group administered with plasminogen (FIG. 53B) is significantly lower than that in the control group administered with vehicle PBS (FIG. 53A), and the statistical difference is significant (P=0.02) (FIG. 53C). It indicates that plasminogen can reduce fat deposition in liver of diabetic mice.

Example 50. Study II on Plasminogen Reducing Lipid Deposition in the Livers

Thirteen 6-week-old male ApoE mice were fed with a high-fat and high-cholesterol diet (Nantong TROPHIC, TP2031) for 16 weeks to induce an atherosclerosis model[31-32]. The model mice continued to be fed with a high-fat and high-cholesterol diet. 50 µL of blood was taken from each mouse three days before administration, and the total cholesterol (T-CHO) content was detected. The mice were randomly divided into two groups based on the T-CHO content, a control group of 7 mice administered with vehicle PBS, and a group of 6 mice administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. The mice continued to be fed with the model diet during administration. The mice were sacrificed on Day 31. The liver tissues were fixed in 4% paraformaldehyde for 24 to 48 hours, then sedimented in 15% and 30% sucrose at 4° C. overnight, respectively, and embedded in OCT. The frozen sections were 8 μm thick, stained with oil red 0 for 15 min, differentiated with 75% ethanol for 5 s, followed by nuclear staining with hematoxylin for 30 s, and sealing with glycerine and gelatin. The sections were observed under an optical microscope at 200×.

The staining results show that the fat deposition in liver of mice in the group administered with plasminogen (FIG. 54B) is remarkably lower than that in the control group administered with vehicle PBS (FIG. 54A), and the quantitative analysis shows a significant statistical difference (P=0.02) (FIG. 54C). It indicates that plasminogen can reduce fat deposition in liver of atherosclerosis model mice.

Example 51. Study III on Plasminogen Reducing Lipid Deposition in the Livers

Eleven 6-week-old male C57 mice were fed with a high-fat and high-cholesterol diet (Nantong TROPHIC, Cat #TP2031) for 16 weeks to induce a hyperlipemia model[29-30]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, a control group of 6 mice administered with vehicle PBS, and a group of 5 mice administered with plasminogen. The first day of administration was recorded as day 1. The group administered with plasminogen was injected with human plasminogen at a dose of 1 mg/0.1 mL/mouse/day via the tail vein, and mice in the control group administered with vehicle PBS was injected with an equal volume of PBS via the tail vein. The mice continued to be fed with the model diet during administration. The mice were administered for 30 days and sacrificed on Day 31. The livers were fixed in 4% paraformaldehyde for 24 to 48 hours, then sedimented in 15% and 30% sucrose at 4° C. overnight, respectively, and embedded in OCT. The frozen sections were 8 μm thick, stained with oil red 0 for 15 min, differentiated with 75% ethanol for 5 s, followed by nuclear staining with hematoxylin for 30 s, and sealing with glycerine and gelatin. The sections were observed under an optical microscope at 200×.

The results show that the fat deposition in liver of mice in the group administered with plasminogen (FIG. 55B) is remarkably lower than that in the control group administered with vehicle PBS (FIG. 55A), and the quantitative analysis shows a significant statistical difference (* indicates P<0.05) (FIG. 55C). It indicates that plasminogen can reduce fat deposition in liver of hyperlipemia model mice.

Example 52. Plasminogen Promotes Regeneration of the Medullary Sheath of the Corpus Callosum in Cuprizone-Induced Demyelination Model Mice Twenty 8-week-old male C57 mice were taken and randomly divided into two groups, 6 mice in the blank control group, and 14 mice in the model group. Mice in the blank control group were fed with a normal maintenance diet; mice in the model group were fed with a 0.2% cuprizone model diet (Nantong Trophic Animal Feed High-Tech Co., Ltd.) for 6 weeks to induce a demyelination model of mice[43]. After 6 weeks, mice in the model group were randomly divided into two groups again based on the body weight, 7 mice in each of a group administered with plasminogen and a control group administered with vehicle PBS. Mice in the group administered with plasminogen were injected with plasminogen at a dose of 1 mg/0.1 mL/mouse/day via the tail vein, and an equal volume of PBS was administered to mice in the control group administered with vehicle PBS in the same manner, both lasting for 14 consecutive days; and mice in the blank control group were not injected. All mice were fed with a normal maintenance diet during administration. The first day of administration was set as day 1. The mice were dissected on day 15, their brains were removed and fixed in 4% paraformaldehyde, dehydrated and embedded. The fixed tissue samples were paraffin-embedded after dehydration with alcohol gradient and permeabilization with xylene. The coronal sections of brain tissue were 3 μm thick. The sections were dewaxed and rehydrated, and LFB-stained with a medullary sheath staining solution. The sections were dehydrated with an alcohol gradient, permeabilized with xylene, and sealed with a neutral gum. The sections were observed and photographed under an optical microscope.

LFB (luxol fast blue) staining uses the fast blue staining method to dye the medullary sheath, and is an effective method to study the localization of corticospinal tract, and the morphological observation of lesions, injuries, regeneration and repair of the medullary sheath[44-45].

The results show that the morphology of medullary sheath of the corpus callosum in the blank control group (FIG. 56A) is basically normal, the positive staining (indicated by arrows) of the medullary sheath of the corpus callosum in the group administered with plasminogen (FIG. 56C) is remarkably more than that in the control group administered with vehicle PBS (FIG. 56B), and the statistical difference is significant (FIG. 56D) (* indicates P<0.05). This indicates that plasminogen can promote regeneration of the medullary sheath of the corpus callosum in cuprizone-induced demyelination model mice.

Example 53. Plasminogen Promotes Expression of Neurofilament Protein in Damaged Nerves Twenty 8-week-old male C57 mice were taken and randomly divided into two groups, 6 mice in the blank control group, and 14 mice in the model group. Mice in the blank control group were fed with a normal maintenance diet; mice in the model group were fed with a 0.2% cuprizone model diet (Nantong Trophic Animal Feed High-Tech Co., Ltd.) for 6 weeks to induce a demyelination model of mice[43]. After 6 weeks, mice in the model group were randomly divided into two groups again based on the body weight, 7 mice in each of a group administered with plasminogen and a control group administered with vehicle PBS. Mice in the group administered with plasminogen were injected with plasminogen at a dose of 1 mg/0.1 mL/mouse/day via the tail vein, and an equal volume of PBS was administered to mice in the control group administered with vehicle PBS in the same manner, both lasting for 14 consecutive days; and mice in the blank control group were not injected. All mice were fed with a normal maintenance diet during administration. The first day of administration was set as day 1. The mice were dissected on day 15, their brains were removed and fixed in 4% paraformaldehyde, dehydrated and embedded. The fixed tissue samples were paraffin-embedded after dehydration with alcohol gradient and permeabilization with xylene. The thickness of the brain tissue coronary sections was 3 μm. The sections were dewaxed and rehydrated and washed with water once. The sections were repaired with citric acid for 30 minutes, and gently rinsed with water after cooling at room temperature for 10 minutes. The sections were incubated with 3% hydrogen peroxide for 15 minutes, and the tissues were circled with a PAP pen. The sections were blocked with 10% goat serum solution (Vector laboratories, Inc., USA) for 1 hour, and after the time was up, the goat serum solution was discarded. The sections were incubated with rabbit-derived anti-NFP antibody (Abcam, ab207176) overnight at 4° C. and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washing with water three times, the sections were counterstained with hematoxylin for 30 seconds, returned to blue with running water for 5 minutes, and washed with PBS once. After dehydration with a gradient, permeabilization and sealing, the sections were observed under an optical microscope at 200×.

Neurofilament protein (NFP) is a protein that forms the intermediate filaments of axons in nerve cells. Its function is to provide elasticity so that nerve fibers are easy to stretch and are protected against rupture, and this protein is of great significance in maintaining cytoskeletons, stabilizing cell morphologies and in axon transport[46].

Figure 57:
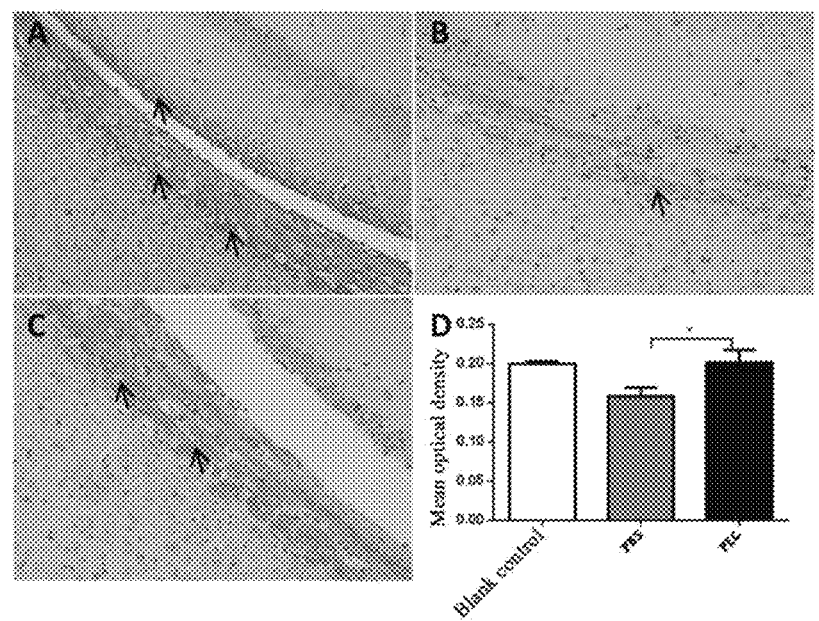

The results show that the expression of NFP (indicated by arrows) in the corpus callosum of mice in the group administered with plasminogen (FIG. 57C) is remarkably more than that in the control group administered with vehicle PBS (FIG. 57B), and the statistical difference is significant (* indicates P<0.05) (FIG. 57D); and compared with the control group administered with vehicle PBS, the expression of NFP in the corpus callosum in the group administered with plasminogen is closer to that in the blank control group (FIG. 57A). This indicates that plasminogen can promote expression of NFP, thereby promoting the regeneration of nerve fibers.

Example 54. Plasminogen Promotes Cutaneous Nerve Regeneration

Thirty female db/db mice were taken. Before the experiment, the mice were measured for non-fasting blood glucose (blood glucose was more than 15 mM) and weighed. The mice were randomly divided into two groups based on the blood glucose and body weight respectively, a control group administered with vehicle PBS and a group administered with plasminogen, with 15 mice in each group. All mice were anesthetized by intraperitoneal injection of pentobarbital sodium at 50 mg/kg body weight. After the mice were anesthetized, part of the hair was removed from the back. A copper block was heated to 95° C. to 100° C. in boiling water, removed and immediately touched vertically and gently on the depilation site of the mouse for 6 seconds without additional pressure, to set up a skin burn model[47]. Administration began 5 min after model establishment. Mice in the group administered with plasminogen were injected with plasminogen at a dose of 2 mg/0.2 mL/mouse/day via the tail vein, and an equal volume of PBS was administered to mice in the control group administered with vehicle PBS via the tail vein. The first day of administration was set as day 1. On days 4 and 8, five mice were taken from each of the two groups, and burned skin was taken after the mice were sacrificed. On day 15, the remaining mice were sacrificed and burned skin was taken. The skin was fixed in 4% paraformaldehyde for 24 to 48 hours, and paraffin-embedded. The thickness of the sections was 3 μm. The sections were dewaxed and rehydrated and washed with water once. The sections were repaired with citric acid for 30 minutes, and gently rinsed with water after cooling at room temperature for 10 minutes. The sections were incubated with 3% hydrogen peroxide for 15 minutes, and the tissues were circled with a PAP pen. The sections were blocked with 10% goat serum solution (Vector laboratories, Inc., USA) for 1 hour, and after the time was up, the goat serum solution was discarded. The sections were incubated with rabbit-derived anti-PGP 9.5 antibody (Abcam, ab10404) overnight at 4° C. and washed with PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washing with water three times, the sections were counterstained with hematoxylin for 30 seconds, returned to blue with running water for 5 minutes, and washed with PBS once. After dehydration with a gradient, permeabilization and sealing, the sections were observed under an optical microscope at 200×.

Protein gene product 9.5 (PGP 9.5) is a specific ubiquitin hydroxyhydrolase in nerve fibers, and serves as an axon marker; and an anti-PGP 9.5 antibody can bind to any unmyelinated or myelinated nerve fiber[48-49].

Figure 58:
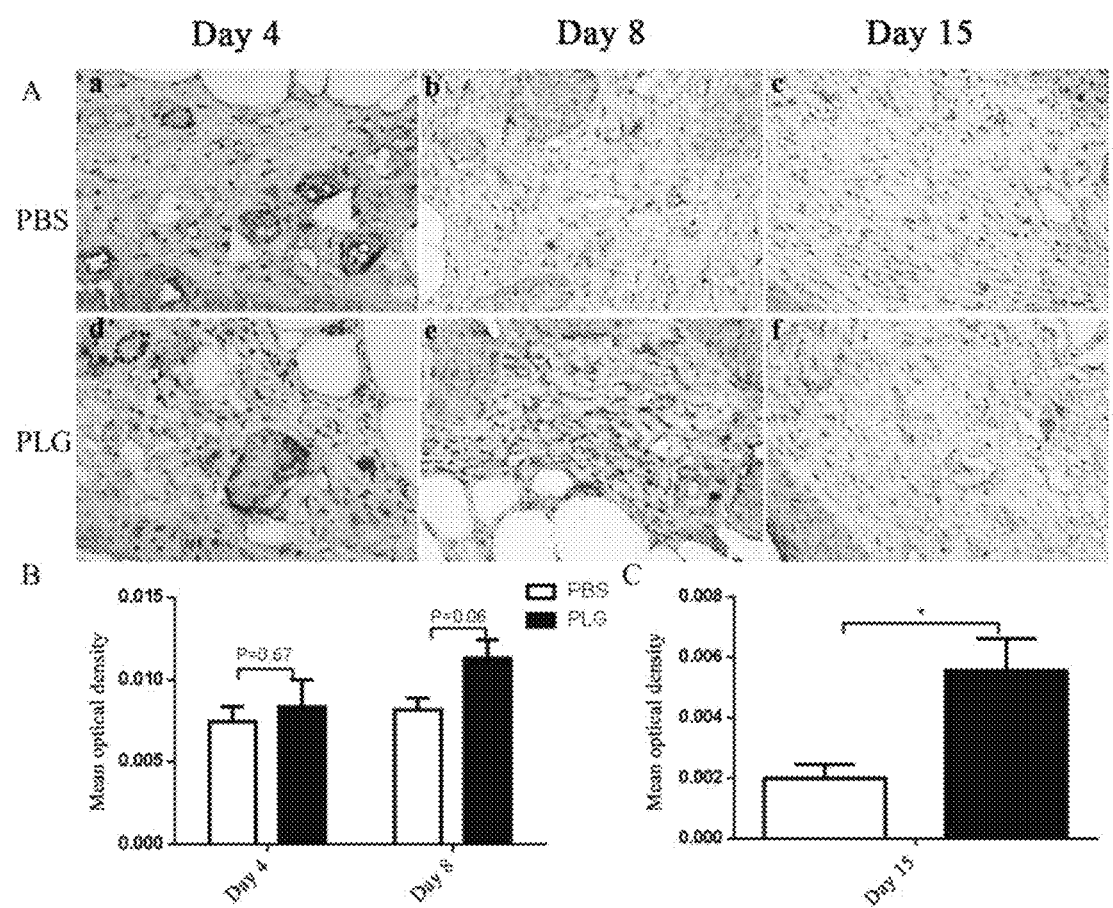

The results show that the positive expression of PGP 9.5 in the burned skin of mice in the group administered with plasminogen is higher than that in the control group administered with vehicle PBS, and the expression of PGP 9.5 in both groups of mice is nearly significantly different on day 8 of administration and significantly different on day 15 of administration (* indicates P<0.05) (FIG. 58). This indicates that plasminogen can promote nerve regeneration in diabetic burned skin. A are representative images of PGP 9.5 staining, wherein a-c are representative images of the control group administered with vehicle PBS on days 4, 8 and 15, respectively, d-f are representative images of the group administered with plasminogen on days 4, 8 and 15; B is the quantitative analysis result of immunostaining on days 4 and 8 of administration; and C is the quantitative analysis result on day 15 of administration.

REFERENCES

[1] Habener J F, Stanojevic V. a cells come of age. Trends Endocrinol Metab, 2013, 24: 153-163.
[2] Tura A, Muscelli E, Gastaldelli A et al. Altered pattern of the incretin effect as assessed by modeling in individuals with glucose tolerance ranging from normal to diabetic. Diabetologia, 2014, 57: 1199-1203.
[3] Kang Z F, Deng Y, Zhou Y et al. Pharmacological reduction of NEFA restores the efficacy of incretin-based therapies through GLP-1 receptor signaling in the beta cell in mouse models of diabetes. Diabetologia, 2013, 56: 423-433.
[4] Wilding J. Managing patients with type 2 diabetes and obesity. Practitioner, 2015, 259: 25-28.
[5] Perry T A, Greig N H. A new Alzheimer's disease interventive strategy: GLP-1 [J]. Curr Drug Targets, 2004, 5(6):565-571.
[6] During M J, Cao L, Zuzga D S et al. Glucagon-like peptide-1 receptor is involved in learning and neuroprotection[J]. Nat Med, 2003, 9 (9): 1173-1179.
[7] Gault V A, Holshcer C. GLP-1 agonists facilitate hippocampal LTP and reverse the impairment of LTP induced by beta-amyloid [J]. Eur J Pharmacol, 2008, 587:112-117.

[8] Wang X H, Li L, Holsher C et al. Val8-glucagon-like peptide-1 protects against ab1-40-induced impairment of hippocamapllate-phase long-term potentiation and spatial learning in rats [J]. Neuroscience, 2010, 170:1239-1248.

[9] Holscher C. Incretin anlogues that have been developed to treat type 2 diabetes hold promise as a novel treatment strategy for Alzheimer's disease [J]. Recent Pat CNS Drug Discov, 2010, 5:109-117.

[10] Jensterle M, Pirs B, Goricar K et al. Genetic variability in GLP-1 receptor is associated with inter-individual differences in weight lowering potential of liraglutide in obese women with PCOS: a pilot study. Eur J Clin Pharmacol, 2015 May 21.

[11] Marder V J, Novokhatny V. Direct fibrinolytic agents: biochemical attributes, preclinical foundation and clinical potential [J]. Journal of Thrombosis and Haemostasis, 2010, 8(3): 433-444.

[12] Hunt J A, Petteway Jr S R, Scuderi P, et al. Simplified recombinant plasmin: production and functional comparison of a novel thrombolytic molecule with plasma-derived plasmin [J]. Thromb Haemost, 2008, 100(3): 413-419.

[13] Duboscq Cl, Genoud V, Parborell M F et al. Impaired clot lysis by rt-PA catalyzed mini-plasminogen activation. Thromb Res. 1997 Jun. 15; 86(6):505-13.

[14] Nagai N, Demarsin E, Van Hoef B, et al. Recombinant human microplasmin: production and potential therapeutic properties [J]. Journal of Thrombosis and Haemostasis, 2003, 1(2): 307-313.

[15] KennethC Robbins, Louis Summaria, David Elwyn et al. Further Studies on the Purification and Characterization of Human Plasminogen and Plasmin. Journal of Biological Chemistry, 1965, 240 (1):541-550.

[16] Summaria L, Spitz F, Arzadon L et al. Isolation and characterization of the affinity chromatography forms of human Glu- and Lys-plasminogens and plasmins. J Biol Chem. 1976 Jun. 25; 251(12):3693-9.

[17] HAGAN J J, ABLONDI F B, D E RENZO E C. Purification and biochemical properties of human plasminogen. J Biol Chem. 1960 April; 235:1005-10.

[18] Ghinwa Barakat, Mohamed E Moustafa, Ibrahim Khalifeh ea al. Effects of exendin-4 and selenium on the expression of GLP-1R,IRS-1, and preproinsulin in the pancreas of diabetic rats. J Physiol Biochem. 2017 Jun. 7.

[19] Brian L. Furman. Streptozotocin-Induced Diabetic Models UNIT 5. 47 in Mice and Rats. Curr. Protoc. Pharmacol. 70:5. 47. 1-5. 47. 20.

[20] Parvesh Chaudhry, Mohan Singh, Sophie Parent et al. Prostate Apoptosis Response 4 (Par-4), a Novel Substrate of Caspase-3 during Apoptosis Activation. Mol Cell Biol. 2012 February; 32(4): 826-839.

[21] Patrick Viatour, Marie-Paule Merville, Vincent Bours et al. Phosphorylation of NF-kB and IkBproteins: implications in cancer and inflammation. TRENDS in Biochemical Sciences, 2005, 30 (1):43-52.

[22] Withers D J, Gutierrez J S, Towery H, et al. Disruption of IRS-2 causes type 2diabetes in mice. Nature 1998; 391:900-904.

[23] Withers D J, Burks D J, Towery H H et al. White M F. Irs-2 coordinates Igf-1 receptor-mediated beta-cell development and peripheral insulin signalling. Nat Genet 1999; 23:32-40.

[24] Jacob C O1, Aiso S, Michie S A, McDevitt H O et al. Prevention of diabetes in nonobese diabetic mice by tumor necrosis factor (TNF): similarities between TNF-alpha and interleukin 1 Proc Natl Acad Sci USA. 1990 February; 87(3):968-72.

[25] Zhang M, Takahashi K, Alicot E M, Vorup-Jensen T, Kessler B, et al. Activation of the lectin pathway by natural IgM in a model of ischemia/reperfusion injury. J Immunol.2006. 177: 4727-4734.

[26] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement Activation. The Journal of Experimental Medicine 196: 655-665.

[27] D J Drucker, J Philippe, S Mojsov et al. Glucagon-like peptide I stimulates insulin gene expression and increases cyclic AMP levels in a rat islet cell line. Proc Natl Acad Sci USA. 1987 May; 84(10): 3434-3438.

[28] Mojsov S, Weir G C, Habener J F. Insulinotropin: glucagon-like peptide I (7-37) co-encoded in the glucagon gene is a potent stimulator of insulin release in the perfused rat pancreas. J Clin Invest. 1987 February; 79(2):616-9.

[29] Dominika Nackiewicz, Paromita Dey, Barbara Szczerba et al. Inhibitor of differentiation 3, a transcription factor regulates hyperlipidemia associated kidney disease. Nephron Exp Nephrol. 2014; 126(3): 141-147.

[30] Ming Gul, Yu Zhang., Shengjie Fan et al. Extracts of Rhizoma Polygonati Odorati Prevent High-Fat Diet-Induced Metabolic Disorders in C57BL/6 Mice. PLoS ONE 8(11): e81724.

[31] Yutaka Nakashima, Andrew S. Plump, Elaine W. Raines et al. Arterioscler Thromb. 1994 January; 14(1): 133-40.

[32] Yvonne Nitschke, Gabriele Weissen-Plenz, Robert Terkeltaub et al. Nppl promotes atherosclerosis in ApoE knockout mice. J. Cell. Mol. Med. Vol 15, No 11, 2011 pp. 2273-2283.

[33] Vernice Jackson-Lewisl & Serge Przedborski, Protocol for the MPTP mouse model of Parkinson's Disease, Nature protocols VOL.2 NO.1, 2007(141)

[34] N. A. Tatton and S. J. Kish, In situ detection of apoptotic nuclei in the substantia aigra compacta of 1-methyl-4-phenyl-1,2,3,6-tetrahydropyridine-treated mice using terminal deoxynucleotidyl transferase labeling and acridine orange staining. Neuroscience Vol. 77, No. 4, pp. 1037-1048, 1997.

[35] Li, Y., Perry, T., Kindy, M. S et al. (2009). GLP-1 receptor stimulation preserves primary cortical and dopaminergic neurons in cellular and rodent models of stroke and Parkinsonism. Proc. Natl. Acad. Sci. USA 106, 1285-1290.

[36] Eun Young Lee, Yeon Wook Kim, Anti-obesity effects of KR-66195, a synthetic DPP-IVinhibitor, in diet-induced obese mice and obese-diabetic ob/ob mice, Metabolism chlinical and experimental 63(2014)793-799.

[37] Duan D M, Wu S, Hsu L A et al. Associations between TRPV4 genotypes and body mass index in Taiwanese subjects. Mol Genet Genomics. 2015 August; 290(4): 1357-65.

[38] Goossens G H. The role of adipose tissue dysfunction in the pathogenesis of obesity-related insulin resistance. Physiol Behay. 2008 May 23; 94(2):206-18.

[39] Yang Z, Li W, He C. Potential effect of chronic *Helicobacter pylori* infection on glucose metabolism of Mongolian gerbils. World J Gastroenterol. 2015 Nov. 28; 21(44):12593-604.

[40] Hu Y, Rosa G J, Gianola D. A GWAS assessment of the contribution of genomic imprinting to the variation of body mass index in mice. BMC Genomics. 2015 Aug. 5; 16:576.

[41] Goossens G H. The role of adipose tissue dysfunction in the pathogenesis of obesity-related insulin resistance. Physiol Behav. 2008 May 23; 94(2):206-18.

[42] Siobhan M. Craige, PhD, Shashi Kant et al. Endothelial NADPH oxidase 4 protects ApoE-/- mice from atherosclerotic lesions. Free Radic Biol Med. 2015 December; 89: 1-7.

[43] M. Lindner, S. Heine, K. Haastert et al. Sequential myelin protein expression during remyelination reveals fast and efficient repair after central nervous system demyelination, Neuropathology and Applied Neurobiology (2008), 34, 105-114.

[44] Sun S W, Liang H F, Trinkaus K et al. Noninvasive detection of cuprizone induced axonal damage and demyelination in the mouse corpus callosum. Magn Reson Med. 2006 February; 55(2):302-8.

[45] Vallières N1, Berard J L, David S et al. Systemic injections of lipopolysaccharide accelerates myelin phagocytosis during Wallerian degeneration in the injured mouse spinal cord. Glia. 2006 Jan. 1; 53(1):103-13.

[46] Gotow T. Neurofilaments in health and disease. Med Electron Microsc. 2000; 33(4):173-99.

[47] Yue Shen, Yongzhi Guo, Peter Mikus et al. Plasminogen is a key proinflammatory regulator that accelerates the healing of acute and diabetic wounds. Blood. 2012 Jun. 14; 119(24):5879-87.

[48] Hasan W1, Cowen T, Barnett P S et al. The sweating apparatus in growth hormone deficiency, following treatment with r-hGH and in acromegaly. Auton Neurosci. 2001 Jun. 20; 89(1-2):100-9.

[49] Loo L S1, Ng Y K, Zhu Y Z et al. Cortical expression of endothelin receptor subtypes A and B following middle cerebral artery occlusion in rats. Neuroscience. 2002; 112(4):993-1000.

The invention claimed is:

1. A method for treating a disease by regulating GLP-1/GLP-1R, comprising administering an effective amount of plasminogen to a subject, wherein the disease is obesity, osteoporosis, Parkinson's syndrome, lateral sclerosis of the spinal cord, inflammatory bowel disease, dyspepsia, or gastrointestinal ulcer.

2. The method of claim 1, wherein the plasminogen promotes expression of GLP-1 and/or GLP-1R.

3. The method of claim 1, wherein the plasminogen is a protein having at least 80%, 85%, 90%, 95%, 96%, 97%, 98% or 99% sequence identity with SEQ ID No. 2.

4. The method of claim 1, wherein the plasminogen is a protein that comprises a plasminogen active fragment as shown by SEQ ID No. 14 and still has the plasminogen activity.

5. The method of claim 1, wherein the plasminogen is selected from Glu-plasminogen, Lys-plasminogen, mini-plasminogen, micro-plasminogen, delta-plasminogen or their variants that retain the plasminogen activity.

6. The method of claim 1, wherein the plasminogen is administered in combination with one or more other drugs or therapies.

7. The method of claim 6, wherein the plasminogen is administered in combination with one or more drugs or therapies selected from a drug or therapy for treating Parkinson's disease and an anti-infective drug or therapy.

8. The method of claim 2, wherein the plasminogen is a protein having at least 80%, 85%, 90%, 95%, 96%, 97%, 98% or 99% sequence identity with SEQ ID No. 2.

9. The method of claim 2, wherein the plasminogen is a protein that comprises a plasminogen active fragment as shown by SEQ ID No. 14 and still has the plasminogen activity.

10. A method for treating a GLP-1/GLP-1R-related condition, comprising administering an effective amount of plasminogen to a subject;
wherein the GLP-1/GLP-1R-related condition comprises one or more of: obesity, osteoporosis, Parkinson's syndrome, lateral sclerosis, inflammatory bowel disease, dyspepsia, or gastrointestinal ulcer.

11. The method of claim 10, wherein the plasminogen is a protein having at least 80%, 85%, 90%, 95%, 96%, 97%, 98% or 99% sequence identity with SEQ ID No. 2.

12. The method of claim 10, wherein the plasminogen is a protein that comprises a plasminogen active fragment as shown by SEQ ID No. 14 and still has the plasminogen activity.

13. The method of claim 10, wherein the plasminogen promotes expression of GLP-1 and/or GLP-1R.

14. The method of claim 13, wherein the plasminogen is a protein having at least 80%, 85%, 90%, 95%, 96%, 97%, 98% or 99% sequence identity with SEQ ID No. 2.

15. The method of claim 13, wherein the plasminogen is a protein that comprises a plasminogen active fragment as shown by SEQ ID No. 14 and still has the plasminogen activity.

16. The method of claim 10, wherein the plasminogen is selected from Glu-plasminogen, Lys-plasminogen, mini-plasminogen, micro-plasminogen, delta-plasminogen or their variants that retain the plasminogen activity.

17. The method of claim 10, wherein the plasminogen is administered in combination with one or more other drugs or therapies.

18. The method of claim 17, wherein the plasminogen is administered in combination with one or more drugs or therapies selected from a drug or therapy for treating Parkinson's disease-and an anti-infective drug or therapy.

* * * * *

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial sequence
<220> FEATURE:
<223> OTHER INFORMATION: nucleotide sequence coding for the natural
      plasminogen(Glu-PLG,Glu-plasminogen)without the signal peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggaatgtat gcattgcagt ggagaaaact atgacggcaa atttccaag     540 accatgtctg gactggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact ttgtgacatc     720
ccccgctgca acacacctcc accatcttct ggtcccacct accagtgtct gaagggaaca     780
ggtgaaaact atcgcgggaa tgtggctgtt accgtgtccg ggcacacctg tcagcactgg     840
agtgcacaga cccctcacac acataacagg acaccagaaa acttcccctg caaaaatttg     900
gatgaaaact actgccgcaa tcctgacgga aaagggccc atggtgcca taaccaac       960 agccaagtgc ggtgggagta ctgtaagata ccgtcctgtg actcctcccc agtatccacg    1020
gaacaattgg ctcccacagc accacctgag ctaacccctg tggtccagga ctgctaccat    1080
ggtgatggac agagctaccg aggcacatcc tccaccacca cacaggaaa gaagtgtcag    1140 tcttggtcat ctatgacacc acaccggcac cagaagaccc cagaaaacta cccaaatgct    1200
ggcctgacaa tgaactactg caggaatcca gatgccgata aggccctg gtgtttacc    1260 acagacccca gcgtcaggtg ggagtactgc aacctgaaaa aatgctcagg aacagaagcg    1320
```

-continued

```
agtgttgtag cacctccgcc tgttgtcctg cttccagatg tagagactcc ttccgaagaa   1380
gactgtatgt ttgggaatgg gaaaggatac cgaggcaaga gggcgaccac tgttactggg   1440
acgccatgcc aggactgggc tgcccaggag ccccatagac acagcatttt cactccagag   1500
acaaatccac gggcgggtct ggaaaaaaat tactgccgta accctgatgg tgatgtaggt   1560
ggtccctggt gctacacgac aaatccaaga aaactttacg actactgtga tgtccctcag   1620
tgtgcggccc cttcatttga ttgtgggaag cctcaagtgg agccgaagaa atgtcctgga   1680
agggttgtag gggggtgtgt ggcccaccca cattcctggc cctggcaagt cagtcttaga   1740
acaaggtttg gaatgcactt ctgtggaggc accttgatat ccccagagtg ggtgttgact   1800
gctgcccact gcttggagaa gtccccaagg ccttcatcct acaaggtcat cctgggtgca   1860
caccaagaag tgaatctcga accgcatgtt caggaaatag aagtgtctag gctgttcttg   1920
gagcccacac gaaaagatat tgccttgcta aagctaagca gtcctgccgt catcactgac   1980
aaagtaatcc cagcttgtct gccatcccca aattatgtgg tcgctgaccg gaccgaatgt   2040
ttcatcactg gctggggaga aacccaaggt acttttggag ctggccttct caaggaagcc   2100
cagctccctg tgattgagaa taaagtgtgc aatcgctatg agtttctgaa tggaagagtc   2160
caatccaccg aactctgtgc tgggcatttg gccggaggca ctgacagttg ccagggtgac   2220
agtggaggtc ctctggtttg cttcgagaag gacaaataca ttttacaagg agtcacttct   2280
tggggtcttg gctgtgcacg ccccaataag cctggtgtct atgttcgtgt ttcaaggttt   2340
gttacttgga ttgagggagt gatgagaaat aattaa                            2376
```

<210> SEQ ID NO 2
<211> LENGTH: 791
<212> TYPE: PRT
<213> ORGANISM: Artificial sequence
<220> FEATURE:
<223> OTHER INFORMATION: amino acid sequence of the natural plasminogen
    (Glu-PLG,Glu-plasminogen) without the signal peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175
```

```
Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
            245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
        370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
            405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
            565                 570                 575

Val Ser Leu Arg Thr Arg Phe Gly Met His Phe Cys Gly Gly Thr Leu
            580                 585                 590
```

```
Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
        610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790

<210> SEQ ID NO 3
<211> LENGTH: 2433
<212> TYPE: DNA
<213> ORGANISM: Artificial sequence
<220> FEATURE:
<223> OTHER INFORMATION: nucleotide sequence coding for the natural
      plasminogen(from swiss prot)with the signal peptide

<400> SEQUENCE: 3
atggaacata aggaagtggt tcttctactt cttttatttc tgaaatcagg tcaaggagag        60
cctctggatg actatgtgaa tacccagggg gcttcactgt tcagtgtcac taagaagcag      120
ctgggagcag gaagtataga agaatgtgca gcaaaatgtg aggaggacga agaattcacc      180
tgcagggcat ccaatatcca gtaaagag caacaatgtg tgataatggc tgaaaacagg       240
aagtcctcca taatcattag gatgagagat gtagttttat ttgaaaagaa agtgtatctc      300
tcagagtgca agactgggaa tggaaagaac tacagaggga cgatgtccaa aacaaaaaat      360
ggcatcacct gtcaaaaatg gagttccact tctccccaca gacctagatt ctcacctgct      420
acacacccct cagagggact ggaggagaac tactgcagga atccagacaa cgatccgcag      480
gggccctggt gctatactac tgatccagaa aagagatatg actactgcga cattcttgag      540
tgtgaagagg aatgtatgca ttgcagtgga gaaaactatg acggcaaaat ttccaagacc      600
atgtctggac tggaatgcca ggcctggac tctcagagcc acacgctca tggatacatt       660 ccttccaaat ttccaaacaa gaacctgaag aagaattact gtcgtaaccc cgatagggag      720
ctgcggcctt ggtgtttcac caccgacccc aacaagcgct gggaactttg tgacatcccc      780
cgctgcacaa cacctccacc atcttctggt cccacctacc agtgtctgaa gggaacaggt      840
gaaaactatc gcgggaatgt ggctgttacc gtgtccgggc acacctgtca gcactggagt      900
```

-continued

```
gcacagaccc ctcacacaca taacaggaca ccagaaaact tccccctgcaa aaatttggat    960
gaaaactact gccgcaatcc tgacggaaaa agggccccat ggtgccatac aaccaacagc   1020
caagtgcggt gggagtactg taagataccg tcctgtgact cctccccagt atccacggaa   1080
caattggctc ccacagcacc acctgagcta acccctgtgg tccaggactg ctaccatggg   1140
gatggacaga gctaccgagg cacatcctcc accaccacca caggaaagaa gtgtcagtct   1200
tggtcatcta tgcaccacca ccggcaccag aagaccccag aaaactaccc aaatgctggc   1260
ctgacaatga actactgcag gaatccagat gccgataaag cccctggtg ttttaccaca    1320
gaccccagcg tcaggtggga gtactgcaac ctgaaaaaat gctcaggaac agaagcgagt   1380
gttgtagcac ctccgcctgt tgtcctgctt ccagatgtag agactcctc cgaagaagac    1440
tgtatgtttg ggaatgggaa aggataccga ggcaagaggg cgaccactgt tactgggacg   1500
ccatgccagg actgggctgc ccaggagccc catagacaca gcattttcac tccagagaca   1560
aatccacggg cggtctgga aaaaaattac tgccgtaacc ctgatggtga tgtaggtggt    1620
ccctggtgct acacgacaaa tccaagaaaa ctttacgact actgtgatgt ccctcagtgt   1680
gcggccccttt catttgattg tgggaagcct caagtggagc cgaagaaatg tcctggaagg   1740
gttgtagggg ggtgtgtggc ccacccacat tcctggcct ggcaagtcag tcttagaaca    1800
aggtttggaa tgcacttctg tgaggcacc ttgatatccc cagagtgggt gttgactgct    1860
gcccactgct tggagaagtc cccaaggcct tcatcctaca aggtcatcct gggtgcacac   1920
caagaagtga atctcgaacc gcatgttcag gaaatagaag tgtctaggct gttcttggag   1980
cccacacgaa aagatattgc cttgctaaag ctaagcagtc ctgccgtcat cactgacaaa   2040
gtaatcccag cttgtctgcc atccccaaat tatgtggtcg ctgaccggac cgaatgtttc   2100
atcactggct ggggagaaac ccaaggtact tttggagctg gccttctcaa ggaagcccag   2160
ctccctgtga ttgagaataa agtgtgcaat cgctatgagt ttctgaatgg aagagtccaa   2220
tccaccgaac tctgtgctgg gcatttggcc ggaggcactg acagttgcca gggtgacagt   2280
ggaggtcctc tggtttgctt cgagaaggac aaatacattt tacaaggagt cacttcttgg   2340
ggtcttggct gtgcacgccc caataagcct ggtgtctatg ttcgtgtttc aaggtttgtt   2400
acttggattg agggagtgat gagaaataat taa                                2433
```

```
<210> SEQ ID NO 4
<211> LENGTH: 810
<212> TYPE: PRT
<213> ORGANISM: Artificial sequence
<220> FEATURE:
<223> OTHER INFORMATION: amino acid sequence coding for the natural
      plasminogen(from swiss prot)with the signal peptide

<400> SEQUENCE: 4

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80
```

```
Lys Ser Ser Ile Ile Arg Met Arg Asp Val Val Leu Phe Glu Lys
                85                  90                  95
Lys Val Tyr Leu Ser Glu Cys Lys Thr Gly Asn Gly Lys Asn Tyr Arg
            100                 105                 110
Gly Thr Met Ser Lys Thr Lys Asn Gly Ile Thr Cys Gln Lys Trp Ser
            115                 120                 125
Ser Thr Ser Pro His Arg Pro Arg Phe Ser Pro Ala Thr His Pro Ser
        130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Cys Met His Cys Ser Gly Glu Asn
                180                 185                 190
Tyr Asp Gly Lys Ile Ser Lys Thr Met Ser Gly Leu Glu Cys Gln Ala
            195                 200                 205
Trp Asp Ser Gln Ser Pro His Ala His Gly Tyr Ile Pro Ser Lys Phe
        210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
                260                 265                 270
Tyr Gln Cys Leu Lys Gly Thr Gly Glu Asn Tyr Arg Gly Asn Val Ala
            275                 280                 285
Val Thr Val Ser Gly His Thr Cys Gln His Trp Ser Ala Gln Thr Pro
290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
        355                 360                 365
Glu Leu Thr Pro Val Val Gln Asp Cys Tyr His Gly Asp Gly Gln Ser
            370                 375                 380
Tyr Arg Gly Thr Ser Ser Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
450                 455                 460
Pro Pro Val Val Leu Leu Pro Asp Val Glu Thr Pro Ser Glu Glu Asp
        465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
```

500             505             510
His Ser Ile Phe Thr Pro Glu Thr Asn Pro Arg Ala Gly Leu Glu Lys
        515             520             525

Asn Tyr Cys Arg Asn Pro Asp Gly Asp Val Gly Gly Pro Trp Cys Tyr
        530             535             540

Thr Thr Asn Pro Arg Lys Leu Tyr Asp Tyr Cys Asp Val Pro Gln Cys
545             550             555             560

Ala Ala Pro Ser Phe Asp Cys Gly Lys Pro Gln Val Glu Pro Lys Lys
                565             570             575

Cys Pro Gly Arg Val Val Gly Gly Cys Val Ala His Pro His Ser Trp
            580             585             590

Pro Trp Gln Val Ser Leu Arg Thr Arg Phe Gly Met His Phe Cys Gly
        595             600             605

Gly Thr Leu Ile Ser Pro Glu Trp Val Leu Thr Ala Ala His Cys Leu
            610             615             620

Glu Lys Ser Pro Arg Pro Ser Ser Tyr Lys Val Ile Leu Gly Ala His
625             630             635             640

Gln Glu Val Asn Leu Glu Pro His Val Gln Glu Ile Glu Val Ser Arg
                645             650             655

Leu Phe Leu Glu Pro Thr Arg Lys Asp Ile Ala Leu Leu Lys Leu Ser
            660             665             670

Ser Pro Ala Val Ile Thr Asp Lys Val Ile Pro Ala Cys Leu Pro Ser
            675             680             685

Pro Asn Tyr Val Val Ala Asp Arg Thr Glu Cys Phe Ile Thr Gly Trp
            690             695             700

Gly Glu Thr Gln Gly Thr Phe Gly Ala Gly Leu Leu Lys Glu Ala Gln
705             710             715             720

Leu Pro Val Ile Glu Asn Lys Val Cys Asn Arg Tyr Glu Phe Leu Asn
            725             730             735

Gly Arg Val Gln Ser Thr Glu Leu Cys Ala Gly His Leu Ala Gly Gly
                740             745             750

Thr Asp Ser Cys Gln Gly Asp Ser Gly Gly Pro Leu Val Cys Phe Glu
            755             760             765

Lys Asp Lys Tyr Ile Leu Gln Gly Val Thr Ser Trp Gly Leu Gly Cys
            770             775             780

Ala Arg Pro Asn Lys Pro Gly Val Tyr Val Arg Val Ser Arg Phe Val
785             790             795             800

Thr Trp Ile Glu Gly Val Met Arg Asn Asn
            805             810

<210> SEQ ID NO 5
<211> LENGTH: 2145
<212> TYPE: DNA
<213> ORGANISM: Artificial sequence
<220> FEATURE:
<223> OTHER INFORMATION: nucleotide sequence coding for LYS77-PLG(Lys-
      plasminogen)

<400> SEQUENCE: 5
aaagtgtatc tctcagagtg caagactggg aatggaaaga actacagagg gacgatgtcc      60
aaaacaaaaa atggcatcac ctgtcaaaaa tggagttcca cttctcccca cagacctaga     120
ttctcacctg ctacacaccc ctcagaggga ctggaggaga actactgcag gaatccagac     180
aacgatccgc aggggccctg tgctatact actgatccag aaaagagata tgactactgc     240
gacattcttg agtgtgaaga ggaatgtatg cattgcagtg gagaaaacta tgacggcaaa     300

```
atttccaaga ccatgtctgg actggaatgc caggcctggg actctcagag cccacacgct    360
catggataca ttccttccaa atttccaaac aagaacctga agaagaatta ctgtcgtaac    420
cccgataggg agctgcggcc ttggtgtttc accaccgacc ccaacaagcg ctgggaactt    480
tgtgacatcc cccgctgcac aacacctcca ccatcttctg gtcccaccta ccagtgtctg    540
aagggaacag gtgaaaacta tcgcgggaat gtggctgtta ccgtgtccgg cacacctgt    600 cagcactgga gtgcacagac ccctcacaca cataacagga caccagaaaa cttcccctgc    660
aaaaatttgg atgaaaacta ctgccgcaat cctgacggaa aaagggcccc atggtgccat    720
acaaccaaca gccaagtgcg gtgggagtac tgtaagatac cgtcctgtga ctcctcccca    780
gtatccacgg aacaattggc tcccacagca ccacctgagc taacccctgt ggtccaggac    840
tgctaccatg gtgatggaca gagctaccga ggcacatcct ccaccaccac acaggaaaag    900
aagtgtcagt cttggtcatc tatgacacca caccggcacc agaagacccc agaaaactac    960
ccaaatgctg gcctgacaat gaactactgc aggaatccag atgccgataa aggcccctgg   1020
tgttttacca cagaccccag cgtcaggtgg gagtactgca acctgaaaaa atgctcagga   1080
acagaagcga gtgttgtagc acctccgcct gttgtcctgc ttccagatgt agagactcct   1140
tccgaagaag actgtatgtt tgggaatggg aaaggatacc gaggcaagag ggcgaccact   1200
gttactggga cgccatgcca ggactgggct gcccaggagc ccatagaca cagcattttc   1260 actccagaga caaatccacg gcgggtctg gaaaaaaatt actgccgtaa ccctgatggt   1320
gatgtaggtg gtccctggtg ctacacgaca atccaagaa aactttacga ctactgtgat   1380
gtccctcagt gtgcggcccc ttcatttgat tgtgggaagc tcaagtgga gccgaagaaa   1440 tgtcctggaa gggttgtagg ggggtgtgtg gcccacccac attcctggcc ctggcaagtc   1500
agtcttagaa caaggtttgg aatgcacttc tgtggaggca ccttgatatc cccagagtgg   1560
gtgttgactg ctgcccactg cttggagaag tccccaaggc cttcatccta caaggtcatc   1620
ctgggtgcac accaagaagt gaatctcgaa ccgcatgttc aggaaataga agtgtctagg   1680
ctgttcttgg agcccacacg aaaagatatt gccttgctaa agctaagcag tcctgccgtc   1740
atcactgaca aagtaatccc agcttgtctg ccatccccaa attatgtggt cgctgaccgg   1800
accgaatgtt tcatcactgg ctggggagaa acccaaggta cttttggagc tggccttctc   1860
aaggaagccc agtccctgt gattgagaat aaagtgtgca atcgctatga gtttctgaat   1920
ggaagagtcc aatccaccga actctgtgct gggcatttgg ccggaggcac tgacagttgc   1980
cagggtgaca gtgaggtcc tctggttgc ttcgagaagg acaaatacat tttacaagga   2040
gtcacttctt ggggtcttgg ctgtgcacgc cccaataagc ctggtgtcta tgttcgtgtt   2100
tcaaggtttg ttacttggat tgagggagtg atgagaaata attaa                  2145
```

<210> SEQ ID NO 6
<211> LENGTH: 714
<212> TYPE: PRT
<213> ORGANISM: Artificial sequence
<220> FEATURE:
<223> OTHER INFORMATION: amino acid sequence of LYS77-PLG(Lys-
      plasminogen)

<400> SEQUENCE: 6

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

```
Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
            130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
            210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
            245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Gly Lys Lys Cys Gln Ser
290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
            325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
            370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
            405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
            435                 440                 445
```

```
Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
                500                 505                 510

Gly Thr Leu Ile Ser Pro Glu Trp Val Leu Thr Ala Ala His Cys Leu
                515                 520                 525

Glu Lys Ser Pro Arg Pro Ser Ser Tyr Lys Val Ile Leu Gly Ala His
530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
                580                 585                 590

Pro Asn Tyr Val Val Ala Asp Arg Thr Glu Cys Phe Ile Thr Gly Trp
                595                 600                 605

Gly Glu Thr Gln Gly Thr Phe Gly Ala Gly Leu Leu Lys Glu Ala Gln
                610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
                660                 665                 670

Lys Asp Lys Tyr Ile Leu Gln Gly Val Thr Ser Trp Gly Leu Gly Cys
                675                 680                 685

Ala Arg Pro Asn Lys Pro Gly Val Tyr Val Arg Val Ser Arg Phe Val
                690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial sequence
<220> FEATURE:
<223> OTHER INFORMATION: nucleotide sequence coding for delta-plg(delta-
      plasminogen)

<400> SEQUENCE: 7
gagcctctgg atgactatgt gaatacccag ggggcttcac tgttcagtgt cactaagaag     60
cagctgggag caggaagtat agaagaatgt gcagcaaaat gtgaggagga cgaagaattc    120
acctgcaggg cattccaata tcacagtaaa agcaacaat gtgtgataat ggctgaaaac     180
aggaagtcct ccataatcat taggatgaga gatgtagttt atttgaaaaa gaaagtgtat    240
ctctcagagt gcaagactgg aatggaaag aactacagag gacgatgtc caaaacaaaa     300 aatggcatca cctgtcaaaa atggagttcc acttctcccc acagacctag attctcacct    360
gctacacacc cctcagaggg actggaggag aactactgca ggaatccaga caacgatccg    420
caggggccct ggtgctatac tactgatcca gaaaagagat atgactactg cgacattctt    480
gagtgtgaag aggcggcccc ttcatttgat tgtgggaagc ctcaagtgga gccgaagaaa    540
```

```
tgtcctggaa gggttgtagg ggggtgtgtg gcccacccac attcctggcc ctggcaagtc    600
agtcttagaa caaggtttgg aatgcacttc tgtggaggca ccttgatatc ccagagtgg     660 gtgttgactg ctgcccactg cttggagaag tccccaaggc cttcatccta caaggtcatc    720
ctgggtgcac accaagaagt gaatctcgaa ccgcatgttc aggaaataga agtgtctagg    780
ctgttcttgg agcccacacg aaaagatatt gccttgctaa agctaagcag tcctgccgtc    840
atcactgaca aagtaatccc agcttgtctg ccatccccaa attatgtggt cgctgaccgg    900
accgaatgtt tcatcactgg ctggggagaa acccaaggta cttttggagc tggccttctc    960
aaggaagccc agctccctgt gattgagaat aaagtgtgca atcgctatga gtttctgaat   1020
ggaagagtcc aatccaccga actctgtgct gggcatttgg ccggaggcac tgacagttgc   1080
cagggtgaca gtggaggtcc tctggtttgc ttcgagaagg acaaatacat tttacaagga   1140
gtcacttctt ggggtcttgg ctgtgcacgc cccaataagc ctggtgtcta tgttcgtgtt   1200
tcaaggtttg ttacttggat tgagggagtg atgagaaata attaa                   1245
```

<210> SEQ ID NO 8
<211> LENGTH: 414
<212> TYPE: PRT
<213> ORGANISM: Artificial sequence
<220> FEATURE:
<223> OTHER INFORMATION: amino acid sequence of delta-plg(delta-plasminogen)

<400> SEQUENCE: 8

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
```

```
                225                 230                 235                 240
Leu Gly Ala His Gln Glu Val Asn Leu Glu Pro His Val Gln Glu Ile
                    245                 250                 255

Glu Val Ser Arg Leu Phe Leu Glu Pro Thr Arg Lys Asp Ile Ala Leu
                260                 265                 270

Leu Lys Leu Ser Ser Pro Ala Val Ile Thr Asp Lys Val Ile Pro Ala
            275                 280                 285

Cys Leu Pro Ser Pro Asn Tyr Val Val Ala Asp Arg Thr Glu Cys Phe
        290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
                340                 345                 350

Leu Ala Gly Gly Thr Asp Ser Cys Gln Gly Asp Ser Gly Gly Pro Leu
            355                 360                 365

Val Cys Phe Glu Lys Asp Lys Tyr Ile Leu Gln Gly Val Thr Ser Trp
        370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410
```

<210> SEQ ID NO 9
<211> LENGTH: 1104
<212> TYPE: DNA
<213> ORGANISM: Artificial sequence
<220> FEATURE:
<223> OTHER INFORMATION: nucleotide sequence coding for Mini-plg(mini-plasminogen)

<400> SEQUENCE: 9

```
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aggataccg aggcaagagg gcgaccactg ttactgggac gccatgccag      180
gactgggctg cccaggagcc ccatagacac agcattttca ctccagagac aaatccacgg     240
gcgggtctgg aaaaaaatta ctgccgtaac cctgatggtg atgtaggtgg tccctggtgc     300
tacacgacaa atccaagaaa actttacgac tactgtgatg tccctcagtg tgcggcccct     360
tcatttgatt gtgggaagcc tcaagtggag ccgaagaaat gtcctggaag ggttgtaggg     420
gggtgtgtgg cccacccaca ttcctggccc tggcaagtca gtcttagaac aaggtttgga     480
atgcacttct gtggaggcac cttgatatcc ccagagtggg tgttgactgc tgcccactgc     540
ttggagaagt ccccaaggcc ttcatcctac aaggtcatcc tgggtgcaca ccaagaagtg     600
aatctcgaac gcatgttca ggaaatagaa gtgtctaggc tgttcttgga gcccacacga      660
aaagatattg ccttgctaaa gctaagcagt cctgccgtca tcactgacaa agtaatccca     720
gcttgtctgc catccccaaa ttatgtggtc gctgaccgga ccgaatgttt catcactggc     780
tggggagaaa cccaaggtac ttttggagct ggccttctca aggaagccca gctccctgtg     840
attgagaata agtgtgcaa tcgctatgag tttctgaatg gaagagtcca atccaccgaa      900
ctctgtgctg gcatttggc cggaggcact gacagttgcc agggtgacag tggaggtcct     960
ctggtttgct tcgagaagga caaatacatt ttacaaggag tcacttcttg ggtcttggc    1020
```

```
tgtgcacgcc ccaataagcc tggtgtctat gttcgtgttt caaggtttgt tacttggatt    1080
gagggagtga tgagaaataa ttaa                                           1104
```

<210> SEQ ID NO 10
<211> LENGTH: 367
<212> TYPE: PRT
<213> ORGANISM: Artificial sequence
<220> FEATURE:
<223> OTHER INFORMATION: amino acid sequence of Mini-plg(mini-plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
            35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
            115                 120                 125

Val Glu Pro Lys Lys Cys Pro Gly Arg Val Val Gly Gly Cys Val Ala
            130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
            195                 200                 205

Ile Glu Val Ser Arg Leu Phe Leu Glu Pro Thr Arg Lys Asp Ile Ala
            210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285

Tyr Glu Phe Leu Asn Gly Arg Val Gln Ser Thr Glu Leu Cys Ala Gly
    290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335
```

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
        355                 360                 365

<210> SEQ ID NO 11
<211> LENGTH: 750
<212> TYPE: DNA
<213> ORGANISM: Artificial sequence
<220> FEATURE:
<223> OTHER INFORMATION: nucleotide sequence coding for Micro-plg(micro-
      plasminogen)

<400> SEQUENCE: 11
gccccttcat tgattgtgg gaagcctcaa gtggagccga agaaatgtcc tggaagggtt      60 gtagggggt gtgtggccca cccacattcc tggccctggc aagtcagtct tagaacaagg    120
tttggaatgc acttctgtgg aggcaccttg atatcccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga aaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                      750

<210> SEQ ID NO 12
<211> LENGTH: 249
<212> TYPE: PRT
<213> ORGANISM: Artificial sequence
<220> FEATURE:
<223> OTHER INFORMATION: amino acid sequence coding for Micro-plg(micro-
      plasminogen)

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly

```
                130                 135                 140
Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
            210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 13
<211> LENGTH: 684
<212> TYPE: DNA
<213> ORGANISM: Artificial sequence
<220> FEATURE:
<223> OTHER INFORMATION: nucleotide sequence coding for the serine
      protease domain

<400> SEQUENCE: 13

```
gttgtagggg ggtgtgtggc ccacccacat tcctggccct ggcaagtcag tcttagaaca    60
aggtttggaa tgcacttctg tggaggcacc ttgatatccc cagagtgggt gttgactgct   120
gcccactgct tggagaagtc cccaaggcct tcatcctaca aggtcatcct gggtgcacac   180
caagaagtga atctcgaacc gcatgttcag gaaatagaag tgtctaggct gttcttggag   240
cccacacgaa aagatattgc cttgctaaag ctaagcagtc ctgccgtcat cactgacaaa   300
gtaatcccag cttgtctgcc atccccaaat tatgtggtcg ctgaccggac cgaatgtttc   360
atcactggct ggggagaaac ccaaggtact tttggagctg gccttctcaa ggaagcccag   420
ctccctgtga ttgagaataa agtgtgcaat cgctatgagt ttctgaatgg aagagtccaa   480
tccaccgaac tctgtgctgg gcatttggcc ggaggcactg acagttgcca gggtgacagt   540
ggaggtcctc tggtttgctt cgagaaggac aaatacattt tacaaggagt cacttcttgg   600
ggtcttggct gtgcacgccc caataagcct ggtgtctatg ttcgtgtttc aaggtttgtt   660
acttggattg agggagtgat gaga                                          684
```

<210> SEQ ID NO 14
<211> LENGTH: 228
<212> TYPE: PRT
<213> ORGANISM: Artificial sequence
<220> FEATURE:
<223> OTHER INFORMATION: amino acid sequence coding for the serine
      protease domain

<400> SEQUENCE: 14

```
Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
                20                  25                  30

Ser Pro Glu Trp Val Leu Thr Ala Ala His Cys Leu Glu Lys Ser Pro
            35                  40                  45

Arg Pro Ser Ser Tyr Lys Val Ile Leu Gly Ala His Gln Glu Val Asn
```

|   |   |   |   |   | 50 |   |   |   |   | 55 |   |   |   |   | 60 |   |   |
|---|---|---|---|---|----|---|---|---|---|----|---|---|---|---|----|---|---|

Leu Glu Pro His Val Gln Glu Ile Glu Val Ser Arg Leu Phe Leu Glu
65              70              75              80

Pro Thr Arg Lys Asp Ile Ala Leu Leu Lys Leu Ser Ser Pro Ala Val
            85              90              95

Ile Thr Asp Lys Val Ile Pro Ala Cys Leu Pro Ser Pro Asn Tyr Val
            100             105             110

Val Ala Asp Arg Thr Glu Cys Phe Ile Thr Gly Trp Gly Glu Thr Gln
        115             120             125

Gly Thr Phe Gly Ala Gly Leu Leu Lys Glu Ala Gln Leu Pro Val Ile
        130             135             140

Glu Asn Lys Val Cys Asn Arg Tyr Glu Phe Leu Asn Gly Arg Val Gln
145             150             155             160

Ser Thr Glu Leu Cys Ala Gly His Leu Ala Gly Gly Thr Asp Ser Cys
            165             170             175

Gln Gly Asp Ser Gly Gly Pro Leu Val Cys Phe Glu Lys Asp Lys Tyr
            180             185             190

Ile Leu Gln Gly Val Thr Ser Trp Gly Leu Gly Cys Ala Arg Pro Asn
        195             200             205

Lys Pro Gly Val Tyr Val Arg Val Ser Arg Phe Val Thr Trp Ile Glu
    210             215             220

Gly Val Met Arg
225